(12) United States Patent
Felix et al.

(10) Patent No.: US 12,740,737 B2
(45) Date of Patent: Sep. 22, 2026

(54) SYSTEM FOR COIL-BASED IMPLANTABLE PHYSIOLOGICAL MONITOR ENERGY TRANSMISSION

(71) Applicant: Bardy Diagnostics, Inc., Bellevue, WA (US)

(72) Inventors: Jason Felix, Vashon Island, WA (US); Joshua Djon Green, Seattle, WA (US); Gust H. Bardy, Carnation, WA (US); Henry James Millican, Bainbridge Island, WA (US)

(73) Assignee: Bardy Diagnostics, Inc., Bellevue, WA (US)

(*) Notice: Subject to any disclaimer, the term of this patent is extended or adjusted under 35 U.S.C. 154(b) by 0 days.

(21) Appl. No.: 18/611,272

(22) Filed: Mar. 20, 2024

(65) Prior Publication Data

US 2024/0260879 A1 Aug. 8, 2024

Related U.S. Application Data

(63) Continuation of application No. 18/309,659, filed on Apr. 28, 2023, now Pat. No. 11,963,780, which is a (Continued)

(51) Int. Cl.

*A61B 5/308* (2021.01)
*A61B 5/00* (2006.01)

(Continued)

(52) U.S. Cl.

CPC ............ *A61B 5/308* (2021.01); *A61B 5/0006* (2013.01); *A61B 5/0022* (2013.01); *A61B 5/0031* (2013.01); *A61B 5/0245* (2013.01); *A61B 5/283* (2021.01); *A61B 5/319* (2021.01); *A61B 5/335* (2021.01); *A61B 2560/0204* (2013.01); *A61B 2560/0481* (2013.01); *A61B 2562/16* (2013.01)

(58) Field of Classification Search

CPC ....... A61B 5/308; A61B 5/318; A61B 5/0031; A61B 5/686; A61B 2560/0481

See application file for complete search history.

(56) References Cited

U.S. PATENT DOCUMENTS

| | | | |
|---|---|---|---|
| 7,395,106 | B2 | 7/2008 | Ryu et al. |
| 7,468,032 | B2 | 12/2008 | Stahmann et al. |

(Continued)

OTHER PUBLICATIONS

Anand et al., "Design of the Multi-Sensor Monitoring in Congestive Heart Failure (MUSIC) Study: Prospective Trial to Assess the Utility of Continuous Wireless Physiologic Monitoring in Heart Failure", Journal of Cardiac Failure, vol. 17, No. 1, Jan. 1, 2011, pp. 11-16 (6 pages).

(Continued)

*Primary Examiner* — Thaddeus B Cox
(74) *Attorney, Agent, or Firm* — K&L Gates LLP

(57) ABSTRACT

An implantable physiological monitor is provided. The implantable physiological monitor includes a transceiver configured to wirelessly interface with an external device and a housing having a plurality of electrodes. The plurality of electrodes is configured to record an electrocardiography signal and an electrode configuration of the plurality of electrodes can be configured after implanting the implantable physiological monitor.

13 Claims, 36 Drawing Sheets

Related U.S. Application Data continuation of application No. 17/572,172, filed on Jan. 10, 2022, now Pat. No. 11,642,065.

(60) Provisional application No. 63/135,745, filed on Jan. 11, 2021.

(51) Int. Cl.

| | |
|---|---|
| ***A61B 5/0245*** | (2006.01) |
| ***A61B 5/283*** | (2021.01) |
| ***A61B 5/319*** | (2021.01) |
| ***A61B 5/335*** | (2021.01) |

(56) References Cited

U.S. PATENT DOCUMENTS

| | | | | |
|---|---|---|---|---|
| 8,150,502 | B2 | 4/2012 | Kumar et al. | |
| 8,214,007 | B2 | 7/2012 | Baker et al. | |
| 8,538,503 | B2 | 9/2013 | Kumar et al. | |
| 8,647,268 | B2 | 2/2014 | Tran | |
| 8,718,742 | B2 | 5/2014 | Beck et al. | |
| 8,926,509 | B2 | 1/2015 | Magar et al. | |
| 2008/0091089 | A1 | 4/2008 | Guillory et al. | |
| 2009/0062670 | A1 | 3/2009 | Sterling et al. | |
| 2009/0182204 | A1 | 7/2009 | Semler et al. | |
| 2015/0087950 | A1 | 3/2015 | Felix et al. | |
| 2015/0335285 | A1* | 11/2015 | Poon | A61N 7/00 600/301 |
| 2019/0167139 | A1* | 6/2019 | Bardy | A61B 5/0031 |
| 2021/0106281 | A1* | 4/2021 | Tran | A61B 5/486 |

OTHER PUBLICATIONS

Cesario et al., “Arrhythmia Detection with a Low-Profile Wireless Adherent Cardiac Monitor: Results from the ADAM and EVE Studies”, The Journal of Innovations in Cardiac Rhythm Management, 2 (2011) Sep. 2011, pp. 476-482, (7 pages).

Corventis Nuvant, “Nuvant Mobile Cardiac Telementry (MTC) System”, Corventis, 2009, last printed Jul. 18, 2024, https://web.archive.org/web/20100127193736/http://corventis.com/AP/nuvant.asp.

Corventis Avivo, “Avivo Mobile Patient Management System”, Corventis, 2008, lasted printed Jul. 18, 2024, https://web.archive.org/web/20100118155329/http://www.corventis.com/AP/avivo.asp.

IRhythm Zio XT Patch/Event Card, “Zio Patch”, iRhythm, 2011, last printed Jul. 18, 2024, https://web.archive.org/web/20111017074139/http://irhythmtech.com/media/files/Z100A4020.04%20-%20ZIO%20PATCH%20DATA%20SHEET.pdf.

*Bardy Diagnostics, Inc.* v. *Vital Connect, Inc.*, Defendant’s Identification of Supplemental Prior Art References, C.A. No. 22-351 (CJV), May 22, 2024.

International Preliminary Report on Patentability and Written Opinion, PCT/US2019/064331, Jun. 8, 2021.

First Examination Report, Communication pursuant to Article 94(3) EPC, 19 828 053.9-1113, dated Apr. 15, 2024.

* cited by examiner

Fig. 7.
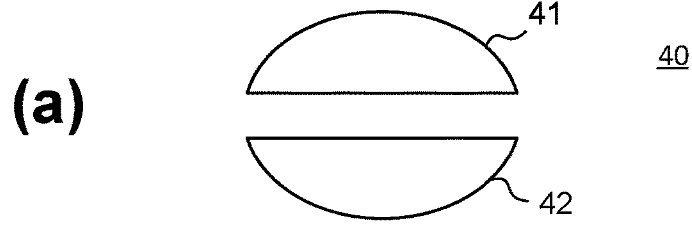
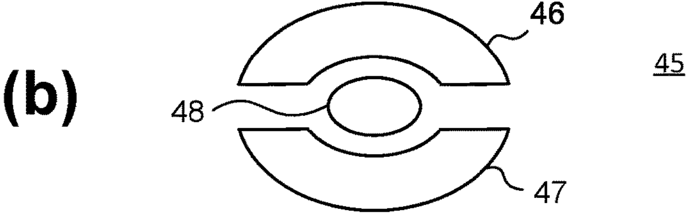
Fig. 8.
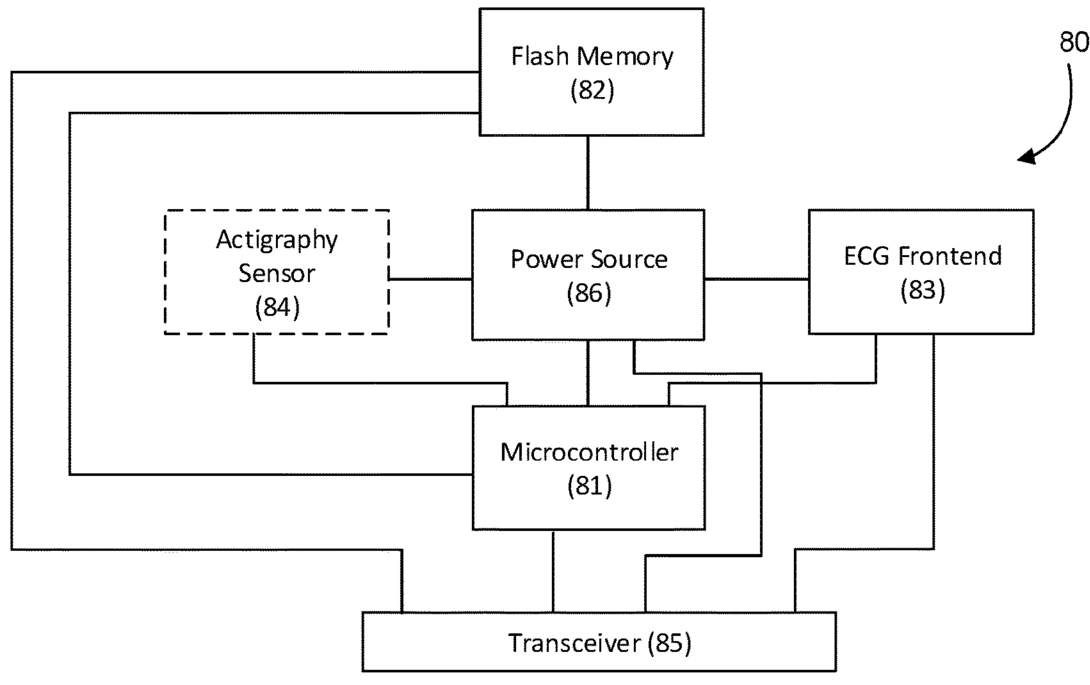

90
94
Mgt
95
92
DL
93
Database
EMRs
96
97
Network
(91)
MD
98
99
100
10
12
13
14
103
APP
102
104

110

380

750

750

263

512

515

527

528

514

516

513

532
532
533
531

530

540

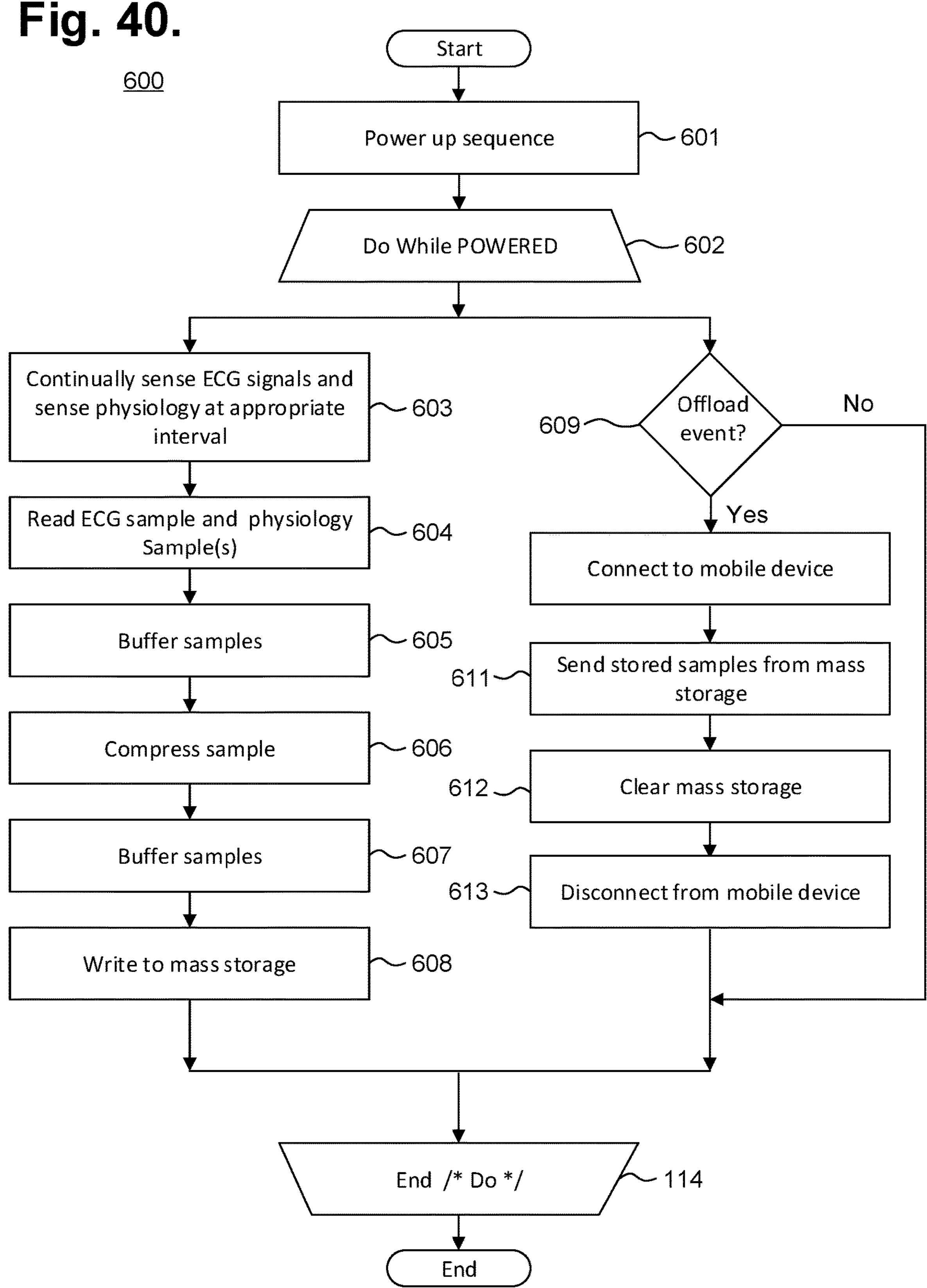
Fig. 40.
600
Start
Power up sequence
601
Do While POWERED
602
Continually sense ECG signals and sense physiology at appropriate interval
603
Read ECG sample and physiology Sample(s)
604
Buffer samples
605
Compress sample
606
Buffer samples
607
Write to mass storage
608
Offload event?
609
No
Yes
Connect to mobile device
Send stored samples from mass storage
611
Clear mass storage
612
Disconnect from mobile device
613
End /* Do */
114
End Fig. 41.
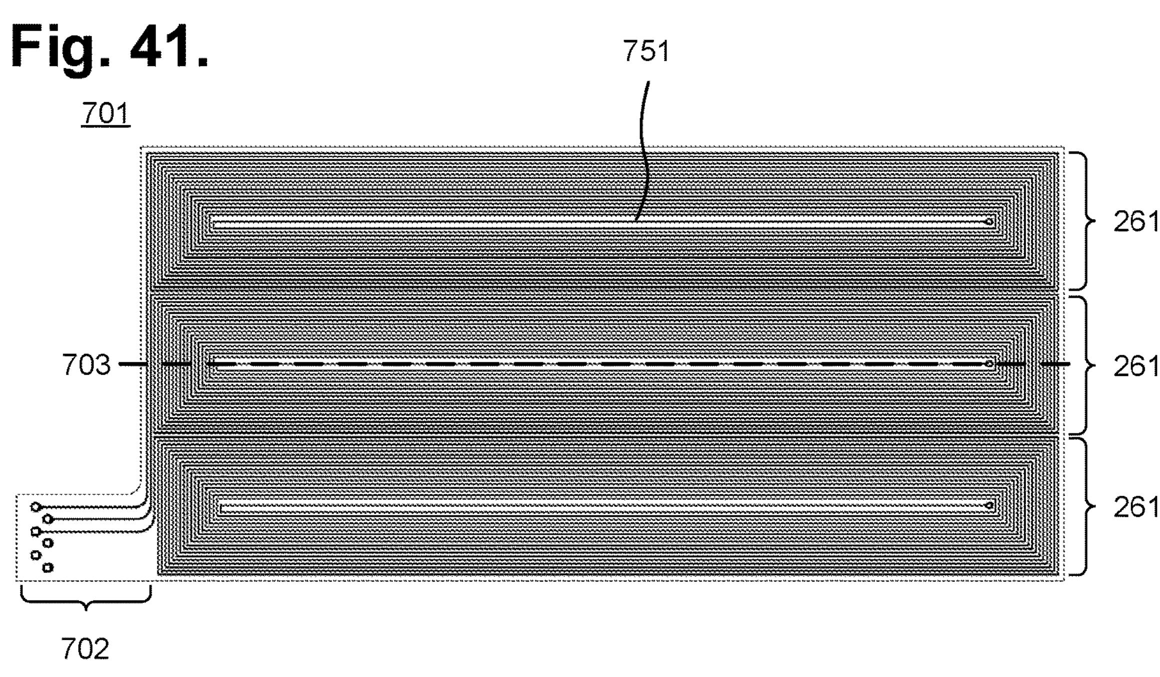
Fig. 42A.
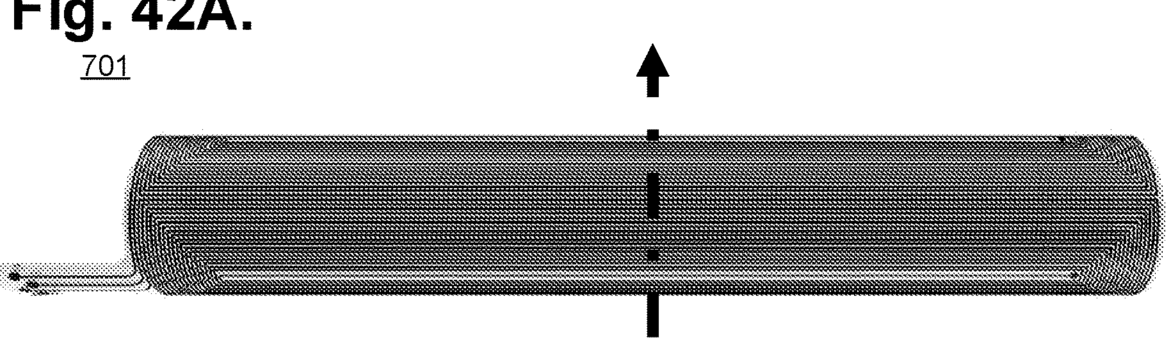
Fig. 42B.
701
704

Fig. 43.
705
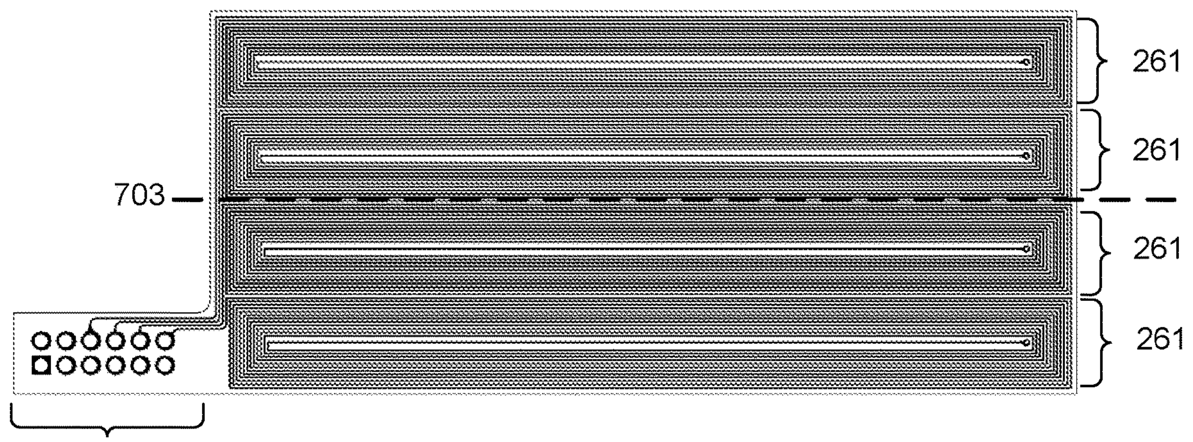
702
Fig. 44A.
705
704
Fig. 44B.
705
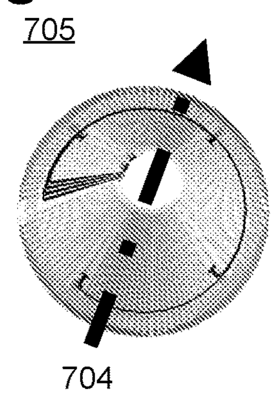

710
742

710
742

SYSTEM FOR COIL-BASED IMPLANTABLE PHYSIOLOGICAL MONITOR ENERGY TRANSMISSION

CROSS-REFERENCE TO RELATED APPLICATIONS

This application is a continuation of U.S. Pat. No. 11,963,780, titled SYSTEM FOR COIL-BASED IMPLANTABLE PHYSIOLOGICAL MONITOR ENERGY TRANSMISSION, which is a continuation of U.S. Pat. No. 11,642,065, filed Jan. 10, 2022, titled System For Induction-Based Subcutaneous Insertable Physiological Monitor Recharging, which claims priority to U.S. Provisional App. 63/135,745, filed Jan. 11, 2021, titled INSERTABLE CARDIAC MONITOR WITH INDUCTION-BASED RECHARGING CAPABILITIES AND A TRANSMITTING COIL FOR RECHARGING THE SAME, the disclosures of which are incorporated by reference herein in their entirety and relied upon.

FIELD

This application relates in general to electrocardiographic monitoring and, in particular, to system for induction-based subcutaneous insertable physiological monitor recharging.

BACKGROUND

The electrocardiogram (ECG) was invented by a Dutch physiologist, Willem Einthoven, in 1903. Physicians have since used ECGs to diagnose heart problems and other medical concerns. The medical and engineering principles underlying Einthoven's work are still applicable today, and although ECG machines have evolved to a broad array of different systems, over the past century, the fundamental role of an ECG machine remains the same: to record from the skin surface transmembrane ionic currents that are generated within the heart during cardiac activation and recovery.

Cardiac depolarization, which is the spread of electrical current throughout the heart, originates in the sinoatrial (SA) node in the right atrium and spreads leftward towards the left atrium and inferiorly towards the atrioventricular (AV) node. Thereafter a delay, occasioned by the AV node, allows atrial blood to enter the ventricles, prior to the continuation of the depolarization current proceeding down the Bundle of His and into the right and left bundle branches, then advancing to the Purkinje fibers, and finally spreading to activate the right and left ventricular muscle fibers themselves that lead to the heart muscle squeezing the blood supply forward.

During each cardiac cycle, the transmembrane ionic currents create an electrical field in and around the heart that can be detected by ECG electrodes either placed on the skin or implanted under the skin of the thorax to record far field electrical signals from the heart. These far field electrical signals are the captured ECG signals that can be visually depicted in an ECG trace as the PQRSTU waveforms, each letter of which represents a specific electrical activity in the heart well known to cardiologists. Within each cardiac cycle, these waveforms indicate key aspects of cardiac electrical activity. The critical P-wave component of each heartbeat represents atrial electrical activity, the electrical signal that is essential if one is to understand heart rhythm disorders. The QRS components represent ventricular electrical activity, equally critical to understanding heart rhythm disorders. The TU components represent ventricular cell voltages that are the result of resetting cellular currents in preparation for the next cardiac cycle. The TU components are generally of limited value for the purposes of understanding heart rhythm disorders and are rarely addressed in the analysis of heart rhythm disorders per se. (Note that the signals involved in the resetting of the atria are so minuscule as to not be visible in an ECG trace or, even in a standard intra-cardiac recording.)

Practically, the QRS components of the ventricle electrical activity are often termed the "R-wave," in brief, as a shorthand way of identifying ventricular electrical activity in its entirety. (Henceforth, the shorthand version of "R-wave" will be used to indicate ventricular activity and "P-wave" will be used to indicate atrial activity.) These "waves" represent the two critical components of arrhythmia monitoring and diagnosis performed every day hundreds of thousands of times across the United States. Without a knowledge of the relationship of these two basic symbols, heart rhythm disorders cannot be reliably diagnosed. Visualizing both the P-wave and the R-wave allow for the specific identification of a variety of atrial tachyarrhythmias (also known as supraventricular tachyarrhythmias, or SVTs), ventricular tachyarrhythmias (VTs), and bradycardias related to sinus node and atrioventricular (AV) node dysfunction. These categories are well understood by cardiologists but only accurately diagnosable if the P-wave and the R-wave are visualized and their relationship and behavior are clear. Visualization of the R-wave is usually readily achievable, as the R-wave is a high voltage, high frequency signal easily recorded from the skin's surface. However, as the ECG bipole spacing and electrode surface area decreases, even the R-wave can be a challenge to visualize. To make matters of rhythm identification more complicated, surface P-waves can be much more difficult to visualize from the surface because of their much lower voltage and signal frequency content. P-wave visualization becomes exacerbated further when the recording bipole inter-electrode spacing decreases.

Subcutaneous ECG monitors, because of their small size, have greater problems of demonstrating a clear and dependable P-wave. The issues related to a tiny atrial voltage are exacerbated by the small size of insertable cardiac monitors (ICMs), the signal processing limits imposed upon them by virtue of their reduced electrode size, and restricted inter-electrode spacing. Conventional subcutaneous ICMs, as well as most conventional surface ECG monitors, are notorious for poor visualization of the P-wave, which remains the primary reason that heart rhythm disorders cannot precisely be identified today from ICMs. Furthermore, even when physiologically present, the P-wave may not actually appear on an ECG because the P-wave's visibility is strongly dependent upon the signal capturing ability of the ECG recording device's sensing circuitry. This situation is further influenced by several factors, including electrode configuration, electrode surface areas and shapes, inter-electrode spacing; where the electrodes are placed on or within the body relative to the heart's atria. Further, the presence or absence of ambient noise and the means to limit the ambient noise is a key aspect of whether the low amplitude atrial signal can be seen.

Conventional ICMs are generally capable of monitoring a patient's heart rhythm for up to three years and are often used after diagnostic measures when dermal ECG monitors fail to identify a suspected arrhythmia. Consequently, when a physician is strongly suspicious of a serious cardiac rhythm disorder that may have caused loss of consciousness or stroke, for example, the physician will often proceed to the insertion of an ICM under the skin of the thorax.

Although traditionally, the quality of the signal is limited with ICMs with respect to identifying the P-wave, the duration of monitoring is hoped to compensate for poor P-wave recording. This situation has led to a dependence on scrutiny of R-wave behavior, such as RR interval (R-wave-to-R-wave interval) behavior, often used as a surrogate for diagnosing atrial fibrillation, a potential cause of stroke. To a limited extent, this approach has some degree of value. Nevertheless, better recording of the P-wave would result in a significant diagnostic improvement, not only in the case of atrial fibrillation, but in a host of other rhythm disorders that can result in syncope or loss of consciousness, like VT or heart block.

The P-wave is the most difficult ECG signal to capture by virtue of originating in the low tissue mass atria and having both low voltage amplitude and relatively low frequency content. Notwithstanding these physiological constraints, ICMs are popular, albeit limited in their diagnostic yield. The few ICMs that are commercially available today, including the Reveal LINQ ICM, manufactured by Medtronic, Inc., Minneapolis, MN, the BioMonitor 2 (AF and S versions), manufactured by Biotronik SE & Co. KG, Berlin, Germany, and the Abbott Confirm Rx ICM, manufactured by Abbott Laboratories, Chicago, IL, all are uniformly limited in their abilities to clearly and consistently sense, record, and deliver the P-wave.

Typically, the current realm of ICM devices use a loop recorder where cumulative ECG data lasting for around an hour is continually overwritten unless an episode of pre-programmed interest occurs or a patient marker is manually triggered. The limited temporal window afforded by the recordation loop is yet another restriction on the evaluation of the P-wave, and related cardiac morphologies, and further compromises diagnostic opportunities.

For instance, Medtronic's Reveal LINQ ICM delivers long-term subcutaneous ECG monitoring for up to three years, depending on programming. The monitor is able to store up to 59 minutes of ECG data, include up to 30 minutes of patient-activated episodes, 27 minutes of automatically detected episodes, and two minutes of the longest atrial fibrillation (AF) episode stored since the last interrogation of the device. The focus of the device is more directed to recording duration and programming options for recording time and patient interactions rather than signal fidelity. The Reveal LINQ ICM is intended for general purpose ECG monitoring and lacks an engineering focus on P-wave visualization. Moreover, the device's recording circuitry is intended to secure the ventricular signal by capturing the R-wave, and is designed to accommodate placement over a broad range of subcutaneous implantation sites, which is usually sufficient if one is focused on the R-wave given its amplitude and frequency content, but of limited value in capturing the low-amplitude, low-frequency content P-wave. Finally, electrode spacing, surface areas, and shapes are dictated (and limited) by the physical size of the monitor's housing which is quite small, an aesthetic choice, but unrealistic with respect to capturing the P-wave.

Similar in design is the titanium housing of Biotronik's BioMonitor 2 but with a flexible silicone antenna to mount a distal electrode lead, albeit of a standardized length. This standardized length mollifies, in one parameter only, the concerns of limited inter-electrode spacing and its curbing effect on securing the P-wave. None of the other factors related to P-wave signal revelation are addressed. Therefore the quality of sensed P-waves reflects a compromise caused by closely-spaced poles that fail to consistently preserve P-wave fidelity, with the reality of the physics imposed problems of signal-to-noise ratio limitations remaining mostly unaddressed.

Further, the physical size of existing implantable monitors limits the size of a power source present in those monitors, which in turn limits a duration of a monitoring possible without a surgical intervention to replace the power source in the monitoring. For a patient whose condition requires extended, potentially periodic life-long monitoring, the existing implantable monitors are of a limited usefulness, subjecting them to surgical intervention and possible associated complications when the power supply of such an implantable monitor runs out.

Recharging such monitors is not a trivial matter, however, as many techniques that are used for recharging batteries are not applicable when the battery is implanted in a patient and a charging wire cannot simply be connected to a battery, especially in a case of an obese patient where the implanted device is buried beneath a thick layer of fat. Those techniques that do allow for remote charging, such as inductive charging, cannot be directly translated from other industries. Whereas in many other industries the speed of recharging can be prioritized without worry of the battery or the battery's surrounding overheating, overheating is a grave concern when the battery being recharged is implanted inside a patient. Even as a slight overheating of the battery or the battery's surrounding can cause discomfort and pain to the patient; a significant overheating can damage the patient's tissues, endangering the patient's health and likely requiring a removal of the inserted monitor from the patient. Overheating of the battery can also cause the battery to explode, which may be potentially fatal for the patient. On the other hand, if the speed of recharging is too slow, the patient is inconvenienced, and is less likely to spend sufficient time recharging the monitor, increasing the chances that the monitor will fail without the charging being complete.

Further, the limitations of the power supply impact how often and how much the implantable monitor offloads collected data due to a large power consumption associated with the wireless transmission.

Therefore, a need remains for a continuously recording long-term ICM particularly attuned to capturing low amplitude cardiac action potential propagation from the atria, that is, the P-wave, for accurate arrhythmia event capture and subsequent diagnosis, and that can be recharged at a high speed without endangering the patient.

SUMMARY

Long-term electrocardiographic and physiological monitoring over a period lasting up to several years in duration can be provided through a continuously-recording rechargeable subcutaneous insertable cardiac monitor (ICM. The length of the monitoring is extended, potentially for a life time of the patient, by including an internal energy harvesting module in the ICM. The energy harvesting module harvests energy from outside the ICM, and provides the harvested energy for powering the circuitry of the ICM, either directly or by recharging a power cell within the ICM. As the circuitry of the ICM requires a low amount of electrical power, the harvested energy can be sufficient to support the functioning of the ICM even when the electrical power stored on the ICM at the time of implantation runs out. The presence of the energy harvesting module further allows for a frequent wireless transmission of a large amount of collected data.

Internally, the energy harvesting module can include at least two overlapping receiving coils that are spaced to be orthogonal to each other and that have a tilt angle of substantially 45°. Such overlapping wire combination allows to minimize mutual inductance of the solenoid coils and increase the rate at which energy can be provided to the energy harvesting module. Further, the rate at which the energy is transmitted from the outside can be increased by defining in a transmitting coil a substantially triangular gap. The combination of the overlapping coils inside the ICM and the transmitting coil with the substantially triangular gap allows to substantially increase the rate at which the ICM can be recharged without overheating the ICM or the surrounding thoracic tissues of the patient. The ICM can be used for performing not only cardiac monitoring, but also other types of physiological monitoring. The energy harvesting module described and the transmitting coil can be used to charge a wide variety of implantable medical devices of a wide variety of shapes and configurations.

In one embodiment, a system for coil-based implantable physiological monitor energy transmission is provided. The system includes a transmitting coil includes a portion defining a triangular gap and configured to generate a magnetic field when electricity is applied to the transmitting coil, wherein the magnetic field causes a generation of a current within one or more receiving coils comprised in an implantable physiological monitor and wherein a magnitude of a dimension of the triangular gap is inversely proportional to a rate of the generation of the current by the one or more receiving coils.

In a further embodiment, a system for powering an implantable physiological monitor is provided. The system includes an implantable physiological monitor that includes one or more receiving coils. The system further includes a device external to the implantable physiological monitor and including a transmitting coil and a source of electricity, the transmitting coil comprising a portion defining a triangular gap and configured to generate a magnetic field when the electricity is applied to the transmitting coil, wherein the magnetic field causes a generation of a current within the one or more receiving coils, at least a portion of the current is used to power the implantable physiological monitor, and wherein a magnitude of a dimension of the triangular gap is inversely proportional to a rate of the generation of the current by the one or more receiving coils.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTIONS OF DRAWINGS

FIG. 7 is a plan view showing further electrode configurations.

FIG. 8 is a functional block diagram showing the P-wave focused component architecture of the circuitry of the ICM of FIG. 1.

Figure 20:
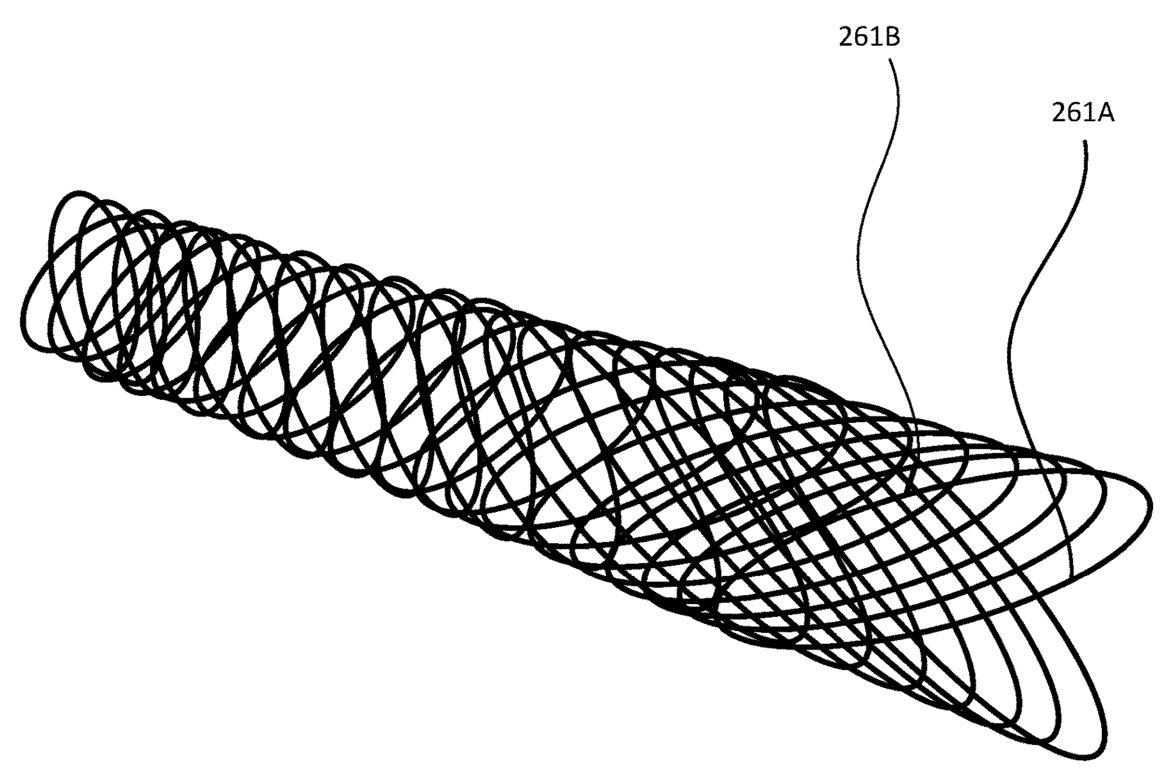
FIG. 20 is a diagram showing overlapping receiving coils for use in the energy harvesting module to receive energy from an external transmitting coil via inductive coupling in accordance with one embodiment.
Figure 26A:
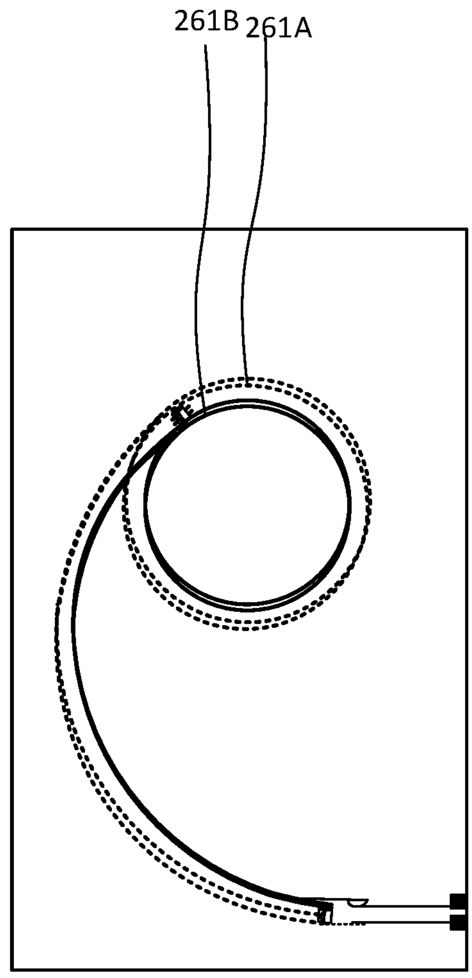
Figure 26B:
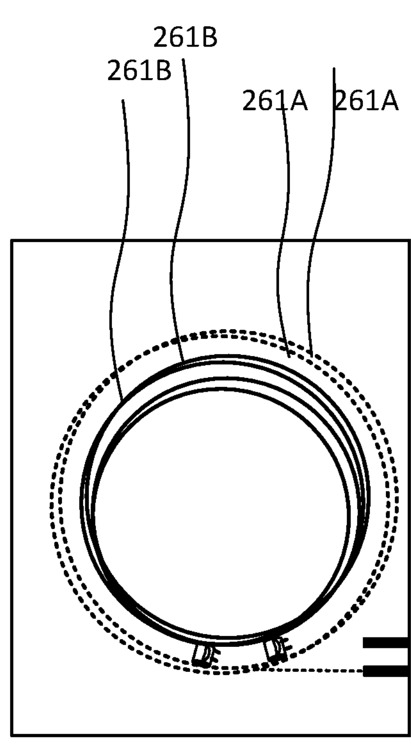

FIGS. 26A-26B provide a bottom view of unwrapped solenoids being wrapped into the coils seen with reference to FIG. 20 in accordance with one embodiment.

Figure 27:
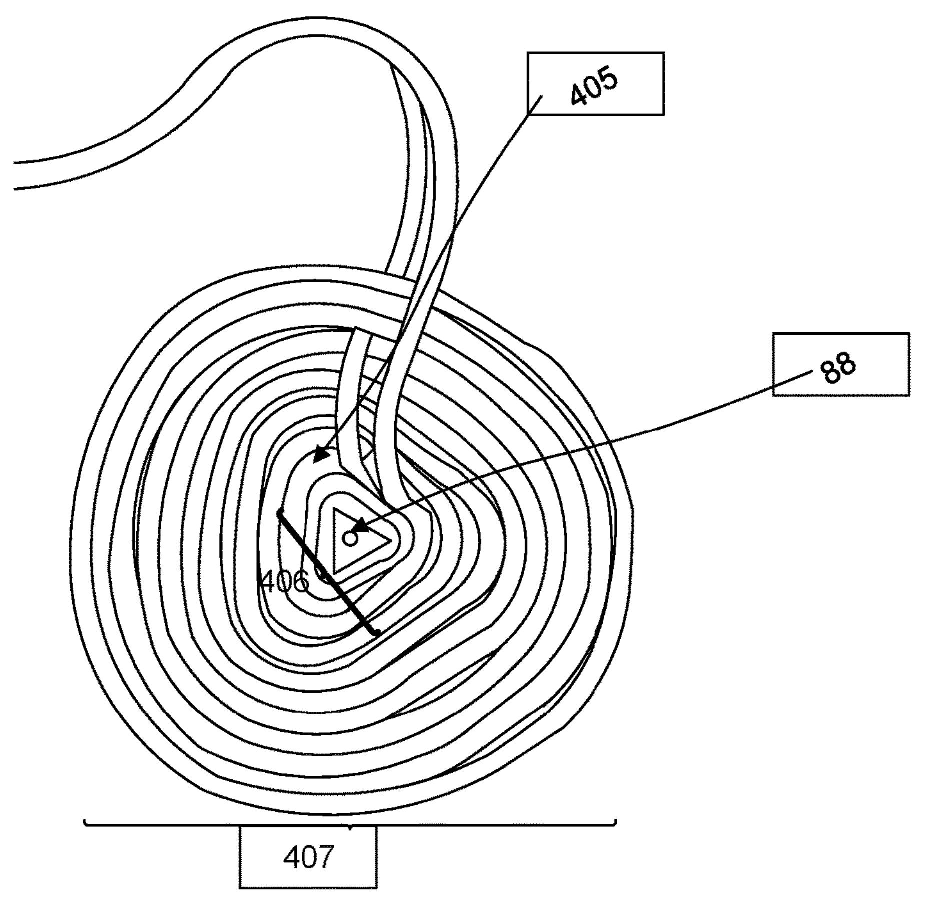

FIG. 27 is a diagram showing a transmitting coil that defines a gap shaped substantially as a triangle with rounded corners in accordance with one embodiment.

Figure 28:
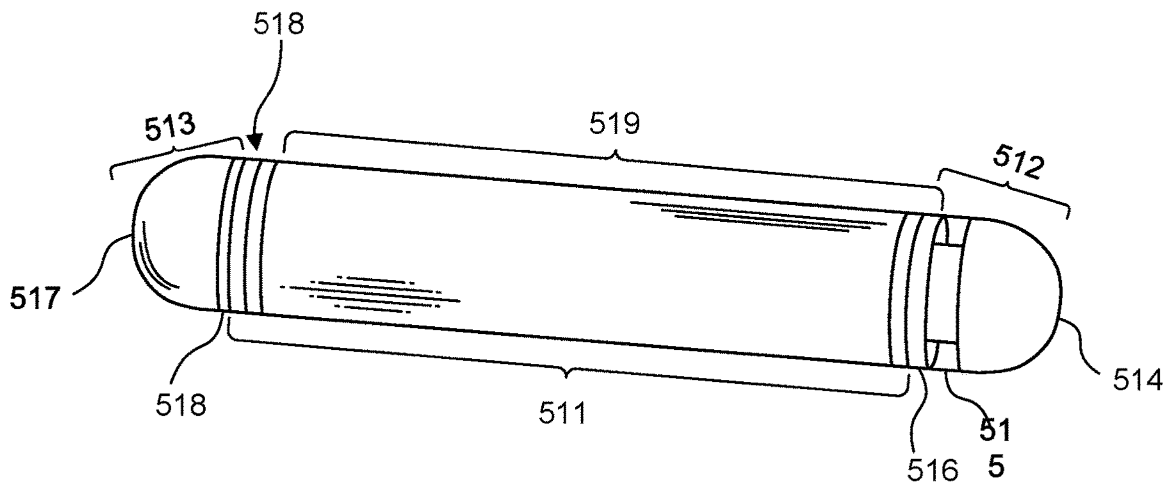

FIG. 28 is an outer perspective view showing an IMD that houses a configurable hardware platform for physiological monitoring of a living body in accordance with one embodiment.

Figure 29:
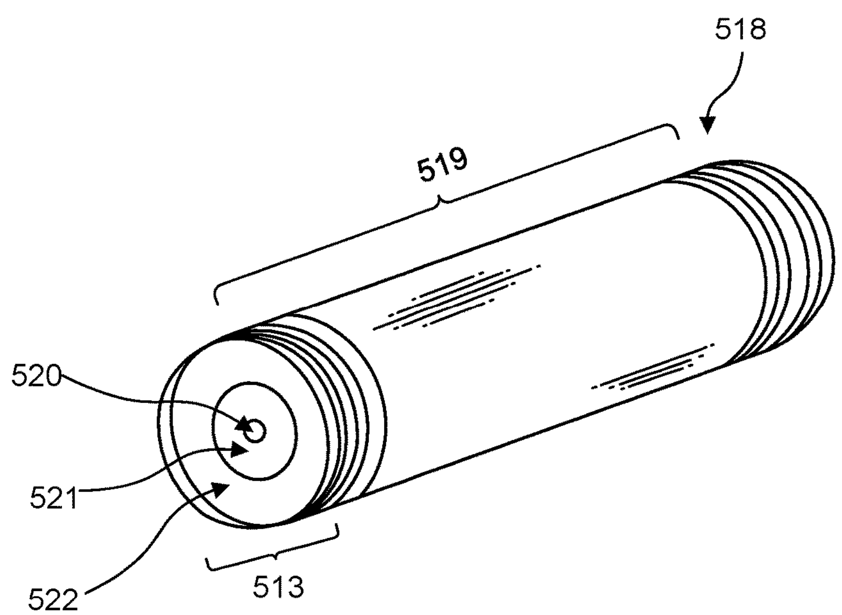

FIG. 29 is an outer perspective view showing the central tubular body of the IMD of FIG. 28.

Figure 30:
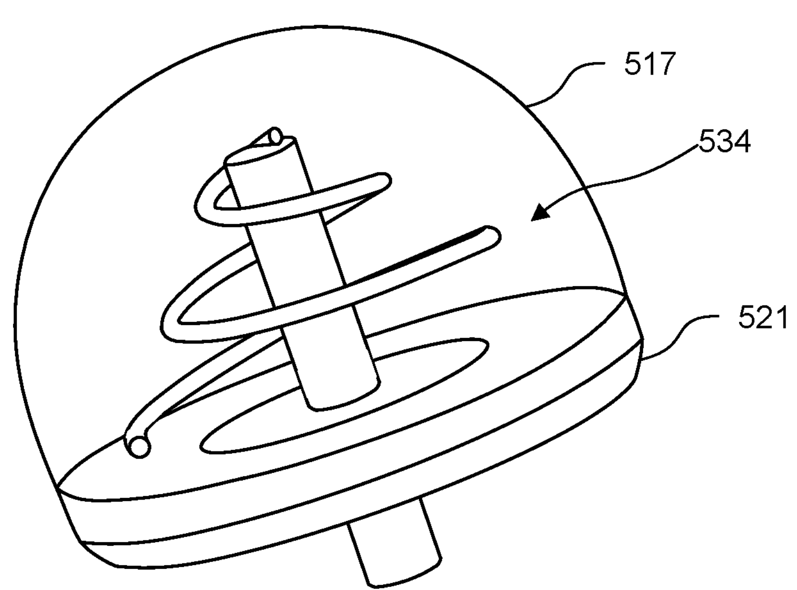

FIG. 30 is a side perspective view showing the semi spherical end cap ("Radome") of the IMD of FIG. 28.

Figure 31:
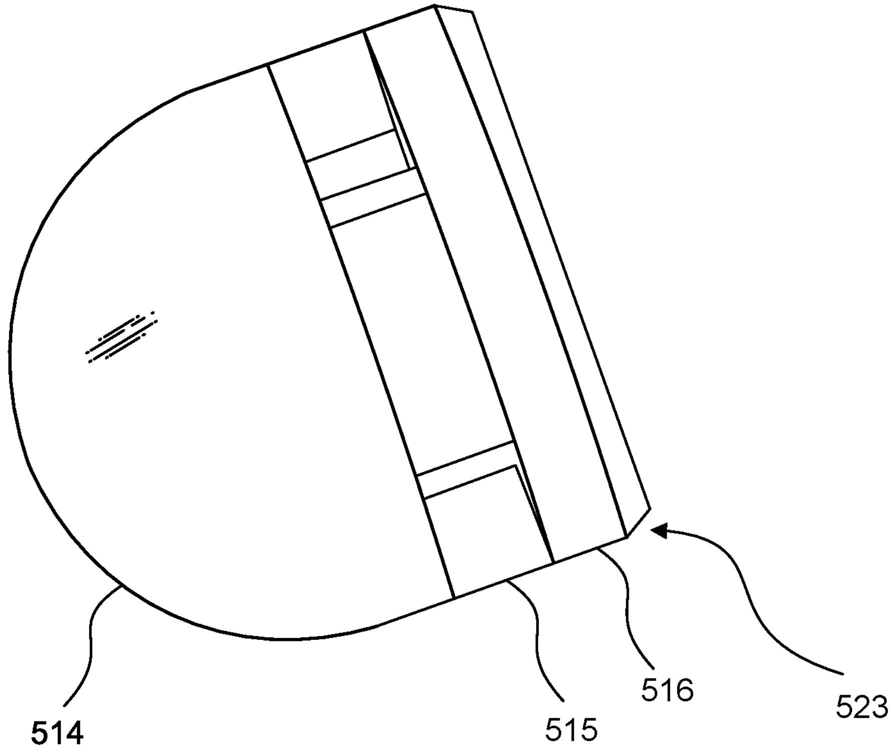

FIG. 31 is a side perspective view showing the electrically conductive semi spherical end cap ("Protectrode") of the IMD of FIG. 28.

Figure 32:
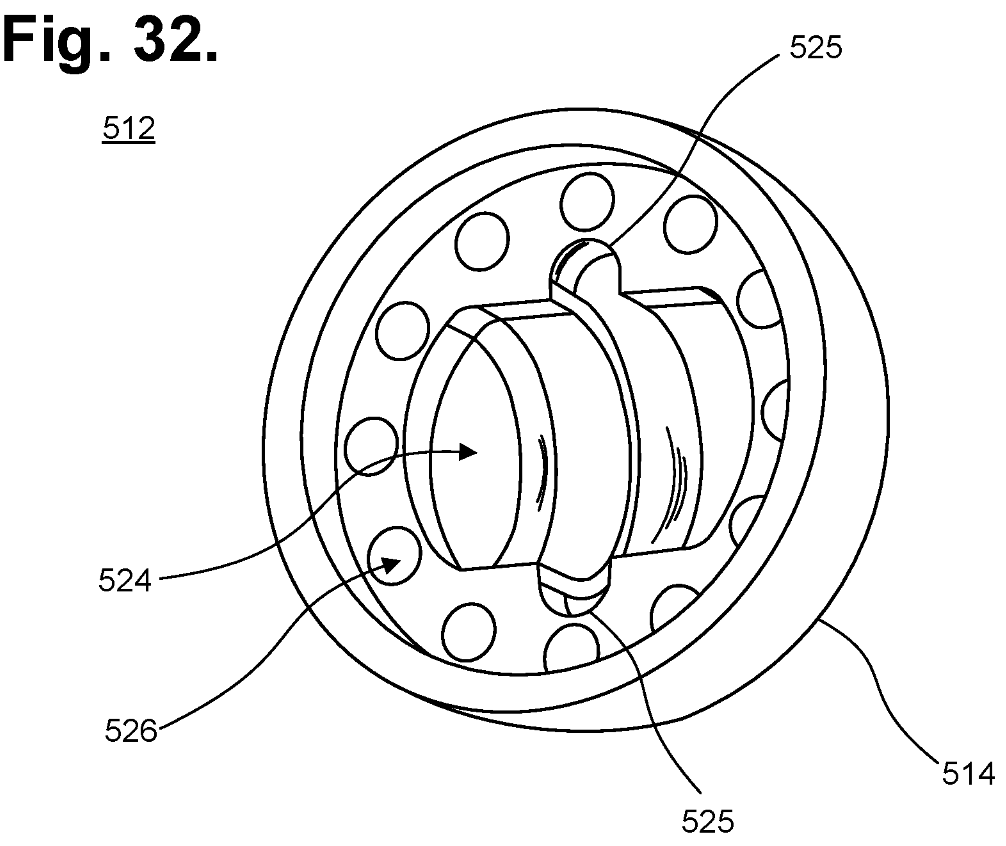

FIG. 32 is an inside perspective view showing the interior of the end cap of the "Protectrode" of FIG. 31.

Figure 33:
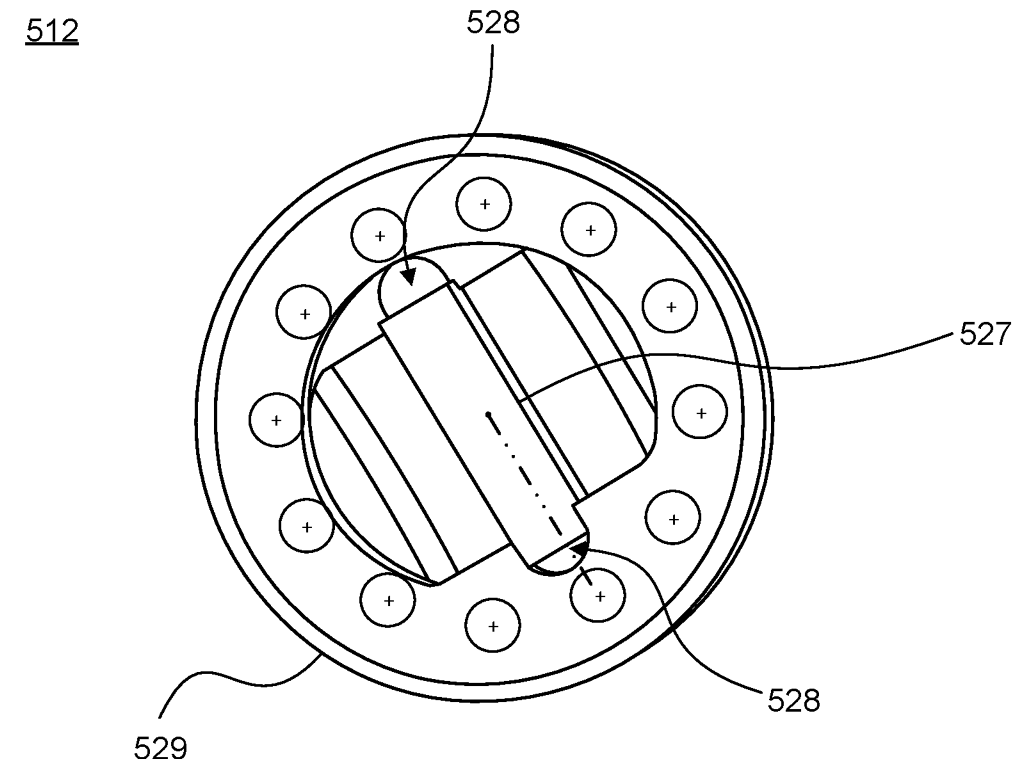

FIG. 33 is an inside perspective view showing the interior of the end cap of the "Protectrode" of FIG. 31.

Figures 34, 35:
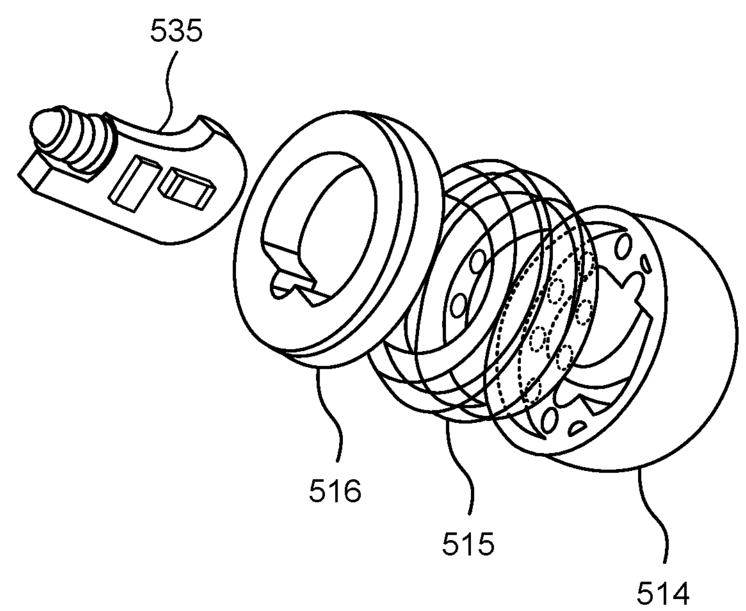

FIG. 34 is an inside perspective view showing the interior of the fully assembled "Protectrode" of FIG. 31.

FIG. 35 is an exploded perspective view showing the components of the "Protectrode" of FIG. 31.

Figure 36:
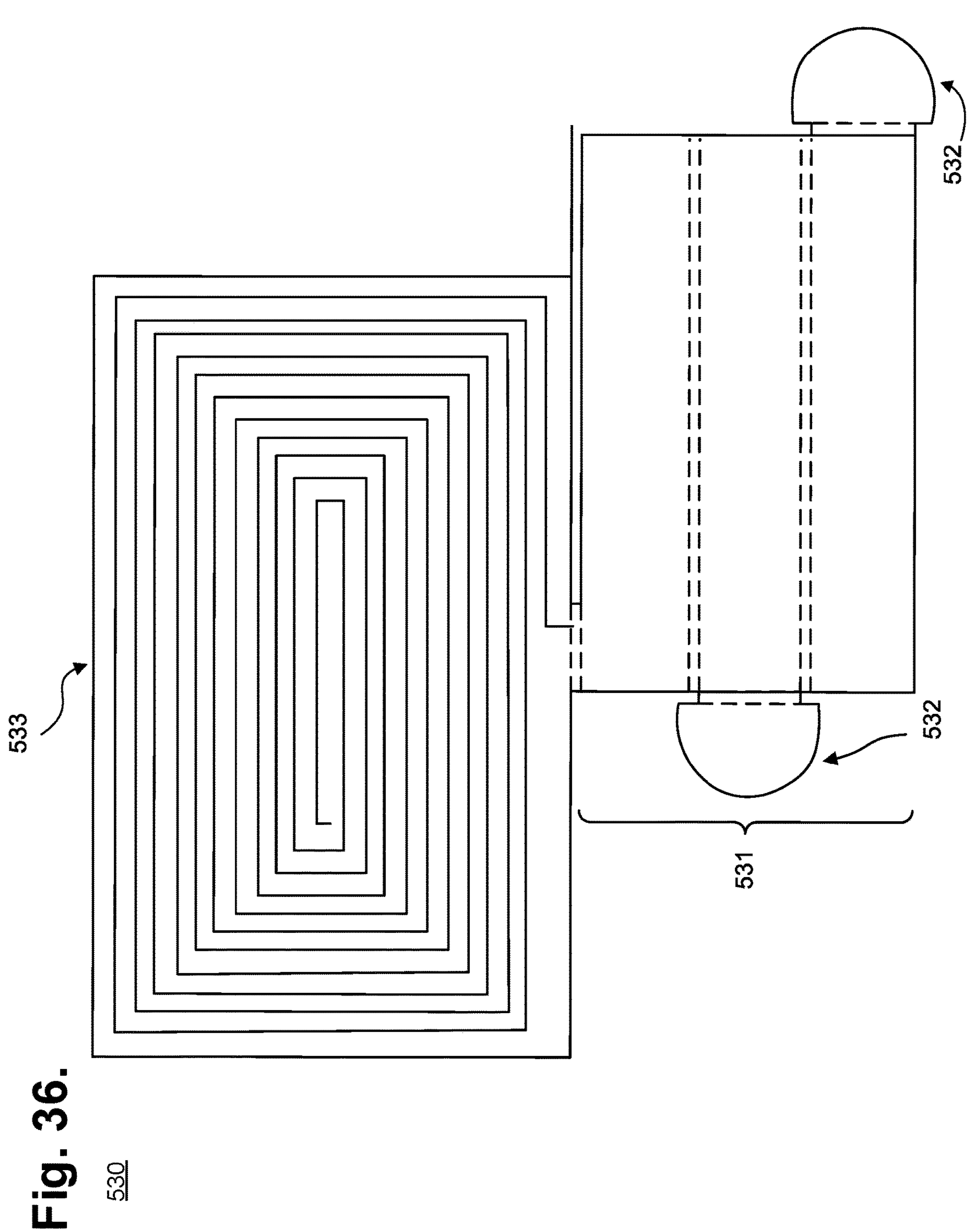

FIG. 36 is a top plan view of a flexible circuit board for use in the IMD of FIG. 28 in a flat, unfolded form.

Figure 37:
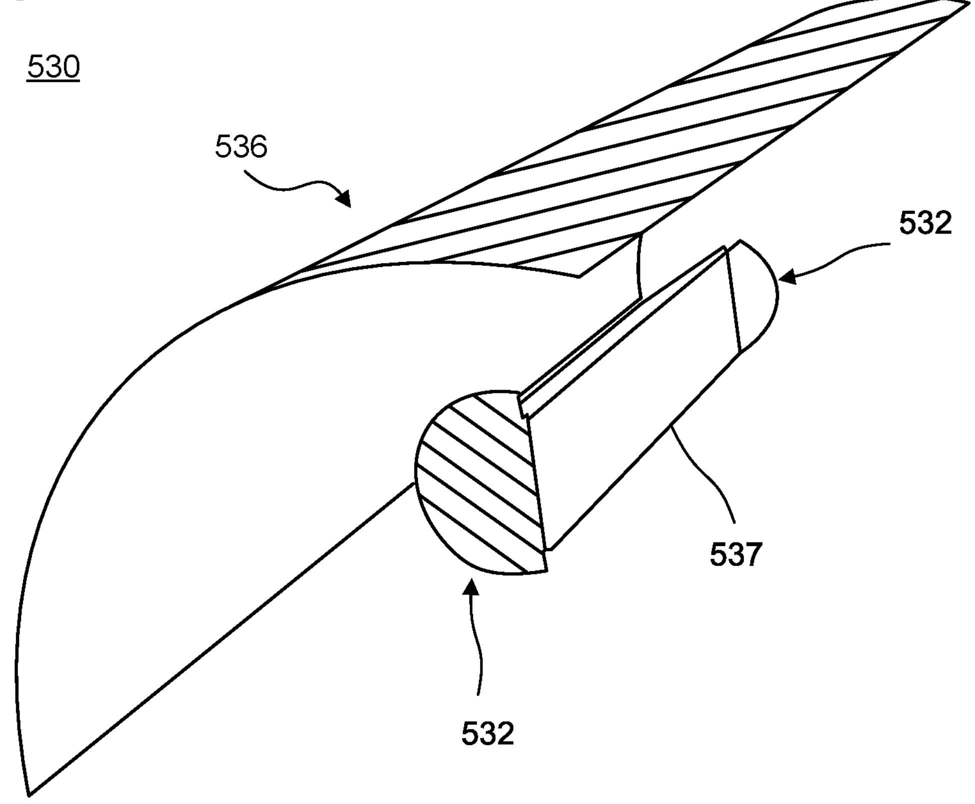

FIG. 37 is a three-quarters perspective view of the flexible circuit board of FIG. 36 in a semi-folded configuration.

Figure 38:
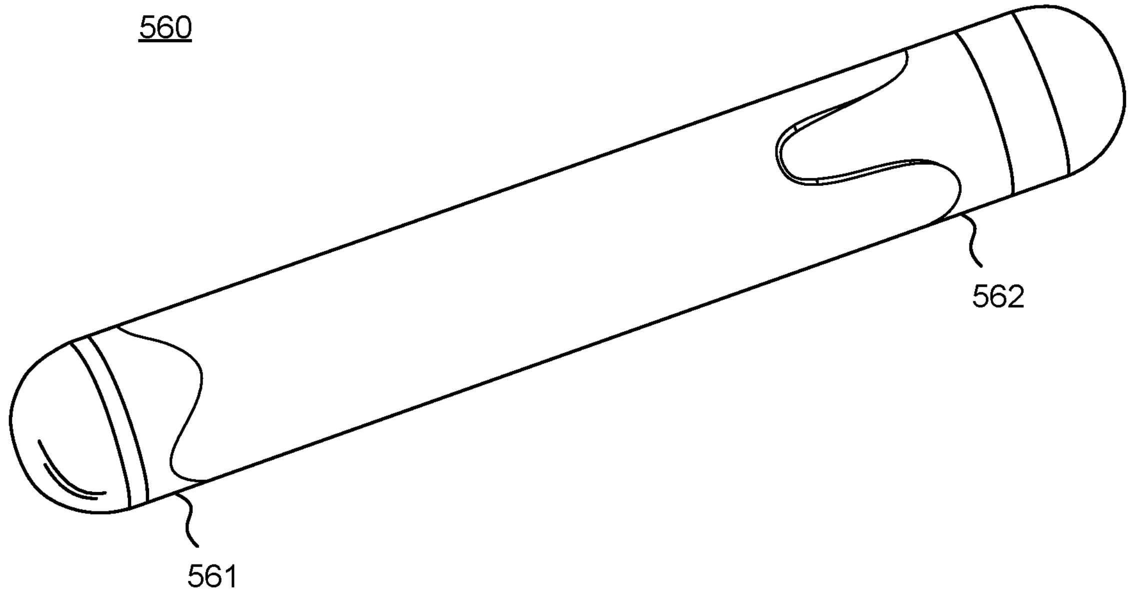

FIG. 38 is an outer perspective view showing an IMD that houses a configurable hardware platform for physiological monitoring of a living body in accordance with a further embodiment.

Figure 39:
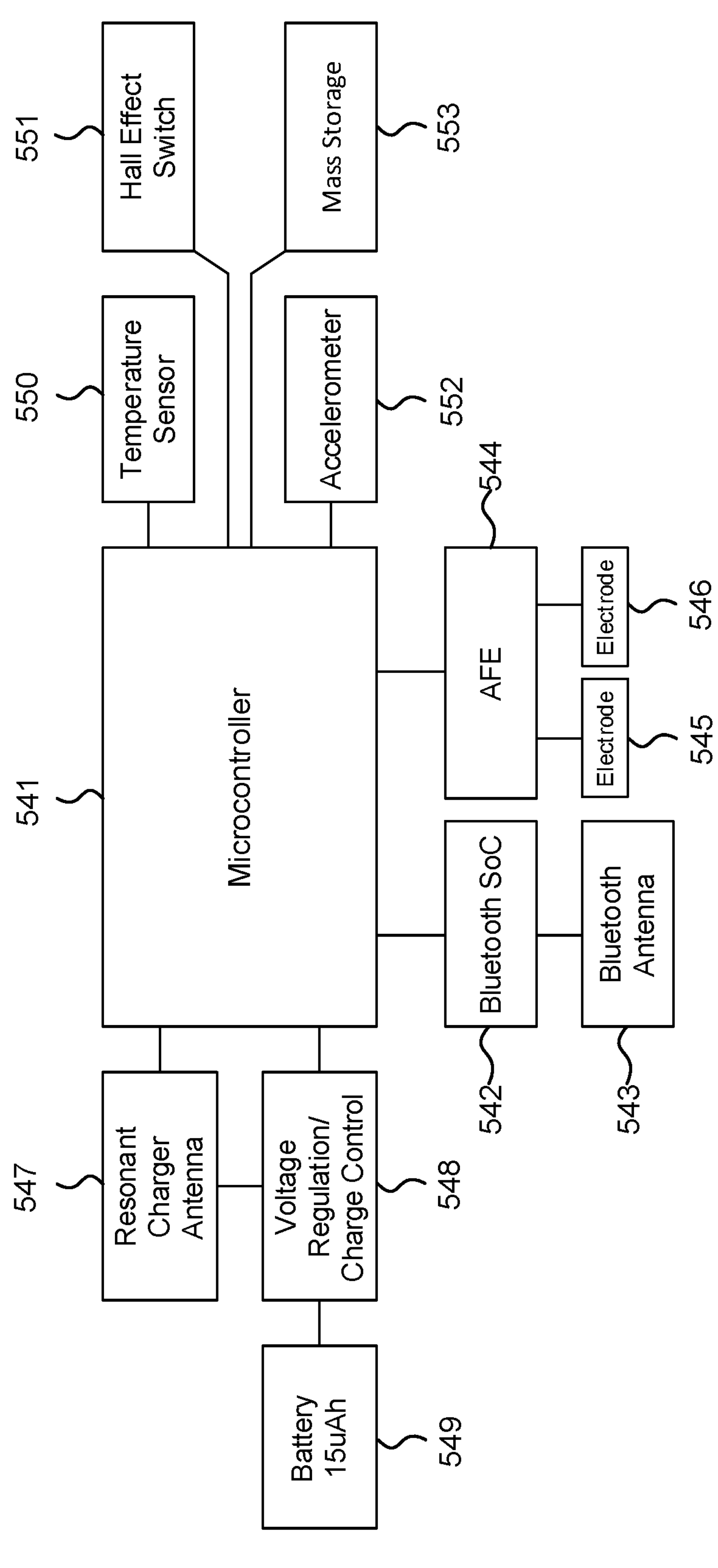

FIG. 39 is a block diagram showing the microarchitecture of the IMD of FIG. 28.

FIG. 40 is a flow diagram showing a method for continuously monitoring electrocardiography for use in the IMD of FIG. 28.

FIG. 41 is a diagram showing an unrolled 3-phase coil that is composed of three receiving coils in accordance with one embodiment.

FIGS. 42A and 42B show two views of the 3-phase coil of FIG. 41 when rolled up in accordance with one embodiment.

FIG. 43 is a diagrams showing an unrolled 4-phase coil that is composed of four receiving coils in accordance with one embodiment.

FIGS. 44A and 44B show two views of the 4-phase coil of FIG. 42 when rolled up in accordance with one embodiment.

Figure 45:
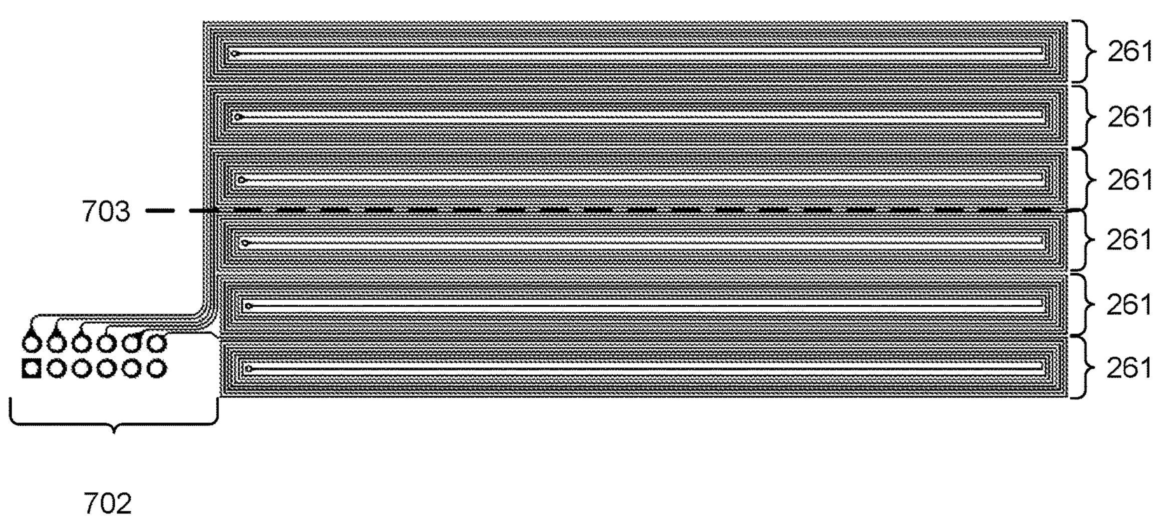

FIG. 45 is a diagrams showing an unrolled 6-phase coil that is composed of six receiving coils in accordance with one embodiment.

Figure 46A:
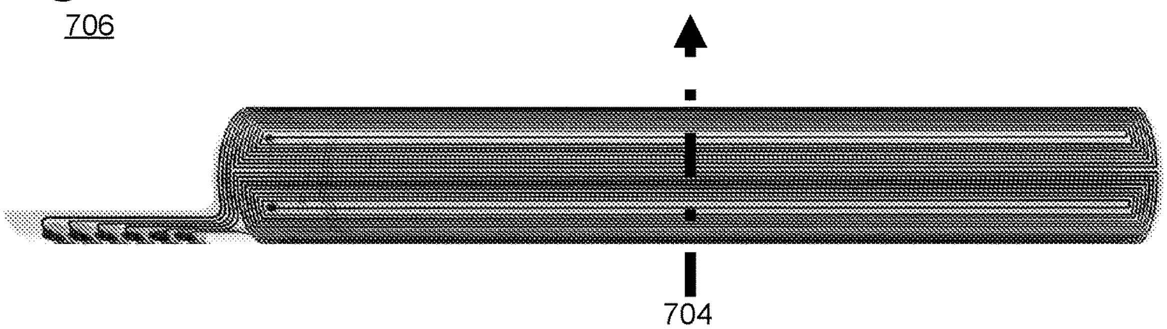
Figure 46B:
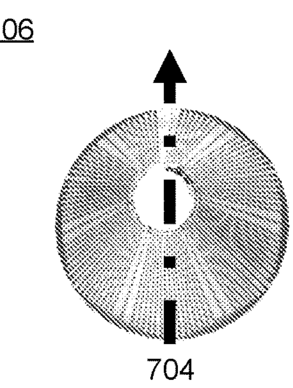

FIGS. 46A and 46B show two views of the 6-phase coil of FIG. 44 when rolled up in accordance with one embodiment.

Figure 47A:
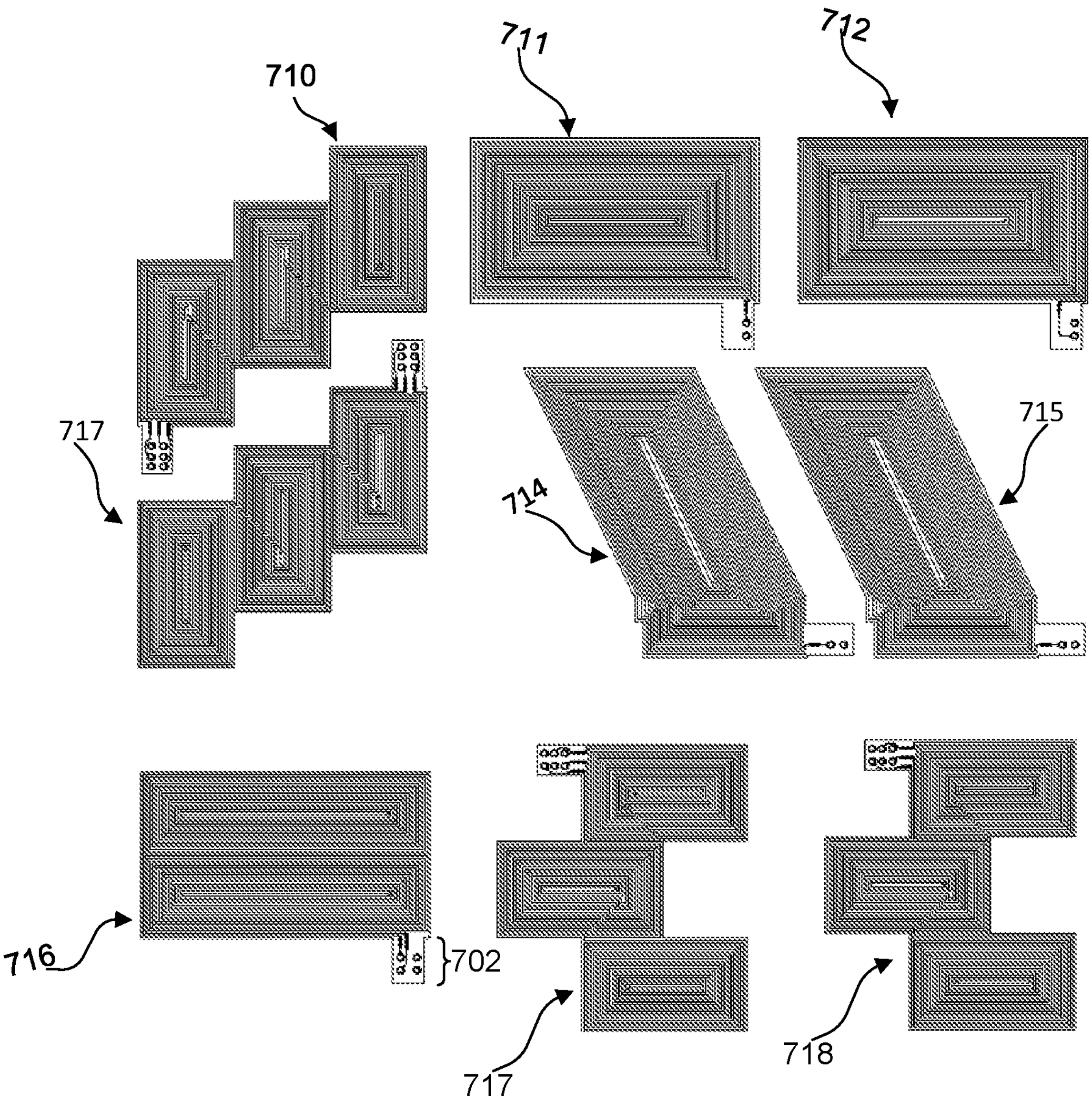
Figure 47B:
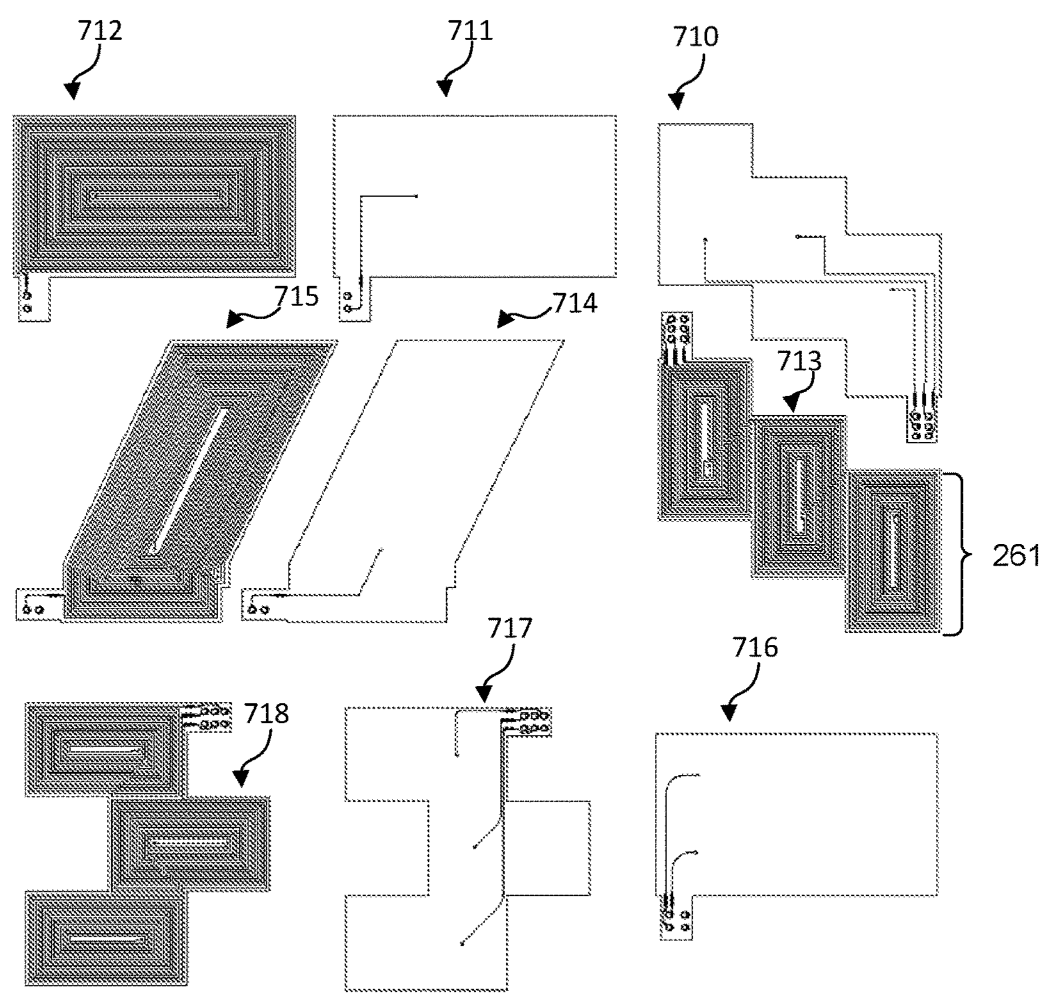

FIGS. 47A-47B show a plurality of unwrapped coils in accordance with one embodiment.

Figure 48:
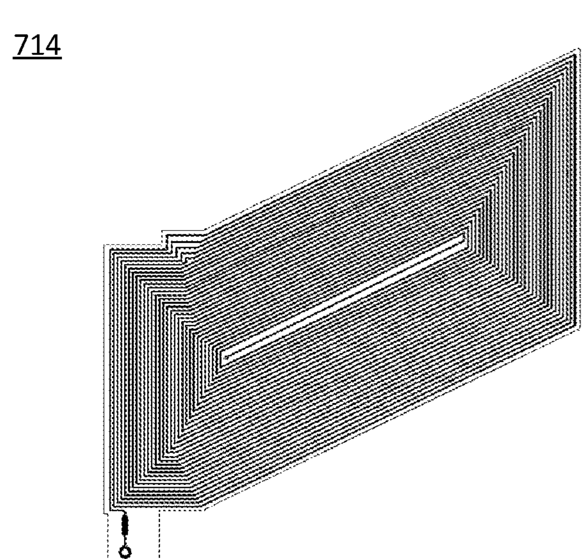

FIG. 48 is an expanded view of the unrolled coil of FIGS. 47A-47B in accordance with one embodiment.

Figure 49A:
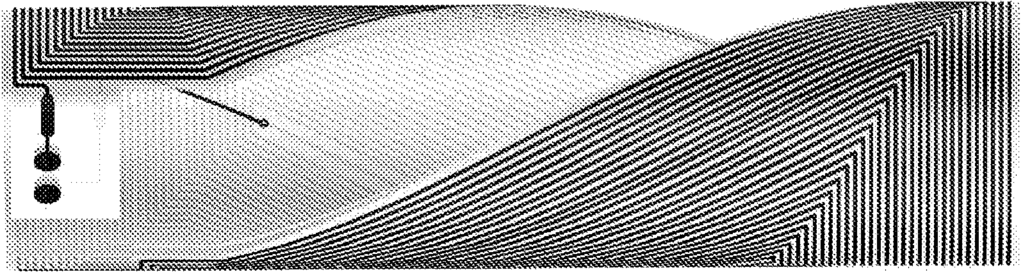

FIG. 49A shows a partially rolled-up coil.

Figure 49B:
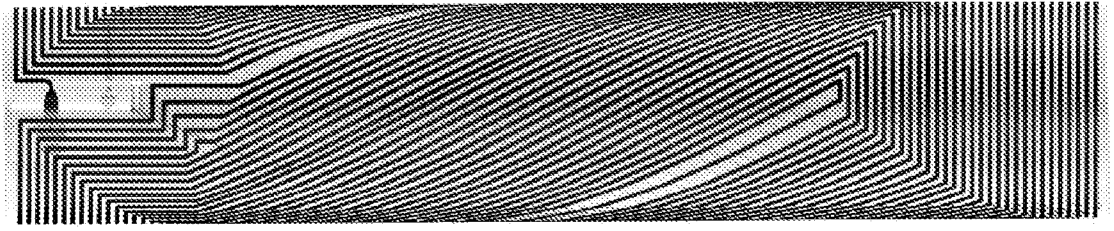

FIG. 49B shows fully-rolled up coil.

Figures 50, 51:
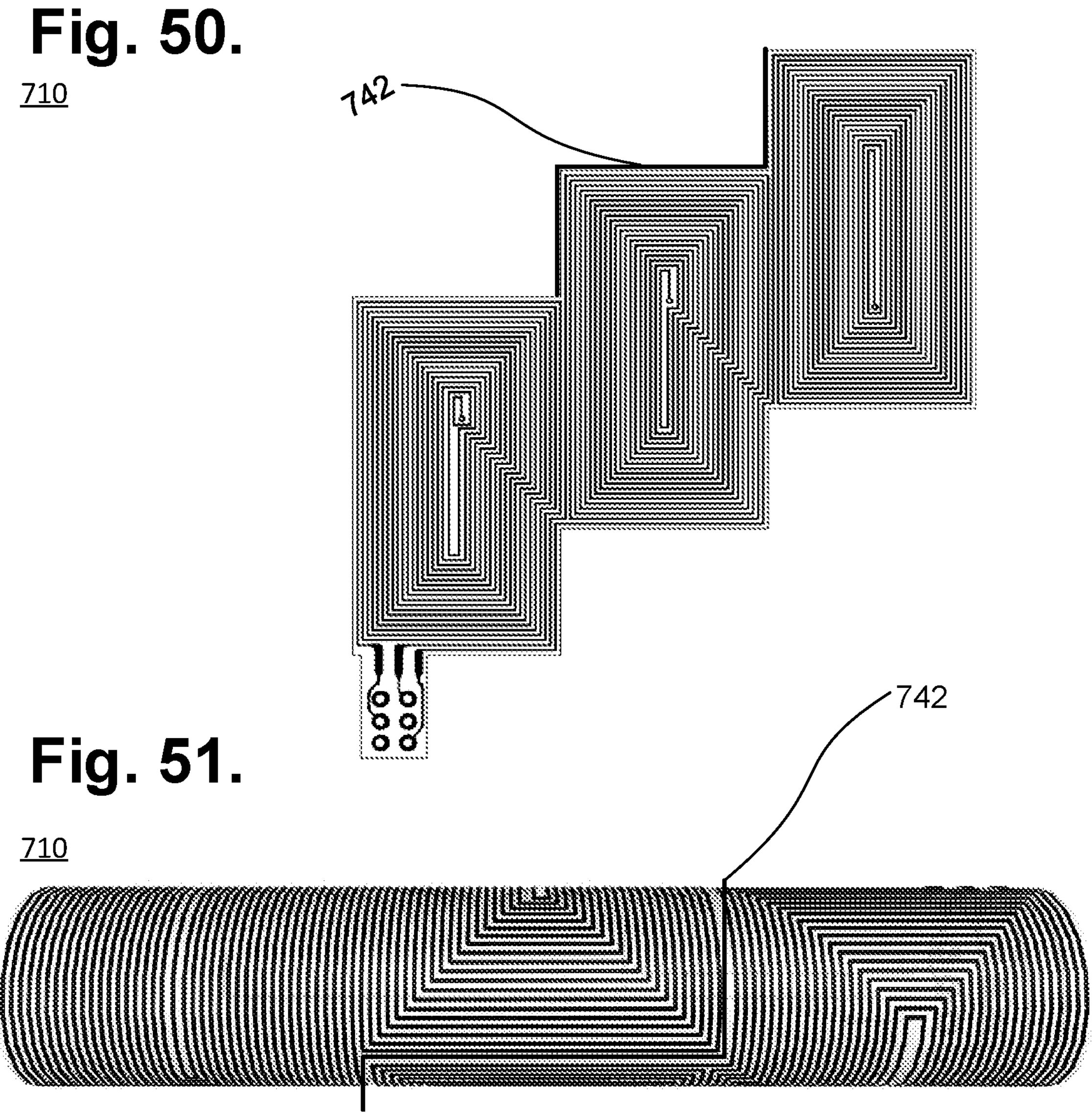

FIG. 50 is an expanded view of the unrolled coil of FIGS. 47A-47B.

FIG. 51 shows fully-rolled up coil.

Figure 52:
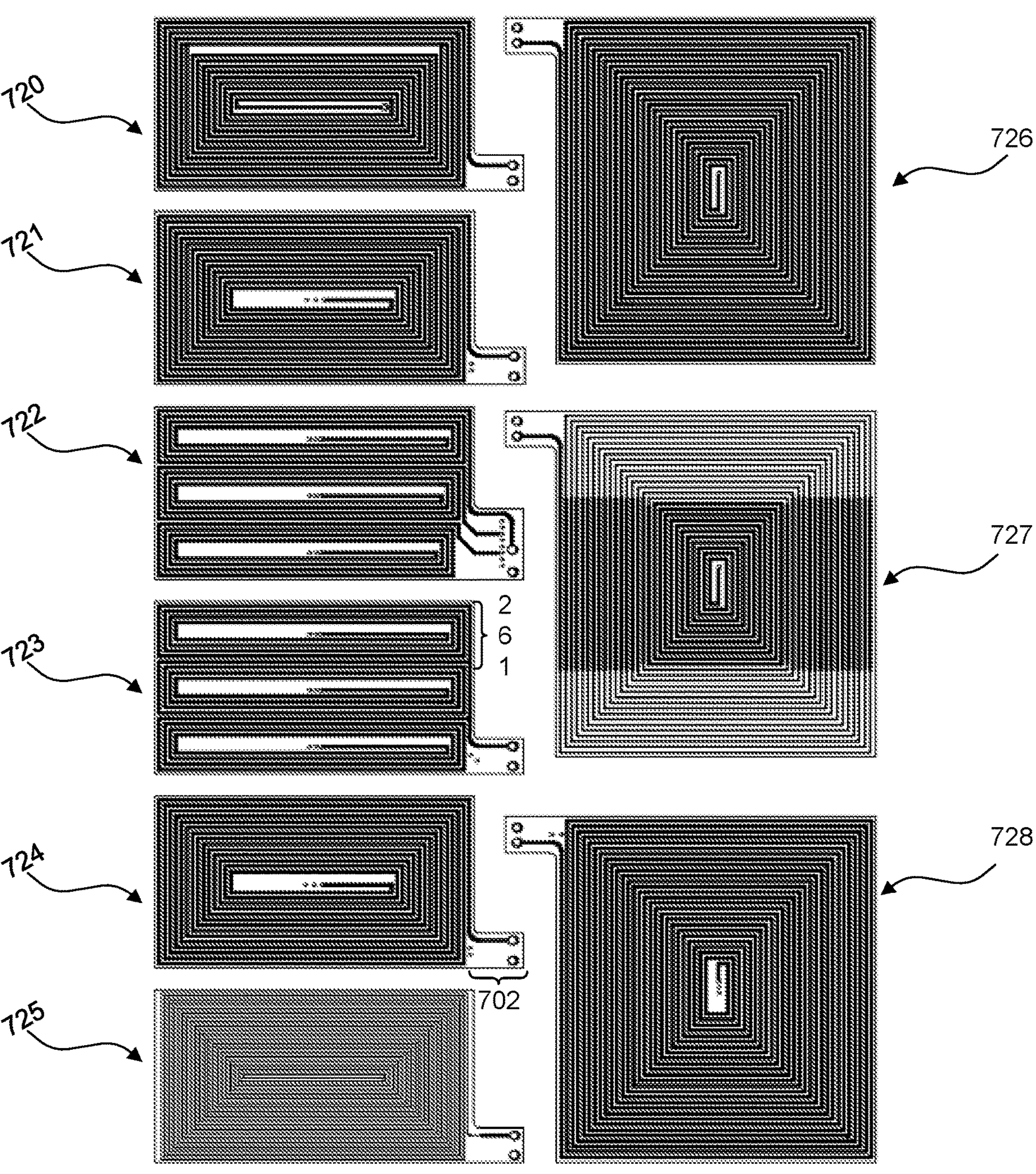

FIG. 52 a plurality of unwrapped coils in accordance with one embodiment.

Figure 53:
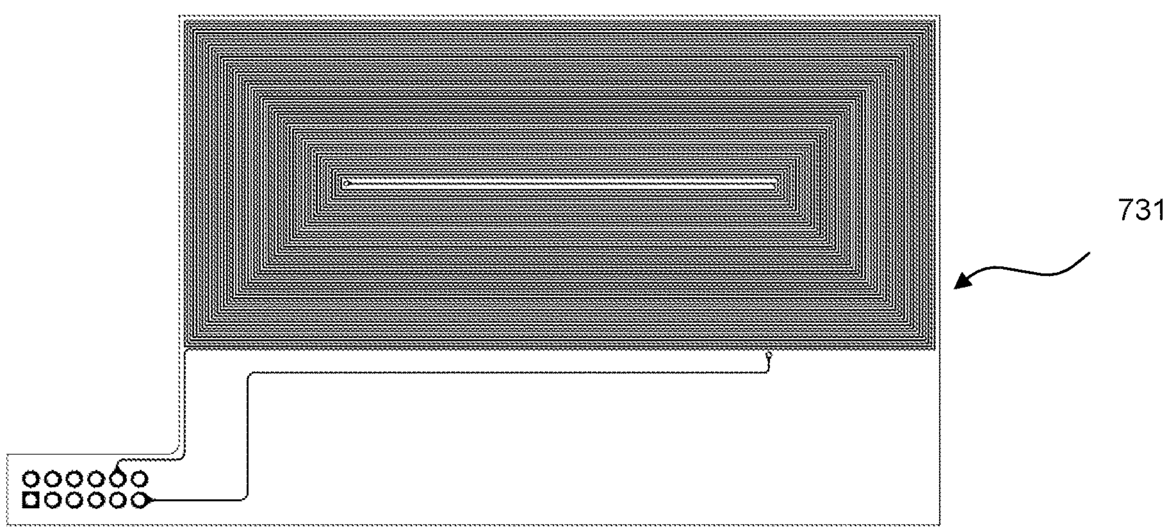

FIG. 53 is a diagram showing a two-phase coil that needs to be wrapped around 1.5 times to create the tubular shape

DETAIL DESCRIPTION

Figure 1:
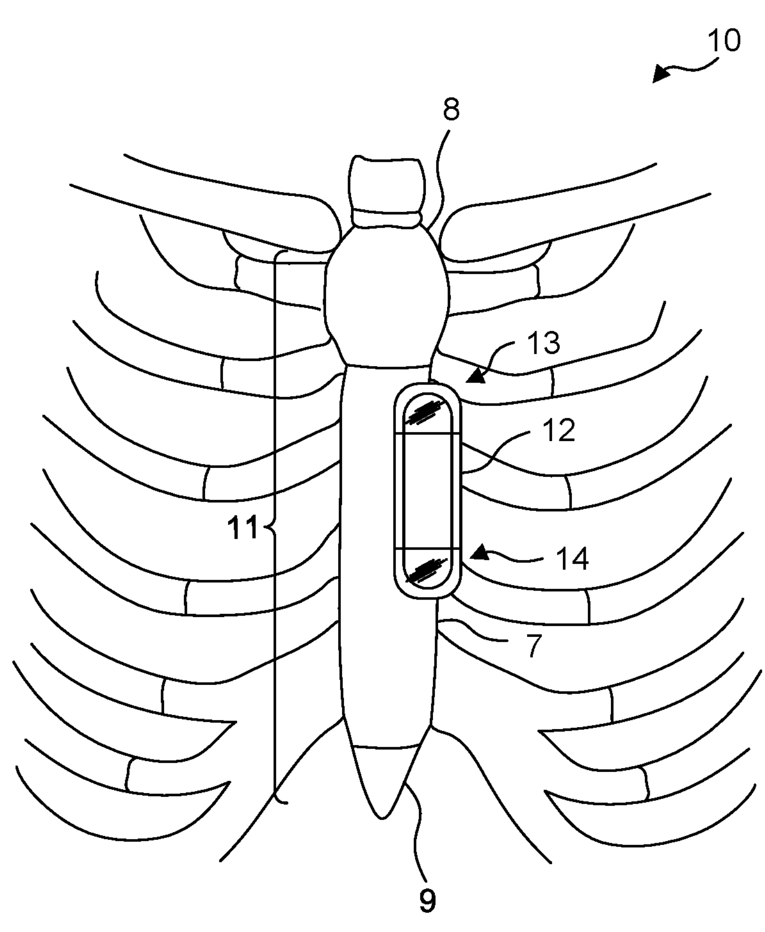
FIG. 1 is a diagram showing, by way of example, a subcutaneous P-wave centric insertable cardiac monitor (ICM) for long term electrocardiographic monitoring in accordance with one embodiment.

Long-term electrocardiographic and physiological monitoring over a period lasting up to several years in duration can be provided through a continuously-recording subcutaneous insertable cardiac monitor (ICM). FIG. 1 is a diagram showing, by way of example, a subcutaneous P-wave centric ICM 12 for long term electrocardiographic monitoring in accordance with one embodiment. The ICM 12 is implanted in the parasternal region 11 of a patient 10. The sensing circuitry and components, compression algorithms, and the physical layout of the electrodes are specifically optimized to capture electrical signals from the propagation of low amplitude, relatively low frequency content cardiac action potentials, particularly the P-waves generated during atrial activation. The position and placement of the ICM 12 coupled to engineering considerations that optimize the ICM's sensing circuitry, discussed infra, aid in demonstrating the P-wave clearly.

Implantation of a P-wave centric ICM 12 in the proper subcutaneous site facilitates the recording of high quality ECG data with a good delineation of the P-wave. In general, the ICM 12 is intended to be implanted anteriorly and be positioned axially and slightly to either the right or left of the sternal midline in the parasternal region 11 of the chest, or if sufficient subcutaneous fat exists, directly over the sternum. Optimally, the ICM 12 is implanted in a location left parasternally to bridge the left atrial appendage. However, either location to the right or left of the sternal midline is acceptable; placement of the device, if possible, should bridge the vertical height of the heart, which lies underneath the sternum 7, thereby placing the ICM 12 in close proximity to the anterior right atrium and the left atrial appendage that lie immediately beneath.

The ICM 12 is shaped to fit comfortably within the body under the skin and to conform to the contours of the patient's parasternal region 11 when implanted immediately to either side of the sternum 7, but could be implanted in other locations of the body. In most adults, the proximal end 13 of the ICM 12 is generally positioned below the manubrium 8 but, depending upon patient's vertical build, the ICM 12 may actually straddle the region over the manubrium 8. The distal end 14 of the ICM 12 generally extends towards the xiphoid process 9 and lower sternum but, depending upon the patient's build, may actually straddle the region over or under the xiphoid process 9, lower sternum and upper abdomen.

Although internal tissues, body structures, and tissue boundaries can adversely affect the current strength and signal fidelity of all body surface potentials, subsurface low amplitude cardiac action potentials, particularly P-wave signals with a normative amplitude of less than 0.25 millivolts (mV) and a normative duration of less than 120 milliseconds (ms), are most apt to be negatively impacted by these factors. The atria, which generate the P wave, are mostly located posteriorly within the thoracic cavity (with the exception of the anterior right atrium, right atrial appendage and left atrial appendage). The majority of the left atrium constitutes the portion of the heart furthest away from the surface of the skin on the chest and harbors the atrial tissue most likely to be the source of serious arrhythmias, like atrial fibrillation. Conversely, the ventricles, which generate larger amplitude signals, are located anteriorly as in the case of the anterior right ventricle and most of the anterior left ventricle situated relatively close to the skin surface of the central and left anterior chest. These factors, together with larger size and more powerful impulse generation from the ventricles, contribute to the relatively larger amplitudes of ventricular waveforms.

Nevertheless, as explained supra, both the P-wave and the R-wave are required for the physician to make a proper rhythm diagnosis from the dozens of arrhythmias that can occur. Yet, the quality of P-waves is more susceptible to weakening from distance and the intervening tissues and structures and from signal attenuation and signal processing than the high voltage waveforms associated with ventricular activation. The added value of avoiding further signal attenuation resulting from dermal impedance makes a subcutaneous P-wave centric ICM even more likely to match, or even outperform dermal ambulatory monitors designed to analogous engineering considerations and using similar sensing circuitry and components, compression algorithms, and physical layout of electrodes, such as described in U.S. Pat. No. 9,545,204, issued Jan. 17, 2017 to Bishay et al.; U.S. Pat. No. 9,730,593, issued Aug. 15, 2017 to Felix et al.; U.S. Pat. No. 9,700,227, issued Jul. 11, 2017 to Bishay et al.; U.S. Pat. No. 9,717,433, issued Aug. 1, 2017 to Felix et al.; and U.S. Pat. No. 9,615,763, issued Apr. 11, 2017 to Felix et al., the disclosures of which are incorporated by reference.

The ICM 12 can be implanted in the patient's chest using, for instance, a minimally invasive subcutaneous implantation instrument or other suitable surgical implement. The ICM 12 is positioned slightly to the right or left of midline, covering the center third of the chest, roughly between the second and sixth ribs, approximately spanning between the level of the manubrium 8 and the level of the xiphoid process 9 on the inferior border of the sternum 7, depending upon the vertical build of the patient 10.

During monitoring, the amplitude and strength of action potentials sensed by an ECG devices, including dermal ECG monitors and ICMs, can be affected to varying degrees by cardiac, cellular, extracellular, vector of current flow, and physical factors, like obesity, dermatitis, lung disease, large breasts, and high impedance skin, as can occur in dark-skinned individuals. Performing ECG sensing subcutaneously in the parasternal region 11 significantly improves the ability of the ICM 12 to counter some of the effects of these factors, particularly high skin impedance and impedance from subcutaneous fat. Thus, the ICM 12 exhibits superior performance when compared to conventional dermal ECG monitors to existing implantable loop recorders, ICMs, and other forms of implantable monitoring devices by virtue of its engineering and proven P-wave documentation above the skin, as discussed in W. M. Smith et al., "Comparison of diagnostic value using a small, single channel, P-wave centric sternal ECG monitoring patch with a standard 3-lead Holter system over 24 hours," Am. Heart J., March 2017; 185:67-73, the disclosure of which is incorporated by reference.

Moreover, the sternal midline implantation location in the parasternal region 11 allows the ICM's electrodes to record an ECG of optimal signal quality from a location immediately above the strongest signal-generating aspects of the atrial. Signal quality is improved further in part because cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the atrioventricular (AV) node. On the proximal end 13, the ECG electrodes of the ICM 12 are subcutaneously positioned with the upper or superior pole (ECG electrode) slightly to the right or left of the sternal midline in the region of the manubrium 8 and, on the distal end 14, the lower or inferior pole (ECG electrode) is similarly situated slightly to the right or left of the sternal midline in the region of the xiphoid process 9 and lower sternum 7. The ECG electrodes of the ICM 12 are placed primarily in a north-to-south orientation along the sternum 7 that corresponds to the north-to-south waveform vector exhibited during atrial activation. This orientation corresponds to the aVF lead used in a conventional 12-lead ECG that is used to sense positive or upright P-waves. In addition, the electrode spacing and the electrodes' shapes and surface areas mimic the electrodes used in the ICM's dermal cousin, designed as part of the optimal P-wave sensing electrode configuration, such as provided with the dermal ambulatory monitors cited supra.

Figure 2:
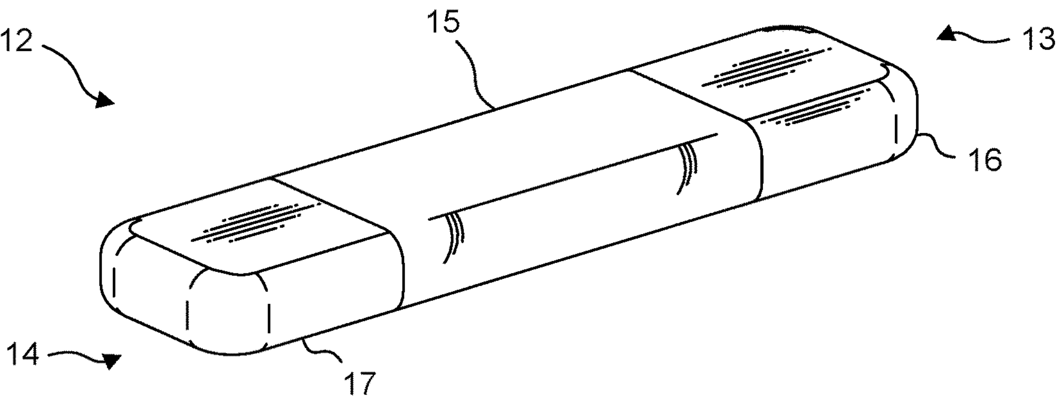
FIGS. 2 and 3 are respectively top and bottom perspective views showing the ICM of FIG. 1.
Figure 3:
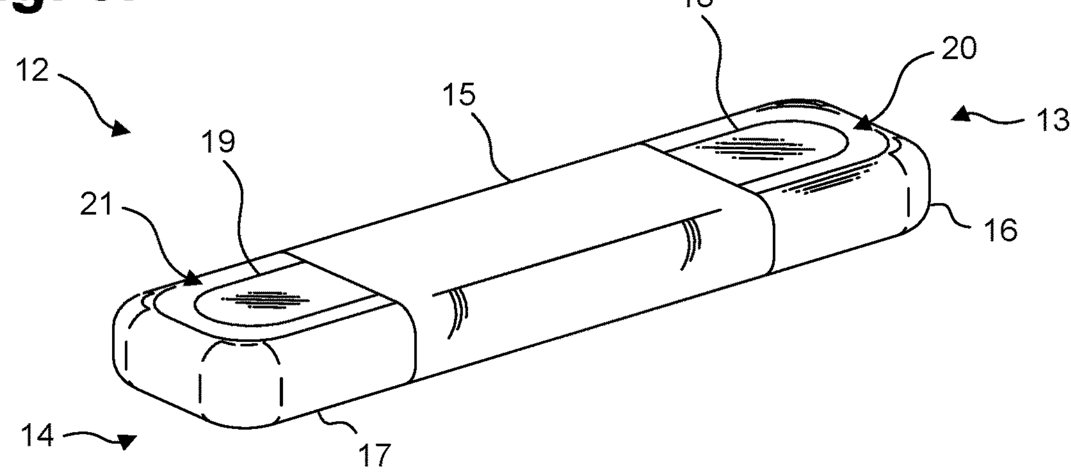

Despite the challenges faced in capturing low amplitude cardiac action potentials, the ICM 12 is able to operate effectively using only two electrodes that are strategically sized and placed in locations ideally suited to high fidelity P-wave signal acquisition. This approach has been shown to clinically outperform more typical multi-lead monitors because of the improved P-wave clarity, as discussed in W. M. Smith et al., cited supra. FIGS. 2 and 3 are respectively top and bottom perspective views showing the ICM 12 of FIG. 1. Physically, the ICM 12 is constructed with a hermetically sealed implantable housing 15 with at least one ECG electrode forming a superior pole on the proximal end 13 and at least one ECG electrode forming an inferior pole on the distal end 14.

When implanted, the housing 15 is oriented most cephalad. The housing 15 is constructed of titanium, stainless steel or other biocompatible material. The housing 15 contains the sensing, recordation and interfacing circuitry of the ICM 12, plus a long life battery. A wireless antenna is integrated into or within the housing 15 and can be positioned to wrap around the housing's internal periphery or location suited to signal reception. Other wireless antenna placement or integrations are possible, as further described below with reference to FIG. 18.

Physically, the ICM 12 has four ECG electrodes 16, 17, 18, 19. There could also be additional ECG electrodes, as discussed infra. The ECG electrodes include two ventral (or dorsal) ECG electrodes 18, 19 and two wraparound ECG electrodes 16, 17. One ventral ECG electrode 18 is formed on the proximal end 13 and one ventral ECG electrode 19 is formed on the distal end 14. One wraparound ECG electrode 16 is formed circumferentially about the proximal end 13 and one wraparound ECG electrode 17 is formed circumferentially about the distal end 14. Each wraparound ECG electrode 16, 17 is electrically insulated from its respective ventral ECG electrode 18, 19 by a periphery 20, 21.

The four ECG electrodes 16, 17, 18, 19 are programmatically controlled by a microcontroller through onboard firmware programming to enable a physician to choose from several different electrode configurations that vary the electrode surface areas, shapes, and inter-electrode spacing. The sensing circuitry can be programmed, either pre-implant or in situ, to use different combinations of the available ECG electrodes (and thereby changing electrode surface areas, shapes, and inter-electrode spacing), including pairing the two ventral ECG electrodes 16, 17, the two wraparound ECG electrodes 18, 19, or one ventral ECG electrode 16, 17 with one wraparound ECG electrode 18, 19 located on the opposite end of the housing 15. In addition, the periphery 20, 21 can be programmatically controlled to logically combine the wraparound ECG electrode 16, 17 on one end of the ICM 12 with its corresponding ventral ECG electrode 18, 19 to form a single virtual ECG electrode with larger surface area and shape. (Although electronically possible, the two ECG electrodes that are only on one end of the ICM 12, for instance, wraparound ECG electrode 16 and ventral ECG electrode 18, could be paired; however, the minimal inter-electrode spacing would likely yield a signal of poor fidelity in most situations.)

In a further embodiment, the housing 15 and contained circuitry can be provided as a standalone ICM core assembly to which a pair of compatible ECG electrodes can be operatively coupled to form a full implantable ICM device.

Figure 4:
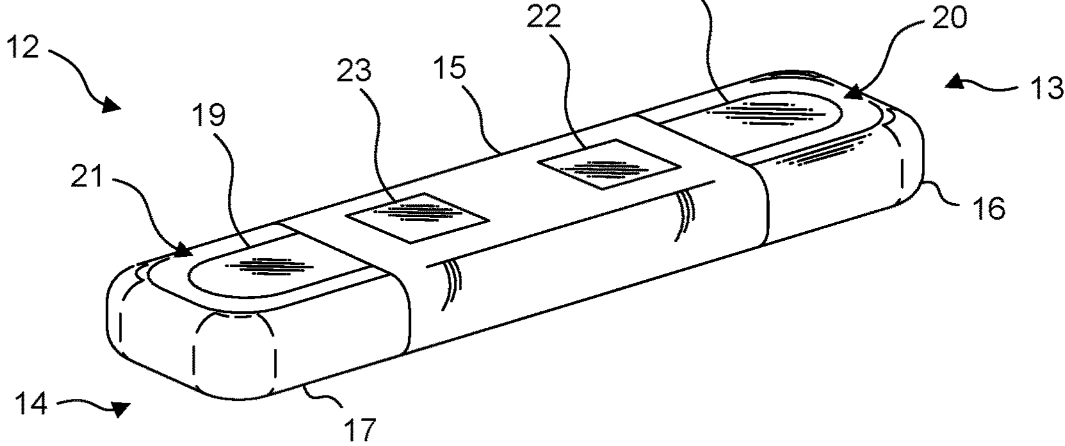
FIG. 4 is a bottom perspective view showing the ICM of FIG. 1 in accordance with a further embodiment.

Other ECG electrode configurations are possible. For instance, additional ECG electrodes can be provided to increase the number of possible electrode configurations, all of which are to ensure better P-wave resolution. FIG. 4 is a bottom perspective view showing the ICM 12 of FIG. 1 in accordance with a further embodiment. An additional pair of ventral ECG electrodes 22, 23 are included on the housing's ventral surface. These ventral ECG electrodes 22, 23 are spaced closer together than the ventral ECG electrodes 18, 19 on the ends of the housing 15 and a physician can thus choose to pair the two inner ventral ECG electrodes 22, 23 by themselves to allow for minimal electrode-to-electrode spacing, or with the other ECG electrodes 16, 17, 18, 19 to vary electrode surface areas, shapes, and inter-electrode spacing even further to explore optimal configurations to acquire the P-wave.

Figure 5:
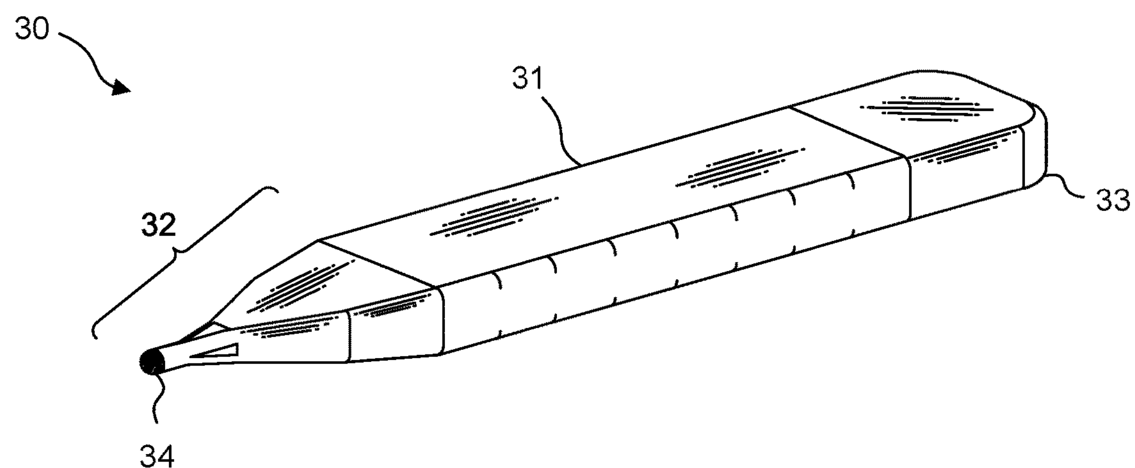
FIGS. 5 and 6 are respectively top and bottom perspective views showing an ICM in accordance with a still further embodiment.
Figure 6:
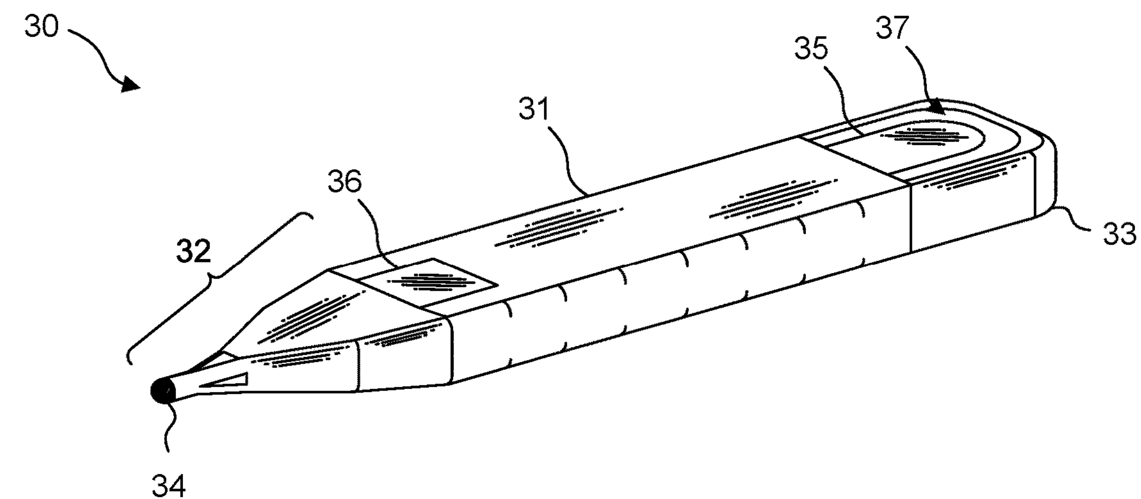

Other housing configurations of the ICM are possible. For instance, the housing of the ICM can be structured to enhance long term comfort and fitment, and to accommodate a larger long life battery or more circuitry or features, including physiologic sensors, to provide additional functionality. FIGS. 5 and 6 are respectively top and bottom perspective views showing an ICM 30 in accordance with a still further embodiment. The ICM 30 has a housing 31 with a tapered extension 32 that is terminated on the distal end with an electrode 34. On a proximal end, the housing 31 includes a pair of ECG electrodes electrically insulated by a periphery 37 that include a ventral ECG electrode 33 and a wraparound ECG electrode 34. In addition, a ventral ECG electrode 36 is oriented on the housing's distal end before the tapered extension 32. Still other housing structures and electrode configurations are possible.

In general, the basic electrode layout is sufficient to sense cardiac action potentials in a wide range of patients. Differences in thoracic tissue density and skeletal structure from patient to patient, though, can affect the ability of the sensing electrodes to efficaciously capture action potential signals, yet the degree to which signal acquisition is affected may not be apparent until after an ICM has been implanted and deployed, when the impacts of the patient's physical constitution and his patterns of mobility and physical movement on ICM monitoring can be fully assessed.

In further embodiments, the electrodes can be configured post-implant to allow the ICM to better adapt to a particular patient's physiology. For instance, electrode configurations having more than two sensing electrodes are possible. FIG. 7 is a plan view showing further electrode configurations. Referring first to FIG. 7(*a*), a single disc ECG electrode 40 could be bifurcated to form a pair of half-circle ECG electrodes 41, 42 that could be programmatically selected or combined to accommodate a particular patients ECG signal characteristics post-ICM implant. Referring next to FIG. 7(*b*), a single disc ECG electrode 45 could be divided into three sections, a pair of crescent-shaped ECG electrodes 46, 47 surrounding a central semicircular ECG electrode 48 that could similarly be programmatically selected or combined. Still other ECG electrode configurations are possible.

ECG monitoring and other functions performed by the ICM 12 are provided through a micro controlled architecture. FIG. 8 is a functional block diagram showing the P-wave focused component architecture of the circuitry 80 of the ICM 12 of FIG. 1. The circuitry 80 is powered through the long life battery 21 provided in the housing 15. Operation of the circuitry 80 of the ICM 12 is managed by a microcontroller 81, such as the EFM32 Tiny Gecko 32-bit microcontroller, manufactured by Silicon Laboratories Inc., Austin, TX. The microcontroller 81 has flexible energy management modes and includes a direct memory access controller and built-in analog-to-digital and digital-to-analog converters (ADC and DAC, respectively). The microcontroller 81 also includes a program memory unit containing internal flash memory (not shown) that is readable, writeable, and externally programmable.

The microcontroller 81 operates under modular micro program control as specified in firmware stored in the internal flash memory. The functionality and firmware modules relating to signal processing by the microcontroller 81 are further described infra with reference to FIG. 11. The microcontroller 81 draws power from the battery provided in the housing 15 and connects to the ECG front end circuit 83. In a further embodiment, the front end circuit 83 measures raw dermal electrical signals using a driven reference signal that eliminates common mode noise, as further described infra.

The circuitry 80 of the ICM 12 also includes a flash memory 82 external to the microcontroller 81, which the microcontroller 81 uses for continuously storing samples of ECG monitoring signal data and other physiology, such as respiratory rate, blood oxygen saturation level ($SpO_2$), blood pressure, temperature sensor, and physical activity, and device and related information. The flash memory 82 also draws power from the battery provided in the housing 15. Data is stored in a serial flash memory circuit, which supports read, erase and program operations over a communications bus. The flash memory 82 enables the microcontroller 81 to store digitized ECG data. The communications bus further enables the flash memory 82 to be directly accessed wirelessly through a transceiver 85 coupled to an antenna 17 built into (or provided with) the housing 15, as further described infra with reference to FIG. 9. The transceiver 85 can be used for wirelessly interfacing over Bluetooth or other types of wireless technologies for exchanging data over a short distance with a paired mobile device, including smartphones and smart watches, that are designed to communicate over a public communications infrastructure, such as a cellular communications network, and, in a further embodiment, other wearable (or implantable) physiology monitors, such as activity trackers worn on the wrist or body. Other types of device pairings are possible, including with a desktop computer or purpose-built bedside monitor. The transceiver 85 can be used to offload stored ECG monitoring data and other physiology data and information and for device firmware reprogramming. In a further embodiment, the flash memory 82 can be accessed through an inductive coupling (not shown).

Figure 11:
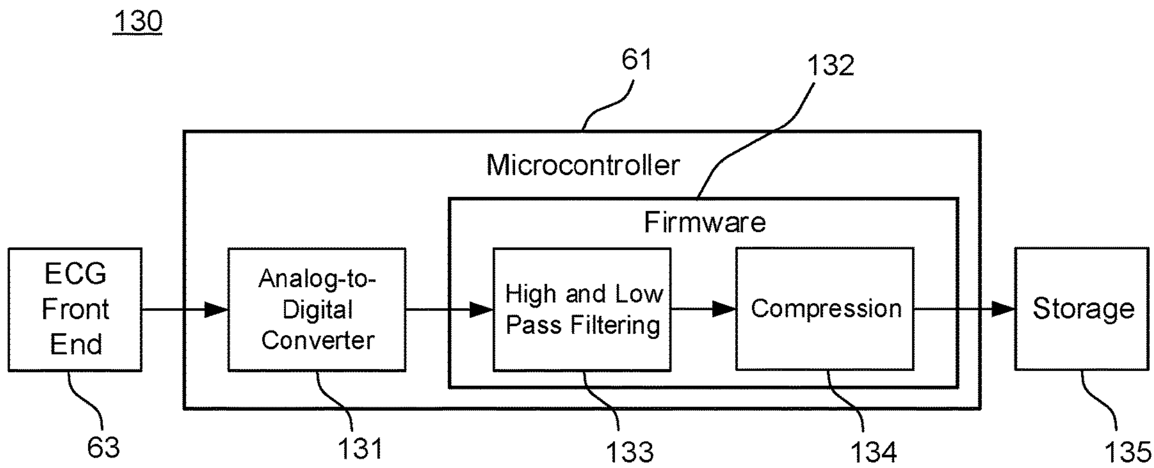
FIG. 11 is a functional block diagram showing the signal processing functionality of the microcontroller.

The microcontroller 81 includes functionality that enables the acquisition of samples of analog ECG signals, which are converted into a digital representation, as further described infra with reference to FIG. 11. In one mode, the microcontroller 81 implements a loop recorder feature that will acquire, sample, digitize, signal process, and store digitized ECG data into available storage locations in the flash memory 82 until all memory storage locations are filled, after which existing stored digitized ECG data will either be overwritten through a sliding window protocol, albeit at the cost of potentially losing the stored data that was overwritten, if not previously downloaded, or transmitted wirelessly to an external receiver to unburden the flash memory. In another mode, the stored digitized ECG data can be maintained permanently until downloaded or erased to restore memory capacity. Data download or erasure can also occur before all storage locations are filled, which would free up memory space sooner, albeit at the cost of possibly interrupting monitoring while downloading or erasure is performed. Still other modes of data storage and capacity recovery are possible.

The circuitry 80 of the ICM 12 can include functionality to programmatically select pairings of sensing electrodes when the ICM 12 is furnished with three or more electrodes. In a further embodiment, multiple sensing electrodes could be provided on the ICM 12 to provide a physician the option of fine-tuning the sensing dipole (or tripole or multipole) in situ by parking active electrodes and designating any remaining electrodes inert. The pairing selection can be made remotely through an inductive coupling or by the transceiver 85 via, for instance, a paired mobile device, as further described infra. Thus, the sensing electrode configuration, including number of electrodes, electrode-to-electrode spacing, and electrode size, shape, surface area, and placement, can be modified at any time during the implantation of the ICM 12.

In a further embodiment, the circuitry 80 of the ICM 12 can include an actigraphy sensor 84 implemented as a 3-axis accelerometer. The accelerometer may be configured to generate interrupt signals to the microcontroller 81 by independent initial wake up and free fall events, as well as by device position. In addition, the actigraphy provided by the accelerometer can be used during post-monitoring analysis to correct the orientation of the ICM 12 if, for instance, the ICM 12 has been inadvertently implanted upside down, that is, with the ICM's housing oriented caudally, as well as for other event occurrence analyses.

In a still further embodiment, the circuitry 80 of the ICM 12 can include one or more physiology sensors. For instance, a physiology sensor can be provided as part of the circuitry 80 of the ICM 12, or can be provided on the electrode assembly 14 with communication with the microcontroller 81 provided through a circuit trace. The physiology sensor can include a $SpO_2$ sensor, blood pressure sensor, temperature sensor, respiratory rate sensor, glucose sensor, airflow sensor, volumetric pressure sensing, or other types of sensor or telemetric input sources.

In a yet further embodiment, firmware with programming instructions, including machine learning and other forms of artificial intelligence-originated instructions, can be downloaded into the microcontroller's internal flash memory. The firmware can include heuristics to signal patient and physician with alerts over health conditions or arrhythmias of selected medical concern, such as where a heart pattern particular to the patient is identified and the ICM 12 is thereby reprogrammed to watch for a reoccurrence of that pattern, after which an alert will be generated and sent to the physician (or other caregiver) through the transceiver 85 via, for instance, a paired mobile device. Similarly, the firmware can include heuristics that can be downloaded to the ICM 12 to actively identify or narrow down a pattern (or even the underlying cause) of sporadic cardiac conditions, for instance, atrial tachycardia (AT), atrial fibrillation (AF), atrial flutter (AFL), AV node reciprocating tachycardia, ventricular tachycardia (VT), sinus bradycardia, asystole, complete heart block, and other cardiac arrhythmias, again, after which an alert will be generated and sent to the physician (or other caregiver) through the transceiver 85. For instance, an alert that includes a compressed ECG digitized sample can also be wirelessly transmitted by the ICM 12 upon the triggering of a preset condition, such as an abnormally low heart rate in excess of 170 beats per minute (bpm), an abnormally low heart rate falling below 30 bpm, or AF detected by onboard analysis of RR interval variability by the microcontroller 61. Finally, a similar methodology of creating firmware programming tailored to the monitoring and medical diagnostic needs of a specific patient (or patient group or general population) can be used for other conditions or symptoms, such as syncope, palpitations, dizziness and giddiness, unspecified convulsions, abnormal ECG, transient cerebral ischemic attacks and related syndromes, cerebral infarction, occlusion and stenosis of pre-cerebral and cerebral arteries not resulting in cerebral infarction personal history of transient ischemic attack, and cerebral infarction without residual deficits, to trigger an alert and involve the physician or initiate automated analysis and follow up back at the patient's clinic. Finally, in a still further embodiment, the circuitry 80 of the ICM 12 can accommodate patient-interfaceable components, including an external tactile feedback device (not shown) that wirelessly interfaces to the ICM 12 through the transceiver 85. A patient 10 can press the external tactile feedback device to mark events, such as a syncope episode, or to perform other functions. The circuitry 80 can also accommodate triggering an external buzzer 67, such as a speaker, magnetic resonator or piezoelectric buzzer, implemented as part of the external tactile feedback device or as a separate wirelessly-interfaceable component. The buzzer 67 can be used by the microcontroller 81 to indirectly output feedback to a patient 10, such as a low battery or other error condition or warning. Still other components, provided as either part of the circuitry 80 of the ICM 12 or as external wirelessly-interfaceable devices, are possible.

In a further embodiment, the ECG front end circuit 83 of the ICM 12 measures raw dermal electrical signals using a driven reference signal, such as described in U.S. Pat. Nos. 9,700,227, 9,717,433, and 9,615,763, cited supra. The driven reference signal effectively reduces common mode noise, power supply noise and system noise, which is critical to preserving the characteristics of low amplitude cardiac action potentials, especially the P wave signals originating from the atria.

The ECG front end circuit 83 is organized into a passive input filter stage, a unity gain voltage follower stage, a passive high pass filtering stage, a voltage amplification and active filtering stage, and an anti-aliasing passive filter stage, plus a reference generator. The passive input filter stage passively shifts the frequency response poles downward to counter the high electrode impedance from the patient on the signal lead and reference lead, which reduces high frequency noise. The unity gain voltage follower stage allows the circuit to accommodate a very high input impedance, so as not to disrupt the subcutaneous potentials or the filtering effect of the previous stage. The passive high pass filtering stage includes a high pass filter that removes baseline wander and any offset generated from the previous stage. As necessary, the voltage amplification and active filtering stage amplifies or de-amplifies (or allows to pass-through) the voltage of the input signal, while applying a low pass filter. The anti-aliasing passive filter stage 75 provides an anti-aliasing low pass filter. The reference generator drives a driven reference signal containing power supply noise and system noise to the reference lead and is connected directly to the patient, thereby avoiding the thermal noise of the protection resistor that is included as part of the protection circuit 72.

Figure 13:
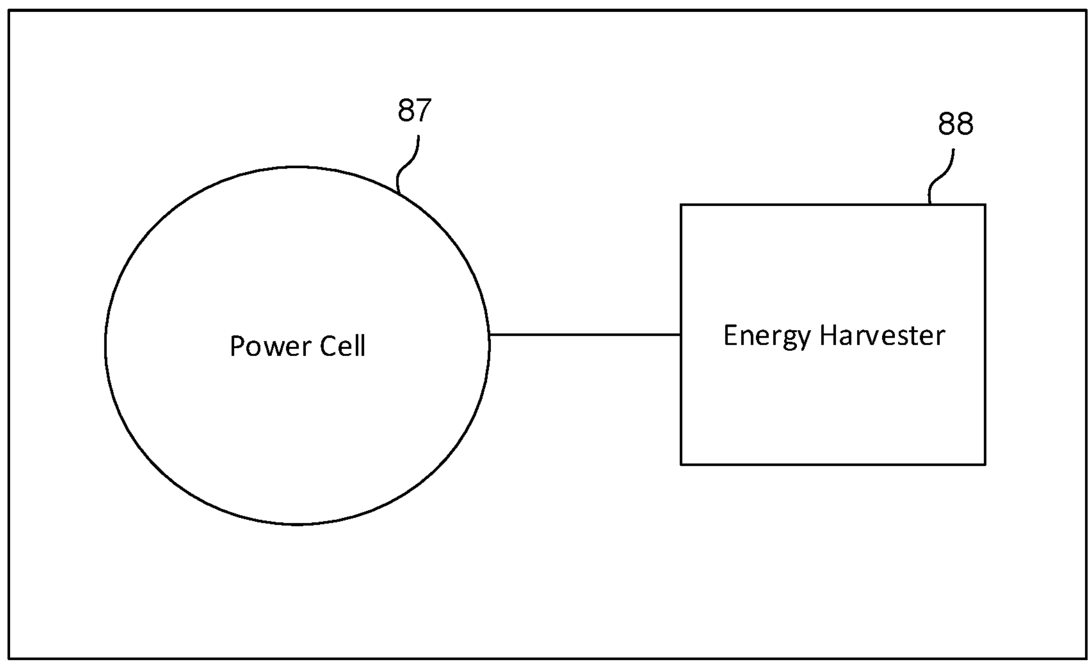
FIG. 13 is a diagram showing a power source of the ICM of FIG. 8 in accordance with one embodiment.

The ICM circuitry 80 further includes a power source 86 that is interfaced to other components of the circuitry 80 and powers those components. FIG. 13 is a diagram showing a power source 86 of the ICM 12 in accordance with one embodiment. The power source 86 includes a rechargeable power cell 87 and an energy harvesting module 88, which generates electrical energy based on input from an environment outside of the implantable housing, including when the implantable housing has been implanted within the patient 10. In one embodiment, the rechargeable power cell 87 can be a lithium-titanate battery, which recharges at a significantly faster rate due to an increased surface area at the anode (when compared to many other types of batteries). Other kinds of the rechargeable power cells 87 are also possible.

Figure 14:
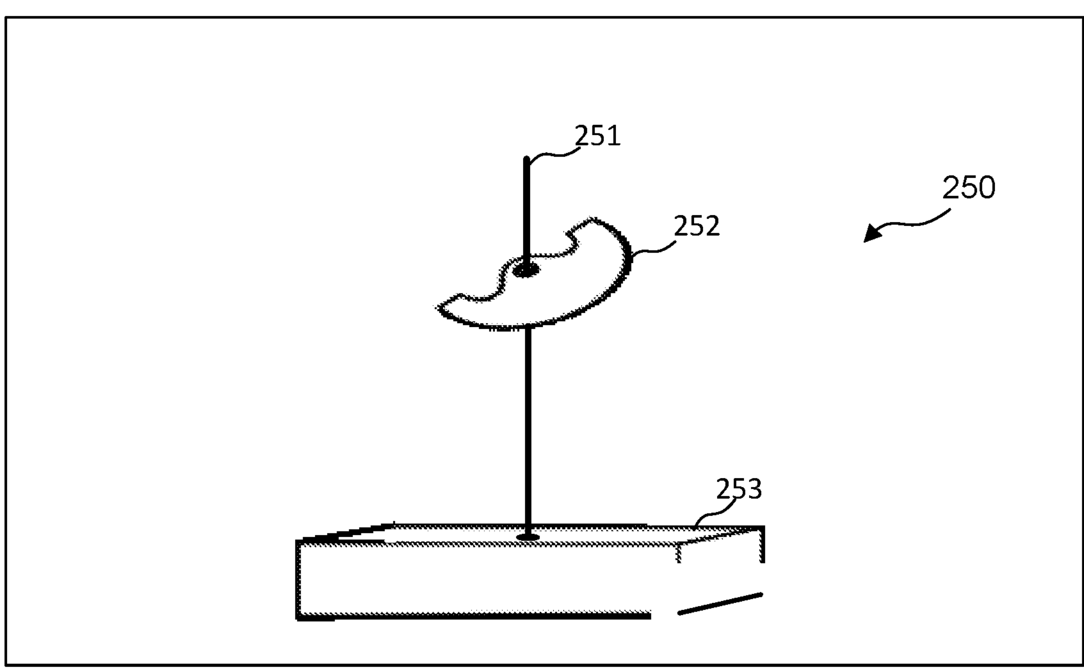
FIG. 14 is a diagram showing the energy harvesting module of FIG. 13 with a configuration to harvest kinetic energy in accordance with one embodiment.

While in the description below beginning with reference to FIG. 14 the energy harvesting module 88 is described as having a single energy-generating mechanism, in a further embodiment, a single energy harvesting module could combine multiple energy harvesting mechanisms (such as those described with reference to FIGS. 14-18). Further while particular embodiments of the energy harvesting module 88 are described with reference to FIGS. 14-26, other embodiments of the energy harvesting module 88 are also possible. In addition, while the power source 86 is shown as an integrated module, in a further embodiment, different components could be distributed throughout the ICM 12. Likewise, different components of the energy harvesting module 88 could be distributed throughout the ICM 12.

The energy harvesting module 88 can provide the harvested energy to the rechargeable power cell 87, recharging the power cell 87 and allowing the power cell 87 to power other components of the circuitry 80. In a further embodiment, the power cell 87 can be absent from the power source 86, and the electrical energy generated by the energy harvesting module 88 is the only electrical energy powering other components of the circuitry 87. Thus, the energy harvesting is either indirectly, via the power cell 87, or directly, interfaced to other components of the circuitry 80, providing power for those components of the circuitry 80.

Figure 9:
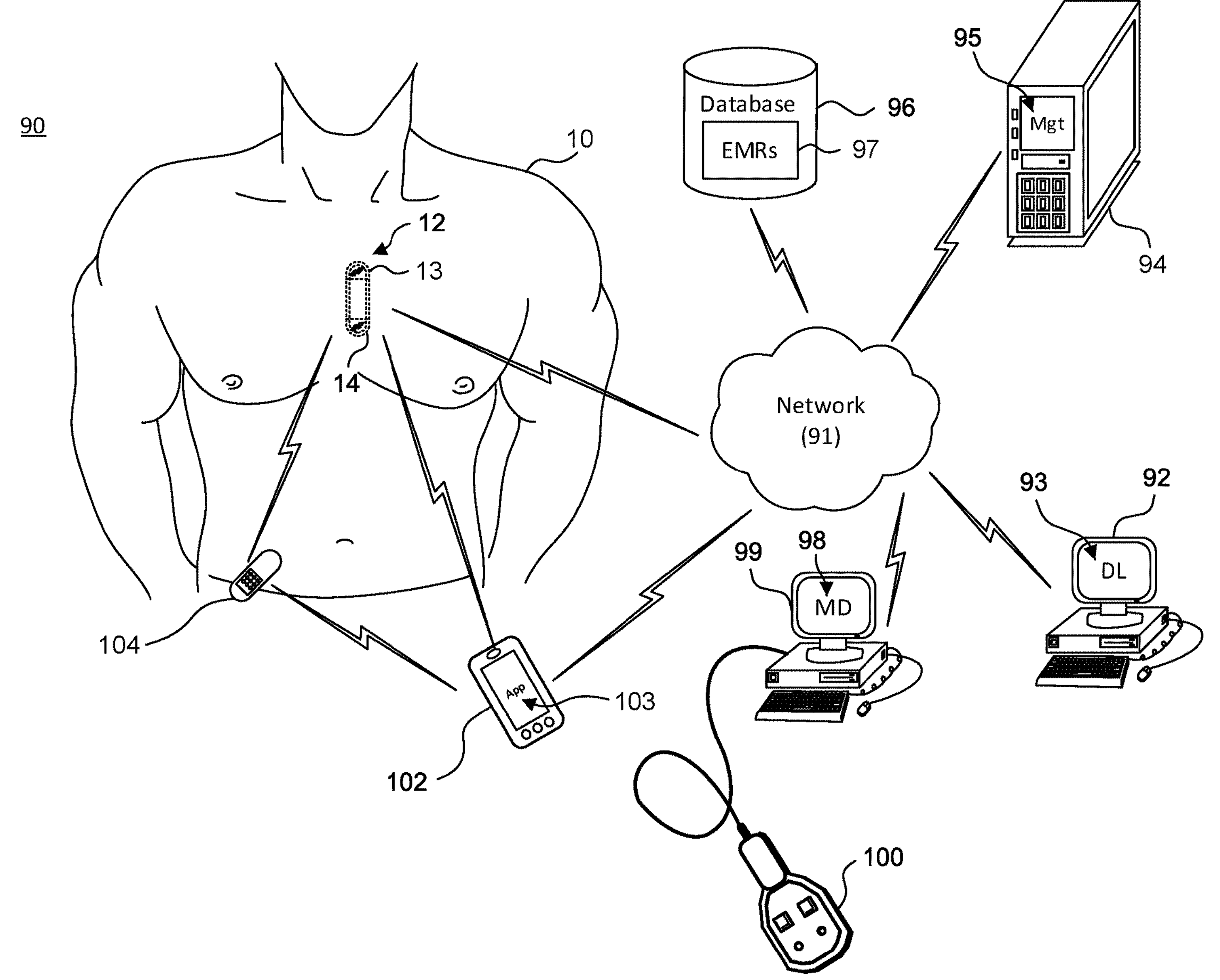
FIG. 9 is a functional block diagram showing a system for wirelessly interfacing with an ICM in accordance with one embodiment.

When operated standalone, the recording circuitry of the ICM 12 senses and records the patient's ECG data into an onboard memory. The ICM 12 can interoperate with other devices wirelessly through the transceiver 85. FIG. 9 is a functional block diagram showing a system 90 for wirelessly interfacing with with and recharging an ICM 12 in accordance with one embodiment. The ICM 12 is designed for long-term electrocardiographic and physiological monitoring lasting up to several years in duration. During that time, stored data ECG monitoring data and other physiology and information will need to be offloaded and the ICM's firmware may need to be reprogrammed, and the transceiver 85 enables the ICM 12 to communicate with external devices to facilitate these functions.

In one embodiment, the ICM 12 can be wirelessly connected to a download station 92 executing data link software ("DL") 93 that permits the secure remote retrieval of stored ECG monitoring data, execution of diagnostics on or programming of the ICM 12, or performance of other functions. The ICM 12 connects to the download station 92 over a wireless network 91 via the transceiver 85. In turn, the download station 92 executes the data link software 93 or similar program that wirelessly interacts with the ICM 12 to retrieve the stored ECG monitoring data or perform other function. The download station 92 could be a server, personal computer, tablet or handheld computer, smart mobile device, or purpose-built programmer designed specific to the task of interfacing with a ICM 12, such as described below with reference to FIG. 19. Still other forms of download station 92 are possible.

Figure 12:
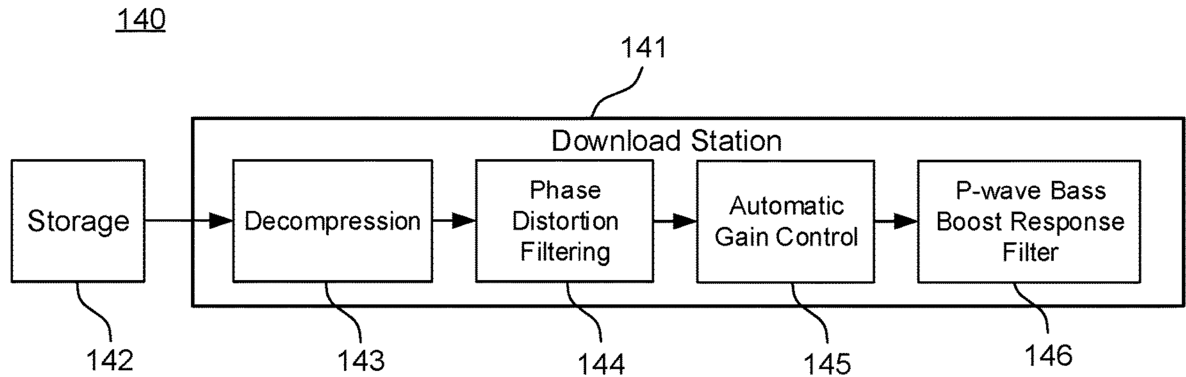
FIG. 12 is a functional block diagram showing the operations performed by the download station.

Upon retrieving stored ECG monitoring data from a ICM 12, middleware (not shown) executing on the download station 92 first operates on the retrieved data to adjust the ECG capture quality, as necessary, and to convert the retrieved data into a format suitable for use by third party post-monitoring analysis software, as further described infra with reference to FIG. 12. The formatted data can then be retrieved from the download station 92. The middleware could alternatively be executed by a separate device other than the download station 92.

A client-server model could be used to employ a server 94 to remotely interface with the download station 92 over the network 91 and retrieve the formatted data or other information. The server 94 executes a patient management program 95 ("Mgt") or similar application that stores the retrieved formatted data, recorded physiology, and other information in a secure database 96 cataloged in that patient's electronic medical records (EMRs) 97, along with tracking and correlating patient symptoms. In addition, the patient management program 95 could manage a subscription service that authorizes an ICM 12 to operate for a set period of time or under pre-defined operational parameters.

The patient management program 95, or other trusted application, also maintains and safeguards the secure database 96 to limit access to patient EMRs 97 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 96.

Physician and other authorized healthcare personnel are able to securely access the retrieved formatted data and other information stored in the EMRs 97 in the secure database 96 by executing an application program ("MD") 98, such as a post-monitoring ECG analysis program, on a personal computer 99 or other connectable computing device, and, through the application program 98, coordinate access to his patient's EMRs 97 with the patient management program 95 and perform other functions. The application program 98 can include the capability to actively or interactively diagnose or narrow down the underlying cause of sporadic cardiac conditions, for instance, atrial tachycardia (AT), AF, atrial flutter, AV node reciprocating tachycardia, ventricular tachycardia (VT), sinus bradycardia, asystole, complete heart block, and other cardiac arrhythmias. Other diagnoses are possible.

In a further embodiment, RR interval data can be extracted from the retrieved formatted data and be presented to physicians in a format that includes views of relevant near field and far field ECG data, which together provide contextual information that improves diagnostic accuracy, such as described in U.S. Pat. No. 9,408,551, issued Aug. 9, 2016 to Bardy et al., the disclosure of which is incorporated by reference. Both near field and far field ECG data views are temporally keyed to an extended duration RR interval data view. The durations of the classical "pinpoint" view, the pre- and post-event "intermediate" view, and the RR interval plot are flexible and adjustable. Thus, the pinpoint "snapshot" and intermediate views of ECG data with the extended term RR interval data allow a physician to comparatively view heart rate context and patterns of behavior prior to and after a clinically meaningful arrhythmia, patient concern or other indicia, thereby enhancing diagnostic specificity of cardiac rhythm disorders and providing physiological context to improve diagnostic ability. Similarly, the data wirelessly offloaded by the ICM can also be used to create a diagnostic composite plot of cardiac data, as further described in U.S. Pat. No. 9,408,551, issued Aug. 9, 2016, the disclosure of which is incorporated by reference. As the amount of data necessary to construct an RR interval plot can be as large as 0.25 megabyte, the energy provided by the energy harvesting module 88 becomes critical for continuous offloading of the collected data at rates high enough to enable such processing.

As a result, with the assistance of the server 94, a complete end-to-end closed loop of patient care can be provided, with the ICM 12 providing long-term ECG and physiology monitoring and data reporting, the patient management program 95 managing ECG and physiology data retrieval and patient symptom tracking and correlation, the application program 98 empowering physicians with the ability to effectively identify the underlying cause of sporadic cardiac conditions, particularly cardiac rhythm disorders, and the ICM 12 again facilitating patient following upon diagnosis and throughout treatment.

In a further embodiment, the ICM 12 can interoperate wirelessly with other physiology monitors and activity sensors 104, whether implanted or dermal, such as activity trackers worn on the wrist or body, and with mobile devices 102, including smartphones and smart watches, that are designed to communicate over a public communications infrastructure, such as a cellular communications network. Wearable physiology monitors and activity sensors 104 encompass a wide range of wirelessly interconnectable devices that measure or monitor a patient's physiological data, such as heart rate, temperature, blood pressure, respiratory rate, blood pressure, blood sugar (with appropriate subcutaneous probe), oxygen saturation, minute ventilation, and so on; physical states, such as movement, sleep, footsteps, and the like; and performance, including calories burned or estimated blood glucose level.

The physiology sensors in non-wearable mobile devices 102, particularly smartphones, are generally not meant for continuous tracking and do not provide medically precise and actionable data sufficient for a physician to prescribe a surgical, catheter or serious drug intervention; such data can be considered screening information that something may be wrong, but not data that provides the highly precise information that may allow for a surgery, such as implantation of a pacemaker for heart block or a defibrillator for ventricular tachycardia, or the application of serious medications, like blood thinners for atrial fibrillation or a cardiac ablation procedure. Such devices, like smartphones, are better suited to pre- and post-exercise monitoring or as devices that can provide a signal that something is wrong, but not in the sufficient detail and FDA approved, legally meaningful validation to allow for medical action. Conversely, medically actionable wearable sensors and devices sometimes provide continuous recording for relatively short time periods, up to 80 days, but do not span years and, further, must be paired with a smartphone or computer to offload and evaluate the recorded data, especially if the data is of urgent concern.

Wearable physiology monitors and activity sensors 104, also known as "activity monitors," and to a lesser extent, "fitness" sensor-equipped mobile devices 102, can trace their life-tracking origins to ambulatory devices used within the medical community to sense and record traditional medical physiology that could be useful to a physician in arriving at a patient diagnosis or clinical trajectory, as well as from outside the medical community, from, for instance, sports or lifestyle product companies who seek to educate and assist individuals with self-quantifying interests. Data is typically tracked by the wearable physiology monitors or activity sensors 104 and mobile device 102 for only the personal use of the wearer. The physiological monitoring is strictly informational, even where a device originated within the medical community, and the data is generally not time-correlated to physician-supervised monitoring. Importantly, medically-significant events, such as cardiac rhythm disorders, including tachyarrhythmias, like ventricular tachycardia or atrial fibrillation, and bradyarrhythmias, like heart block, while potentially detectable with the appropriate diagnostic heuristics, are neither identified nor acted upon by the wearable physiology monitors and activity sensors 104 and the mobile device 102.

Frequently, wearable physiology monitors and activity sensors 104 are capable of wirelessly interfacing with mobile devices 102, particularly smart mobile devices, including so-called "smartphones" and "smart watches," as well as with personal computers and tablet or handheld computers, to download monitoring data either in real-time or in batches. The wireless interfacing of such activity monitors is generally achieved using transceivers that provide low-power, short-range wireless communications, such as Bluetooth, although some wearable physiology monitors and activity sensors 104, like their mobile device cohorts, have transceivers that provide true wireless communications services, including 4G or better mobile telecommunications, over a telecommunications network. Other types of wireless and wired interfacing are possible.

In a further embodiment, where the wearable physiology monitors and activity sensors 104 are paired with a mobile device 102, the mobile device 102 executes an application ("App") 103 that can retrieve the data collected by the wearable physiology monitor and activity sensor 104 and evaluate the data to generate information of interest to the wearer, such as an estimation of the effectiveness of the wearer's exercise efforts. Where the wearable physiology monitors and activity sensors 104 has sufficient onboard computational resources, the activity monitor itself executes an app without the need to relay data to a mobile device 102. The app can include or be supplemented by downloadable programming instructions, including machine learning and other forms of artificial intelligence-originated instructions. The app can include heuristics to signal patient and physician with alerts over health conditions or arrhythmias of selected medical concern, such as where a heart pattern particular to the patient is identified and the mobile device 102, in collaboration with the ICM 12, is thereby reprogrammed to watch for a reoccurrence of that pattern, after which an alert will be generated and sent to the physician (or other caregiver). Similarly, the app can include heuristics that can actively identify or narrow down a pattern (or even the underlying cause) of sporadic cardiac conditions, for instance, atrial tachycardia (AT), atrial fibrillation (AF), atrial flutter (AFL), AV node reciprocating tachycardia, ventricular tachycardia (VT), sinus bradycardia, asystole, complete heart block, and other cardiac arrhythmias, again, after which an alert will be generated and sent to the physician (or other caregiver). For instance, an alert that includes a compressed ECG digitized sample can also be wirelessly transmitted by the app upon the triggering of a preset condition, such as an abnormally low heart rate in excess of 170 beats per minute (bpm), an abnormally low heart rate falling below 30 bpm, or AF detected by onboard analysis of RR interval variability by the app. Finally, a similar methodology of creating app programming tailored to the monitoring and medical diagnostic needs of a specific patient (or patient group or general population) can be used for other conditions or symptoms, such as syncope, palpitations, dizziness and giddiness, unspecified convulsions, abnormal ECG, transient cerebral ischemic attacks and related syndromes, cerebral infarction, occlusion and stenosis of pre-cerebral and cerebral arteries not resulting in cerebral infarction personal history of transient ischemic attack, and cerebral infarction without residual deficits, to trigger an alert and involve the physician or initiate automated analysis and follow up back at the patient's clinic. Still other activity monitor and mobile device functions on the collected data are possible.

In a yet further embodiment, a wearable physiology monitor, activity sensor 104, or mobile device 102 worn or held by the patient 10, or otherwise be used proximal to the patient's body, can be used to first obtain and then work collaboratively with the more definitive and capable ICM 12 to enable the collection of physiology by the ICM 12 before, during, and after potentially medically-significant events. The wearable physiology monitor, activity sensor 104, or mobile device 102 must be capable of sensing cardiac activity, particularly heart rate or rhythm, or other types of physiology or measures, either directly or upon review of relayed data. Where the wearable physiology monitor or activity sensor 104 is paired with a mobile device 102, the mobile device 102 serves as a relay device to trigger a medical alert upon detecting potentially medically-significant events in the data provided by the paired activity monitor, such as cardiac rhythm disorders, including tachyarrhythmias and bradyarrhythmias. Finally, if the wearable physiology monitor or activity sensor 104 has sufficient onboard computational resources and also is equipped with a wireless communications services transceiver, the wearable physiology monitor or activity sensor 104 effectively becomes the mobile device and executes an application (not shown) that will trigger the medical alert directly. Still other configurations of the detection app are possible.

In a still further embodiment, the monitoring data recorded by the ICM 12 can be uploaded directly into the patient's EMRs 97, either by using a mobile device 102 as a conduit for communications with the secure database 96 via the server 94, or directly to the server 94, if the ICM 12 is appropriately equipped with a wireless transceiver 85 (shown with reference to FIG. 8) or similar external data communications interface. As described below, the wireless data offloaded from the ICM 12 can be used in a variety of ways, with the use requiring a frequent wireless transmission of large collected data sets, including full disclosure HRV. Such frequent transmission of large data sets is made possible by the presence of the energy harvesting module 88 described below. Further, the availability of the energy harvesting module 88 allows to increase the amount of power used by the wireless transceiver 85 to allow fast and efficient data transfer rates through subcutaneous fat of the patient 10. The increased amount of power used by the wireless transceiver 85 can be pre-set prior to the implantation of the ICM 12, or done following the implantation. For example, the amount of power used by the wireless transceiver 85 can be wirelessly adjusted by an external programmer (such as upon the rates of data transfer from the ICM 12 being unsatisfactory), or done by the microcontroller 81 upon detection that the rates of data transfer are below a threshold level.

Thus, the data recorded by the ICM 12 would directly feed into the patient's EMRs 97, thereby allowing the data to be made certifiable for immediate use by a physician or authorized healthcare provider. No intermediate steps would be necessary when going from subcutaneously sensing cardiac electric signals and collecting the patient's physiology using a ICM 12 to presenting that recorded data to a physician or healthcare provider for medical diagnosis and care. The direct feeding of data from the ICM 12 to the EMRs 97 clearly establishes the relationship of the data, as recorded by the ICM 12, to the patient 10 that the physician is seeing and appropriately identifies any potentially medically-significant event recorded in the data as originating in the patient 10 and nobody else. Based on the monitoring data, physicians and healthcare providers can rely on the data as certifiable and can directly proceed with determining the 1 appropriate course of treatment for the patient 10, including undertaking further medical interventions as appropriate.

In a yet further embodiment, the server 94 can evaluate the recorded data, as fed into the patient's EMRs 97, to refer the patient 10 for medical care to a general practice physician or medical specialist, for instance, a cardiac electrophysiologist referral from a cardiologist when the recorded data indicates an event of sufficient potential severity to warrant the possible implantation of a pacemaker for heart block or a defibrillator for ventricular tachycardia. Other uses of the data recorded by the ICM 12 are possible. For instance, a patient 10 who has previously suffered heart failure is particularly susceptible to ventricular tachycardia following a period of exercise or strenuous physical activity. A wearable sensor 104 or device 102 that includes a heart rate monitor would be able to timely detect an irregularity in heart rhythm. The application executed by the sensor 104 or device 102 allows those devices to take action by triggering the dispatch of a ICM 12 to the patient 10, even though the data recorded by the sensor 104 or device 102 is itself generally medically-insufficient for purposes of diagnosis and care. Thus, rather than passively recording patient data, the sensor 104 or device 102 takes on an active role in initiating the provisioning of medical care to the patient 10 and starts a cascade of appropriate medical interventions under the tutelage of and followed by physicians and trained healthcare professionals.

In a still further embodiment, based upon machine learning instructions executed by the ICM 12 that generates alerts over health conditions or arrhythmias of selected medical concern, the ICM 12 could upload an event detection application to the sensor 104 or device 102 to enable those devices to detect those types of potentially medically-significant events. Alternatively, the event detection application could be downloaded to the sensor 104 or device 102 from an online application store or similar online application repository. Finally, the ICM 12 could use the sensor 104 or device 102 to generate an appropriate alert, including contacting the patient's physician or healthcare services, via wireless (or wired) communications, upon detecting a potentially medically-significant event or in response to a patient prompting.

The mobile device 102 could also serve as a conduit for providing the data collected by the wearable physiology monitor or activity sensor 104 to a server 122, or, similarly, the wearable physiology monitor or activity sensor 104 could itself directly provide the collected data to the server 122. The server 122 could then merge the collected data into the wearer's EMRs 134 in the secure database 124, if appropriate (and permissible), or the server 122 could perform an analysis of the collected data, perhaps based by comparison to a population of like wearers of the wearable physiology monitor or activity sensor 104. Still other server 122 functions on the collected data are possible.

Further, in a yet further embodiment, the ICM 12 can be interrogated using a conventional inductive programmer 100, which could be interfaced to the application program 98 executing on a physician's device, or in a standalone fashion. Inductive interfacing may be necessary where the transceiver 85 has suffered an error condition or is otherwise unable to communicate externally.

Figure 15:
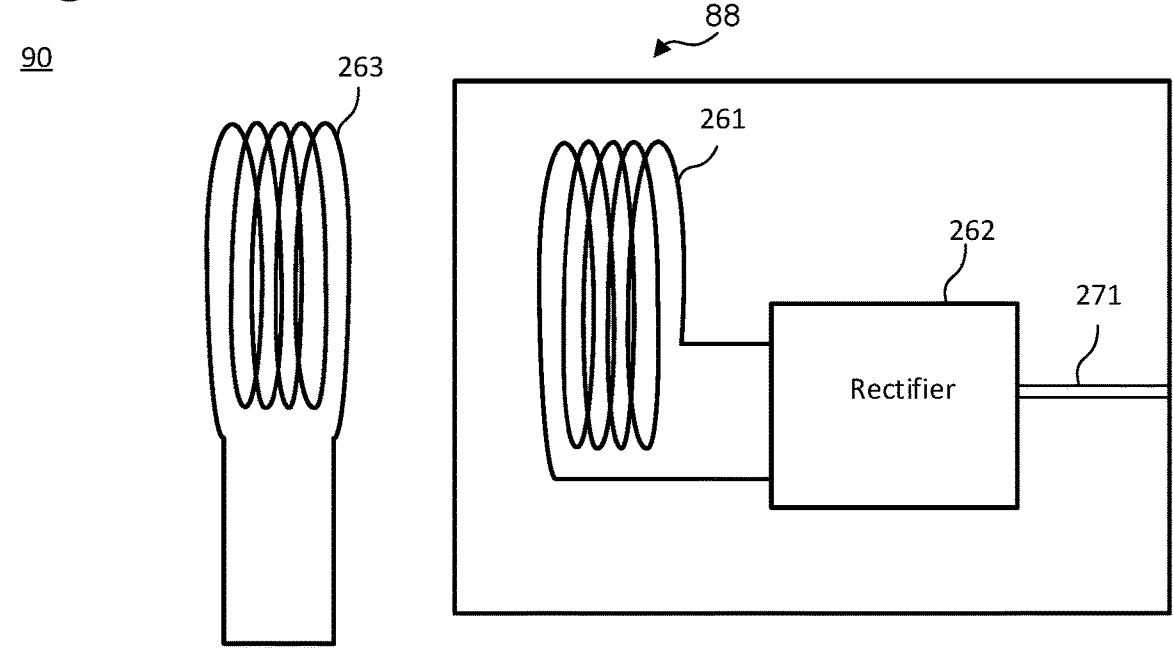
FIG. 15 is a diagram showing the energy harvesting module of FIG. 13 with a configuration to receive energy from an external inductive coil via inductive coupling in accordance with one embodiment.

Finally, as further described below beginning with reference to FIG. 15, the ICM 12 can interface with devices used for recharging the ICM 12, such as the transmission coil 263 described below or an external device 380 described below that can combine recharging and data offload capabilities.

Figure 10:
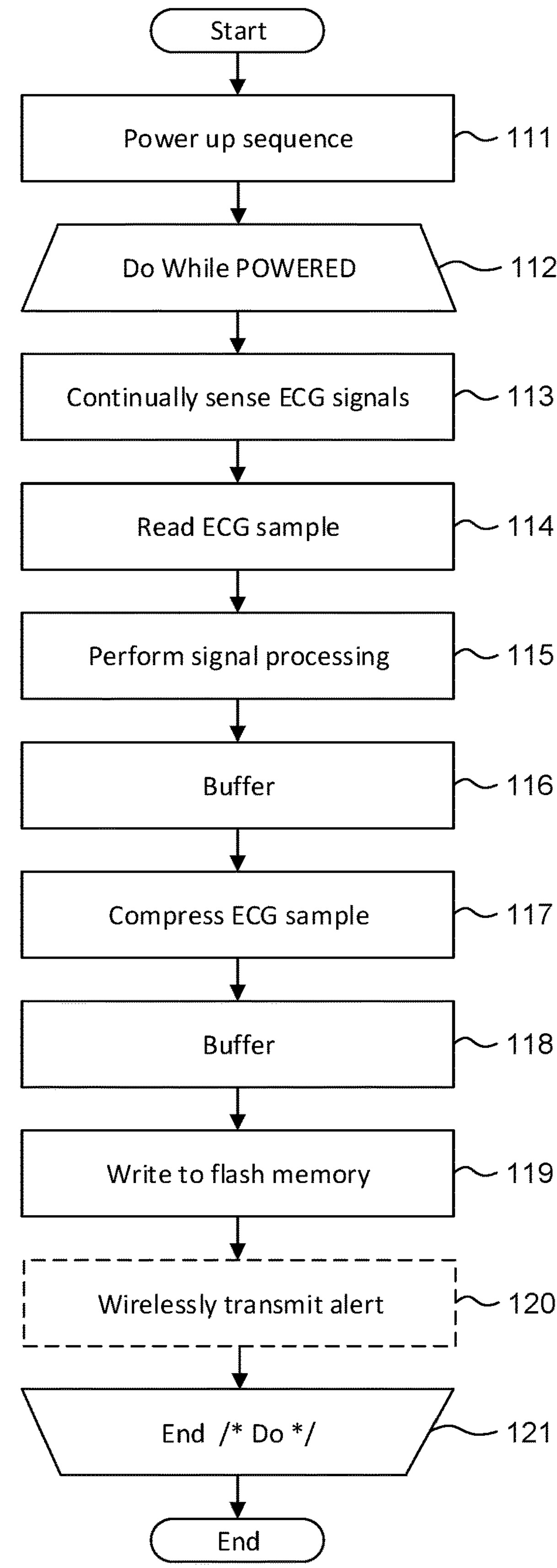
FIG. 10 is a flow diagram showing an ICM-implemented method for monitoring ECG data.

The ICM 12 continuously monitors the patient's ECG, heart rate and physiology over a long period of time lasting up to several years in duration. FIG. 10 is a flow diagram showing an ICM-implemented method 110 for monitoring ECG data. Initially, upon successful implantation, the microcontroller 61 executes a power up sequence (step 111). During the power up sequence, the voltage of the battery is checked, the state of the flash memory 62 is confirmed, both in terms of operability check and available capacity, and microcontroller operation is diagnostically confirmed.

Following satisfactory completion of the power up sequence, an iterative processing loop (steps 112-121) is continually executed by the microcontroller 61. During each iteration (step 112) of the processing loop, the ECG frontend 63 (shown in FIG. 11) continually senses the dermal ECG electrical signals (step 113, FIG. 10) via the ECG electrodes 16 and 17 and is optimized to maintain the integrity of the P-wave. A sample of the ECG signal is read (step 114) by the microcontroller 61 by sampling the analog ECG signal that is output by the ECG front end circuit 63. Each sampled ECG signal, in quantized and digitized form, is processed by signal processing modules as specified in firmware (step 115), as described infra, and temporarily staged in a buffer (step 116), pending compression preparatory to storage in the flash memory 62 (step 117). Following compression, the compressed ECG digitized sample is again buffered (step 118), then written to the flash memory 62 (step 119) using the communications bus. In a further embodiment, an alert that includes the compressed ECG digitized sample can also be wirelessly transmitted upon the triggering of a preset condition (step 120), such as an abnormally low heart rate in excess of 170 beats per minute (bpm), an abnormally low heart rate falling below 30 bpm, or AF detected by onboard analysis of RR interval variability by the microcontroller 61. Processing continues for an indefinite duration (step 121). Still other operations and steps are possible.

The microcontroller 61 operates under modular micro program control that includes processing of raw analog ECG signals. FIG. 11 is a functional block diagram showing the signal processing functionality 130 of the microcontroller 61. The microcontroller 61 operates under modular micro program control as specified in firmware 132. The firmware modules 132 include high and low pass filtering 133, and compression 134. Other modules are possible. The microcontroller 61 has a built-in ADC, although ADC functionality could also be provided in the firmware 132.

The ECG front end circuit 63 first outputs an analog ECG signal, which the ADC 131 acquires, samples and converts into an uncompressed digital representation. The microcontroller 61 includes one or more firmware modules 133 that perform filtering. In one embodiment, three low pass filters and two high pass filters are used. Following filtering, the digital representation of the cardiac activation wave front amplitudes are compressed by a compression module 134 before being written out to storage 135.

The download station 92 (shown in FIG. 9) executes a data link program ("DL") 93 or similar program that wirelessly interfaces with the ILR 12 to retrieve the stored ECG monitoring data and perform other functions. FIG. 12 is a functional block diagram showing the operations 140 performed by the download station 141. The download station 141 could be a server, personal computer (as shown), tablet or handheld computer, smart mobile device, or purpose-built programmer designed specific to the task of wirelessly interfacing with a ICM 12. Still other forms of download station are possible, including download stations connected through indirect wireless interfacing using, for instance, a smart phone connected to the ICM 12 through Bluetooth or Wi-Fi, or over an inductive coupling.

The download station 141 is responsible for offloading stored ECG monitoring data from a ICM 12. The download station 141 operates under programmable control as specified in software. The stored ECG monitoring data remotely retrieved from storage 142 on a ICM 12 is first decompressed by a decompression module 143, which converts the stored ECG monitoring data back into an uncompressed digital representation more suited to signal processing than a compressed signal. The retrieved ECG monitoring data may be stored into local storage (not shown) for archival purposes, either in original compressed form, or as uncompressed.

The download station 141 can include an array of filtering modules. For instance, a set of phase distortion filtering tools 144 may be provided, where corresponding software filters can be provided for each filter implemented in the firmware executed by the microcontroller 61. The digital signals are run through the software filters in a reverse direction to remove phase distortion. For instance, a 45 Hertz high pass filter in firmware may have a matching reverse 45 Hertz high pass filter in software. Most of the phase distortion is corrected, that is, canceled to eliminate noise at the set frequency, but data at other frequencies in the waveform remain unaltered. As well, bidirectional impulse infinite response (IIR) high pass filters and reverse direction (symmetric) IIR low pass filters can be provided. Data is run through these filters first in a forward direction, then in a reverse direction, which generates a square of the response and cancels out any phase distortion. This type of signal processing is particularly helpful with improving the display of the ST-segment by removing low frequency noise.

An automatic gain control (AGC) module 145 can also be provided to adjust the digital signals to a usable level based on peak or average signal level or other metric. AGC is particularly critical to single-lead ECG monitors, where physical factors, such as the tilt of the heart, can affect the electrical field generated. On three-lead Holter monitors, the leads are oriented in vertical, horizontal and diagonal directions. As a result, the horizontal and diagonal leads may be higher amplitude and ECG interpretation will be based on one or both of the higher amplitude leads. In contrast, the ICM 12 has only a single lead that is oriented in the vertical direction, so variations in amplitude will be wider than available with multi-lead monitors, which have alternate leads to fall back upon.

In addition, AGC may be necessary to maintain compatibility with existing ECG interpretation software, which is typically calibrated for multi-lead ECG monitors for viewing signals over a narrow range of amplitudes. Through the AGC module 145, the gain of signals recorded by the ICM 12 of the electrocardiography monitor 12 can be attenuated up (or down) to work with FDA-approved commercially available ECG interpretation.

AGC can be implemented in a fixed fashion that is uniformly applied to all signals in an ECG recording, adjusted as appropriate on a recording-by-recording basis. Typically, a fixed AGC value is calculated based on how an ECG recording is received to preserve the amplitude relationship between the signals. Alternatively, AGC can be varied dynamically throughout an ECG recording, where signals in different segments of an ECG recording are amplified up (or down) by differing amounts of gain.

Typically, the ICM 12 will record a high resolution, low frequency signal for the P-wave segment similar to the ICM's dermal cousin, such as provided with the dermal ambulatory monitors cited supra. However, for some patients, the result may still be a visually small signal. Although high resolution is present, the unaided eye will normally be unable to discern the P-wave segment. Therefore, gaining the signal is critical to visually depicting P-wave detail. This technique works most efficaciously with a raw signal with low noise and high resolution, as typically generated by the ICM 12. Automatic gain control applied to a high noise signal will only exacerbate noise content and be self-defeating.

Finally, the download station can include filtering modules specifically intended to enhance P-wave content. For instance, a P-wave based boost filter 146, which is a form of a pre-emphasis filter, can be applied to the signal to restore missing frequency content or to correct phase distortion. Still other filters and types of signal processing are possible.

In one embodiment, the ICM 12 can simply be inserted with a small surgical incision that is the width of the widest part of the ICM, typically the transverse cross section of the thickest aspect of the housing 15. Blunt dissection thereafter under local anesthesia can be used to create the subcutaneous space to receive the ICM 12, which would generally be inserted into the implantation site, proximal (housing) end first, followed by the distal (electrode assembly) end. In a further embodiment, the ICM 12 can be implanted in the patient's chest using, for instance, a minimally invasive subcutaneous implantation instrument, such as described in U.S. Pat. No. 6,436,068, issued Aug. 20, 2002 to Bardy, the disclosure of which is incorporated by reference.

While the ICM 12 is described above as having particular features, in a further embodiment, the ICM 12 within which the energy harvesting module 88 is integrated could be other types of implantable cardiology and other physiology monitor that have a rechargeable battery or other parts of their circuitry that need to be recharged. For example, the ICM 12 could be an implantable medical device such as described in U.S. Pat. No. 11,696,681, issued Jul. 11, 2023, entitled "Configurable Hardware Platform For Physiological Monitoring Of A Living Body," to Felix et al. ("the Felix Publication"), the disclosure of which is incorporated by reference. The Felix Publication discloses a configurable hardware platform for health and medical monitoring of physiology that is housed within a hermetically sealed implantable medical device (IMD). Briefly, physically, the IMD has a generally tubular shape that includes a central tubular body with rounded semi spherical end caps. When configured to measure electrocardiographic signals, the central tubular body and one of the semi spherical end caps function as electrode dipoles. The semi spherical end cap is electrically conductive yet electrically insulated from the central tubular body. As well, the outside surface of the central tubular body is partially electrically insulated, generally on the surface closest to the electrically conductive semi spherical end cap to form a non-electrically conductive inversion with only the outside surface distal to that semi spherical end cap being exposed. When placed within the central tubular body, a flexible circuit board forms three aspects of a microcontroller circuit assembly that respectively define a receiving coil for inductive charging and optional communication, a high frequency antenna for radio frequency (RF) data exchange, and a flexible circuit board containing a microcontroller and device circuitry. An onboard power source that includes a rechargeable energy cell, battery, or supercapacitor is also placed within the tubular body to one end of the flexible circuit board and, optionally, in electrical contact through a protection circuit with the electrically conductive semi spherical end cap, thereby serving as an electrical feedthrough to the flexible circuit board. The power source may be recharged through a charging and conditioning circuit interfaced with the microcontroller using a non-contact method, such as inductive charging, resonant charging, energy harvesting, thermal gradient charging, ultrasonic charging, RF-based charging or charging by ambient or driven motion. All or parts of the energy harvesting 88 could be included in the IMD disclosed by the Felix Publication to recharge the rechargeable power source. The energy harvesting module 88 could be used to supplement the energy provided by the receiving coil described in the Felix Publication, or the double-helix shaped coil 750 could be used as the power receiving coil 536 of the IMD described by the Felix publication, as further described below beginning with reference to FIG. 28. In a still further embodiment, part or all of the energy harvesting module 88 could be integrated into other kinds of implantable medical devices.

The energy harvesting module 88 provides a way to continually obtain additional energy for powering the ICM 12 while implanted within the patient 10, potentially extending the term of use of the ICM 12 to the lifetime of the patient. One source of the energy being harvested can be the kinetic energy generated by the patient 10. FIG. 14 is a diagram showing the energy harvesting module 88 of FIG. 13 with a configuration to harvest kinetic energy in accordance with one embodiment. In this embodiment, the energy harvesting module 88 includes an electrical motor 250 that is composed of a rotor 251 that is integrated into a stator 253, with the stator 253 producing electrical energy upon the rotation of the rotor 251. An oscillating weight 252 is fixedly attached to the rotor 251. The weight 252 pivots during normal movements of the patient due to the changes in the position of the patient's body (such as getting up, lying or sitting down, walking, and exercising). The pivoting of the weight 252 causes the rotation of the rotor 251, which causes the stator 253 to produce electrical energy. While the weight is shown to be of a particular shape with reference to FIG. 14, other shapes of the weight 253 are also possible. The generated electrical energy is provided either to the power cell 87 or directly to other components of the circuitry 80 of the ICM 12. In one embodiment, the production of electrical energy by the energy harvesting module can be detected by the microcontroller 81 and recorded into the flash memory 82 as an indication of the patient moving during the time the energy harvesting module 88 produces the energy. Such movement data can subsequently be unloaded and processed along with the electrophysiological data collected by the ICM12 and provide additional context for any cardiac events.

The energy harvesting module 88 can also harvest energy that is deliberately directed at the ICM 12. FIG. 15 is a diagram showing the energy harvesting module 88 of FIG. 13 with a configuration to receive energy from an external inductive coil via inductive coupling as part of the system 9—in accordance with one embodiment. In this embodiment, the energy harvesting module 88 includes at least one receiving coil 261 that generates alternating current upon being exposed to a magnetic field generated by a transmitting coil 263 located outside the patient 10. Thus, when the ICM 12 (or another form of monitor, such as the IMD 500, 560 described below) is implanted into the patient 10, the external coil 263 (which can be included in a wand operated by qualified medical personnel) can be positioned in proximity to the patient's chest, with the external coil 263 generating a magnetic field upon electricity being ran through the external coil 263. The magnetic field induces the generation of the alternating current within the inductive coil 261 within the energy harvesting module 88 in accordance with Faraday's law of induction. The generated alternated current is provided to a rectifier 262, which converts the alternating current to direct current is provided either to the power cell 87 or directly to other components of the circuitry 80 of the ICM (such as via wires 271). The transfer of energy to the inductive coil 261 can be performed at the same time as offloading of data collected by the ICM 12, as further described below with reference to FIG. 19. As further described below beginning with reference to FIG. 20, the energy harvesting module 88 can include multiple receiving coils positioned in a way that minimizes parasitic interactions between them. A particular configuration of the transmitting coil 263 is described below with reference to FIG. 27.

Figure 16:
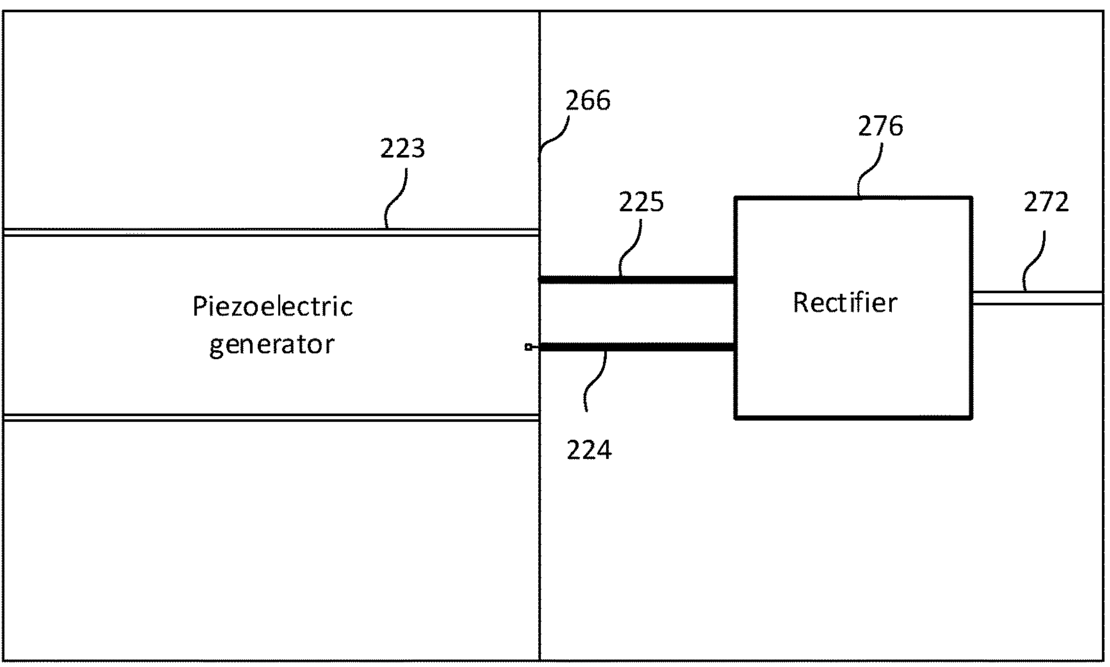
FIG. 16 is a diagram showing the energy harvesting module of FIG. 13 with a configuration that includes a piezoelectric energy generator in accordance with one embodiment.

Vibrations that the ICM 12 is exposed while being inside the patient's body, which can be caused either by the patient's movements or caused by external factors, can also be harvested and used for energy generation. FIG. 16 is a diagram showing the energy harvesting module 88 of FIG. 13 with a configuration that includes a piezoelectric energy generator 223 in accordance with one embodiment. The generator 223 includes a piece of piezoelectric material, such as piezoelectric rubber, that is stretched (under tension) on a partition 267 within the energy harvesting module 88. Upon vibrations reaching the energy harvesting module 88, the vibrations cause a deformation of the stretched piezoelectric material, which produces alternating current. The piezoelectric generator 88 is interfaced via wires 224, 225 to a rectifier 226, which converts the alternating current to direct current, which in turn is provided either to the power cell 87 or directly to other components of the circuitry 80 of the ICM 12 (such via wires 172). In one embodiment, the vibrations that the energy harvesting module 88 harvests to produce electrical energy can be vibrations of caused by the patient's heartbeat, though other sources of vibrations are possible.

Figure 17:
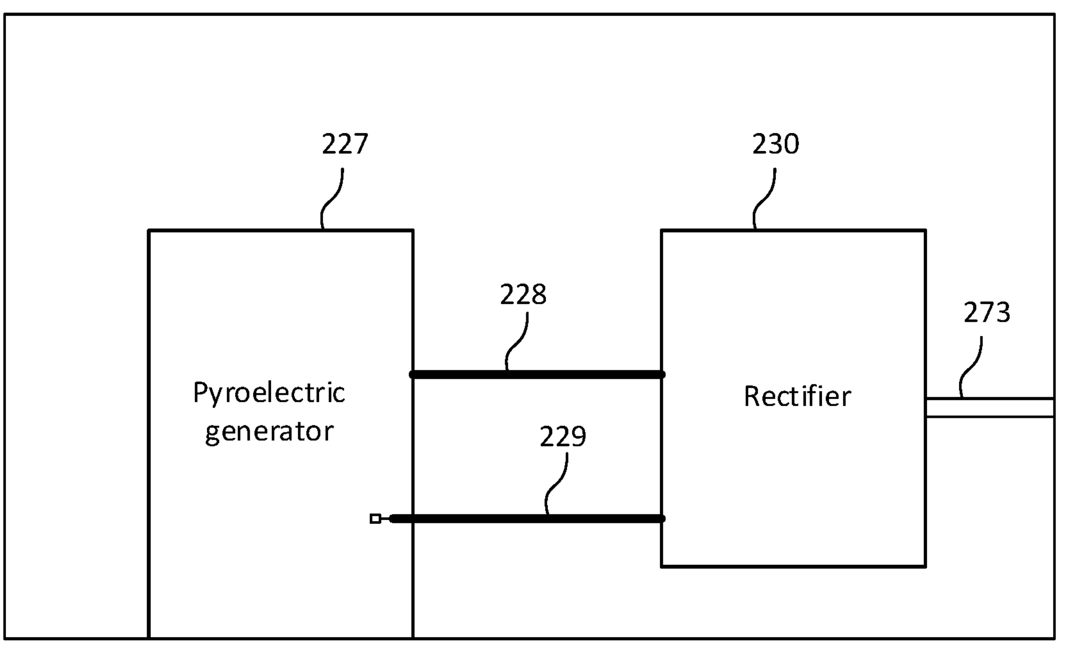
FIG. 17 is a diagram showing the energy harvesting module of FIG. 13 with a configuration to generate electrical energy upon a change in the patient's bodily temperature in accordance with one embodiment.

The patient's bodily temperature fluctuates depending on time of day, activity level, dietary intake, and other factors. This fluctuation in temperature can be taken advantage of to generate electrical energy for the ICM 12. FIG. 17 is a diagram showing the energy harvesting module 88 of FIG. 13 with a configuration to generate electrical energy upon a change in the patient's bodily temperature in accordance with one embodiment. In this embodiment, the energy harvesting module 88 includes a pyroelectric material 227, such as a pyroelectric crystal (though other pyroelectric materials are also possible) that generates alternating current upon the change in the temperature of the patient's body (and consequently, the change in the temperature of the pyroelectric material). The pyroelectric material 227 is interfaced via wires 228, 229 to a rectifier 240, which converts the alternating current to direct current, which in turn is provided either to the power cell 87 or directly to other components of the circuitry 80 of the ICM 12 (such as via wires 173).

Figure 18:
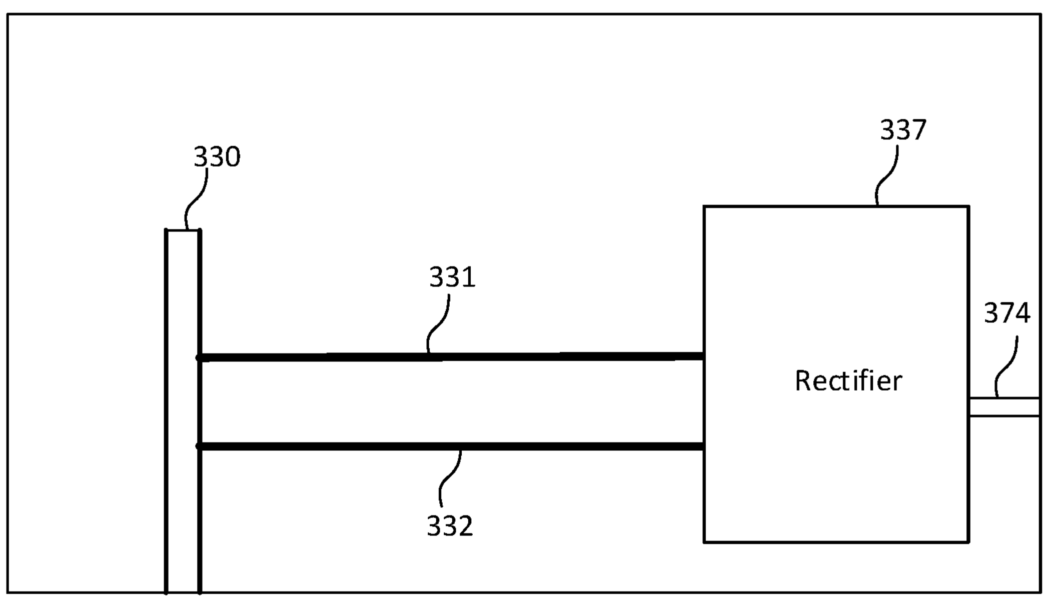
FIG. 18 is a diagram showing the energy harvesting module of FIG. 13 with a configuration to harvest energy of radio waves in accordance with one embodiment.

A further source of energy that the energy harvesting module 88 can take advantage of are radio waves, which are plentiful in most populated areas. FIG. 18 is a diagram showing the energy harvesting module 88 of FIG. 13 with a configuration to harvest energy of radio waves in accordance with one embodiment. In this embodiment, at least a portion (such as one side) of the housing 15 of the ICM 12 is made of a material that is transparent to radio waves, such as plastic, though other radio transparent materials are possible. The energy harvesting module 88 includes an antenna 330 that generates alternating current upon capturing radio waves originating from outside the patient's body. The antenna 330 is interfaced by wires 331, 332 to a rectifier 337, such as a diode (though other rectifiers are possible) that converts the alternating current to direct current, and which supplies the direct current either to the power cell 87 or directly to other components of the circuitry 80 of the ICM 12 (such as via wires 374). In one embodiment, the antenna 330 could be a folded unipole antenna. In a further embodiment, the antenna 330 could be a dipole antenna. Still other kinds of antennas 330 are possible. While the antenna 330 is shown to be compartmentalized to the energy harvesting module 88 of the ICM 12, in a further embodiment, at least a portion of the antenna 330 can be located in other portions of the housing 15, such as being wrapped around the internal periphery of the housing 15. In a still further embodiment, at least a portion of the antenna 330 could be located on the outside of the housing 15. Further, while the antenna 330 could be a stand-alone antenna that only has the function of harvesting power (with a different antenna being used by the wireless transceiver 85 for communication and data offloading), in a further embodiment, the antenna 330 could also be used by the wireless transceiver 85 to offload collected data and other wireless communication, with no additional antenna used exclusively by the wireless transceiver 85 being included in the ICM 12.

Figure 19:
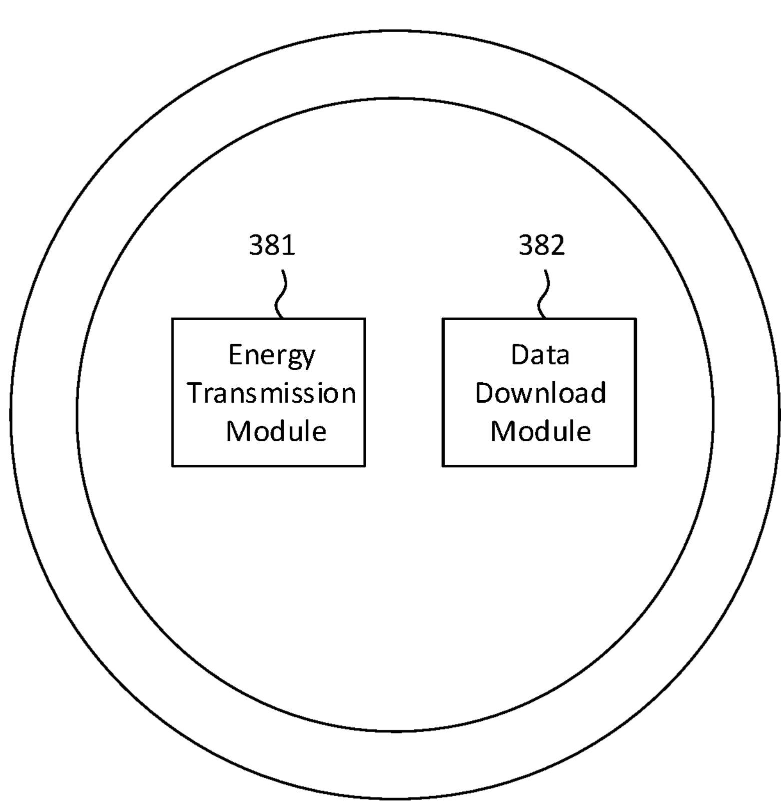
FIG. 19 is a diagram showing an external device combining energy transmission and data download capabilities for use with the ICM in accordance with one embodiment.

While the energy harvesting module 88 can produce electrical energy using radio waves originating from many sources outside of the patient's body, the radio waves can also be specifically directed at the energy harvesting module. Thus, a properly-trained patient or a qualified medical professional can use an external source of the radio waves to specifically provide the power to the energy harvesting module 88. The source of radio waves can also include the capability to wirelessly receive data collected by the ICM 12, which the ICM 12 can offload at the same time as the energy harvesting module 88 is receiving energy. FIG. 19 is a diagram showing an external device 380 combining energy transmission and data download capabilities for use with the ICM 12 in accordance with one embodiment. The external device 380 can be shaped as a puck that can be pressed against (or held close to) the patient's chest in the parasternal region at the level at which the ICM 12 is implanted. The external device 380 includes an energy transmission module 381 that is capable of interfacing with the energy harvesting module 88 to provide input (such as magnetic or radio waves) that allows the energy harvesting module 88 to produce electrical energy. For example, the energy transmission module 381 can include a radio transmitter that radiates radio waves captured by the antenna 330. The energy transmission can also include, alternatively or in addition to the radio transmitter, the transmitting coil 263 that generates the magnetic field that causes the inductive coil 261 within the energy harvesting module 88.

Further, the external device 380 includes a data download module 382, which uses an internal wireless transceiver to wirelessly download data collected by the ICM 12 by interfacing with the wireless transceiver 85 of the ICM 12. The downloading of the data can happen simultaneously to the energy transmission module 381 supplying the input to the energy harvesting module 88 of the ICM, allowing to reduce the time that the external device 380 would need to be held next to the patient 10. The downloaded physiological data can in turn wirelessly forwarded by the external device 380 for further processing, such as to the server 94, such as further described in U.S. Pat. No. 11,096,579, issued Aug. 24, 2021, entitled "SYSTEM AND METHOD FOR REMOTE ECG DATA STREAMING IN REAL-TIME," to Dreiscbach et al., the disclosure of which is incorporated by reference. The external device 380 can also perform processing of the downloaded data, as described above with reference to FIG. 12, prior to transmitting the data to the server 14. The external device 380 further includes components necessary for the functioning of the modules 381 and 382 and other processing, such as a processor, memory, and either an internal source of power, or a connection to an external source of power.

In addition, while the external device is shown as a puck with reference to FIG. 19, in a further embodiment, other configurations of the external device 380 are possible. For example, the external device 380 could be shaped as a wand. Still other configurations of the external device are possible.

As mentioned above, the energy harvesting module 88 can include multiple receiving coils 261A, 261B that generate alternating current upon being exposed to a magnetic field generated by a transmitting coil 263 located outside the patient 10. In the description below, such receiving coils are also referred to as solenoids. Having multiple receiving solenoids increases the surface area that can be used for inductive charging. However, as the fields induced by the solenoids can have parasitic effect on each other, decreasing the overall amount of current generated by them, optimizing the positioning of the solenoids relative to each other is important for increasing the rate at which the energy harvesting module 88 generates energy and at which the ICM 12 (including the IMD 500, 560 described below) can be recharged. For the sake of clarity, in the example below, the multiple receiving coils 261 are often described below as being two solenoids 261A, 261B that receive energy from the transmitting coil 263. However, as also described below, other numbers of receiving coils 263 are possible.

FIG. 20 is a diagram showing a double-helix shaped receiving coil 750 formed by overlapping receiving coils 261A, 261B for use in the energy harvesting module 88 to receive energy from an external transmitting coil 263 via inductive coupling in accordance with one embodiment. The coils 261A, 261B overlap with each other and are attached to each other as further described below. The solenoids 261A, 261B are positioned so that the solenoidal tilt angle is 45° while the solenoids 261A, 261B are positioned to intersect orthogonally (perpendicularly), at a 90° angle, relative to each other. The 45° angle and the orthogonal positioning minimizes any interactions between the solenoids 261A, 261B, the mutual inductance of the solenoids 261A, 261B and any parasitic interactions between them. Together, the two solenoids 261A, 261B form a shape resembling a double-helix. The solenoids 261A, 261B could be made of polyimide copper, though other types of materials are also possible. As the interactions between the solenoids 261A, 261B is minimized, due to the increased surface area (when compared to a single solenoid) available for receiving energy via inductive coupling, the rate at which the combined solenoids 261A, 261B can be used to recharge the components of the ICM 12 is significantly higher than when a single solenoid is used. Despite the increased surface area, the amount of space that the two solenoids 261A, 261B occupy is insignificantly greater than occupied by a single solenoid due to the two solenoids 261A, 261B overlapping, thus helping to minimize the size of the ICM 12. Further, when the housing of the ICM 12 is of a tubular shape (such as of the implantable medical device 500, 560 described below), the double-helical shape of the coil formed by the solenoids 261A, 261B allows the coil 750 to be positioned along the interior walls of the housing, thus maximizing the amount of space available within the housing for other components of the ICM 12. The overlapping solenoids 261A, 261B can also be used in an energy harvesting module 88 of an ICM 12 that has a non-tubular housing.

The thickness of the wires (also referred to as traces or circuit traces) making up the solenoids 261A, 261B influences the resistance of the solenoids 261A, 261B (and consequently, the degree to which they heat up) as well as their inductance (and consequently their ability to receive energy). In particular, increasing the thickness decreases the resistance (making the solenoids 261A, 261B less likely to heat up) but also decreases the number of times the solenoids 261A, 261B can be wrapped each other in a limited space, which in turn decreases the inductance and the ability of the solenoids to receive energy. Thus, optimal thickness must be chosen to consider both the resistance and the inductance. In one embodiment, the wire thickness could be in the 6 mils-60 mils range (with one mil being one thousandth of an inch), though other wire thickness could also be used.

Depending on the length of the wires making up the solenoids 261A, 261B, the solenoids 261A, 261B can be wrapped around each other multiple times (while retaining the same orthogonal positioning described earlier), thus creating multiple layers of overlapping coils, allowing to minimize the amount of space the solenoids 261A, 261B occupy, and increasing the inductance of the solenoids 261A, 261B. As illustrated by FIGS. 26A-27B, the solenoids 261A, 261B shown with reference to FIG. 20, are wrapped around each other twice. Other number of wraparounds are possible.

As mentioned above, while only one pair, two solenoids 261A, 261B, are shown with reference to FIG. 20, other numbers of solenoids could be combined to further increase the surface area available for use in inductive charging. For example, additional two solenoids 261A, 261B could be combined with the first pair of solenoids 261A, 261B to form the double-helix-shaped coil 750, resulting in the double-helix shaped coil 750 being composed of two pairs of coils 261A, 261B. A first additional solenoid 261A could be wrapped around the outside surface of the first solenoid 261B; this first additional solenoid would be aligned with solenoid 261A, having a solenoidal tilt angle of 45° and being orthogonal to solenoid 261B. A second additional solenoid 261B would be wrapped around the first additional solenoid, and would be aligned with the solenoid 261B; the second additional solenoid would have a solenoidal tilt angle of 45° and would be orthogonal with the solenoid 261A and the first additional solenoid. Still other numbers of solenoids in the energy harvesting module 88 are possible.

Figure 21:
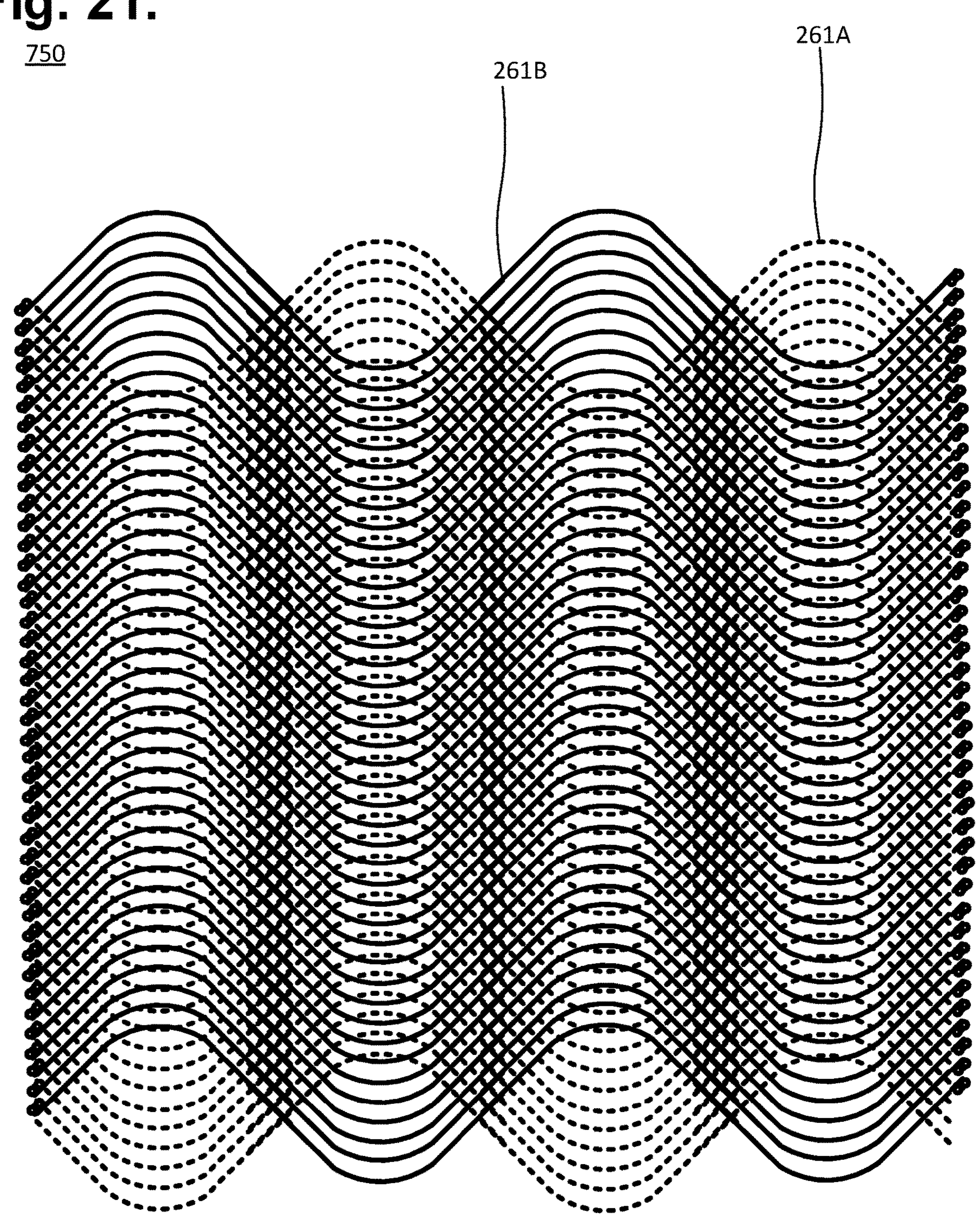
FIG. 21 is a diagram showing the solenoids of FIG. 20 unwrapped in accordance with one embodiment.

Showing the alignment of solenoids 261A, 261B when they are unwrapped and not forming a coil can help visualize their arrangement. FIG. 21 is a diagram showing the solenoids 261A, 261B of FIG. 20 unwrapped in accordance with one embodiment. The unwrapped solenoids 261A, 261B are sine shaped, they can be wrapped to create the coils seen with reference to FIG. 20. As the solenoids 261A, 261B are wrapped around each other multiple times, the period of the sine wave by which each unwrapped portion can be represented gets longer due to having around to wrap previously wrapped portions of the solenoids 261, 261B, as illustrated by FIGS. 26A-26B. FIGS. 26A-26B provide a bottom view of unwrapped solenoids 261A, 261B being wrapped into the coils seen with reference to FIG. 20 in accordance with one embodiment. FIG. 26A shows the wrapping of a portion of the unwrapped solenoids 261A, 261B, and FIG. 26B shows a result of wrapping of the solenoids 261A, 261B around each other a second time. As can be seen with reference to the FIGS. 26A-26B, the circumference of the circle formed by portions of the solenoids 261A, 261B used for the second wrapping around is greater than for the first wrapping around. To precisely predict the length of each segment of the solenoid 261A, 261B that is used for each wraparound, the period of the sine wave representing that segment (when unwrapped) is set to equal the circumference of the circle formed by the segment (when wrapped) when looked at from the perspective of FIGS. 26A-26B. With the circumference being determined according to the formula $2\pi r$, the circumference of the segment of the solenoids 261A, 261B used for each subsequent wraparound increases due to the increased radius of the circle formed by that segment. Thus, the period of the sine wave representing each segment of the solenoids must get longer with each wraparound. Knowing this increase allows to properly size each segment of each solenoids 261A, 261B. In particular, to achieve optimal alignment of the solenoids, the lengths of the segments of the solenoids 261A, 261B used for a single wraparound must be substantially equal.

Figure 22:
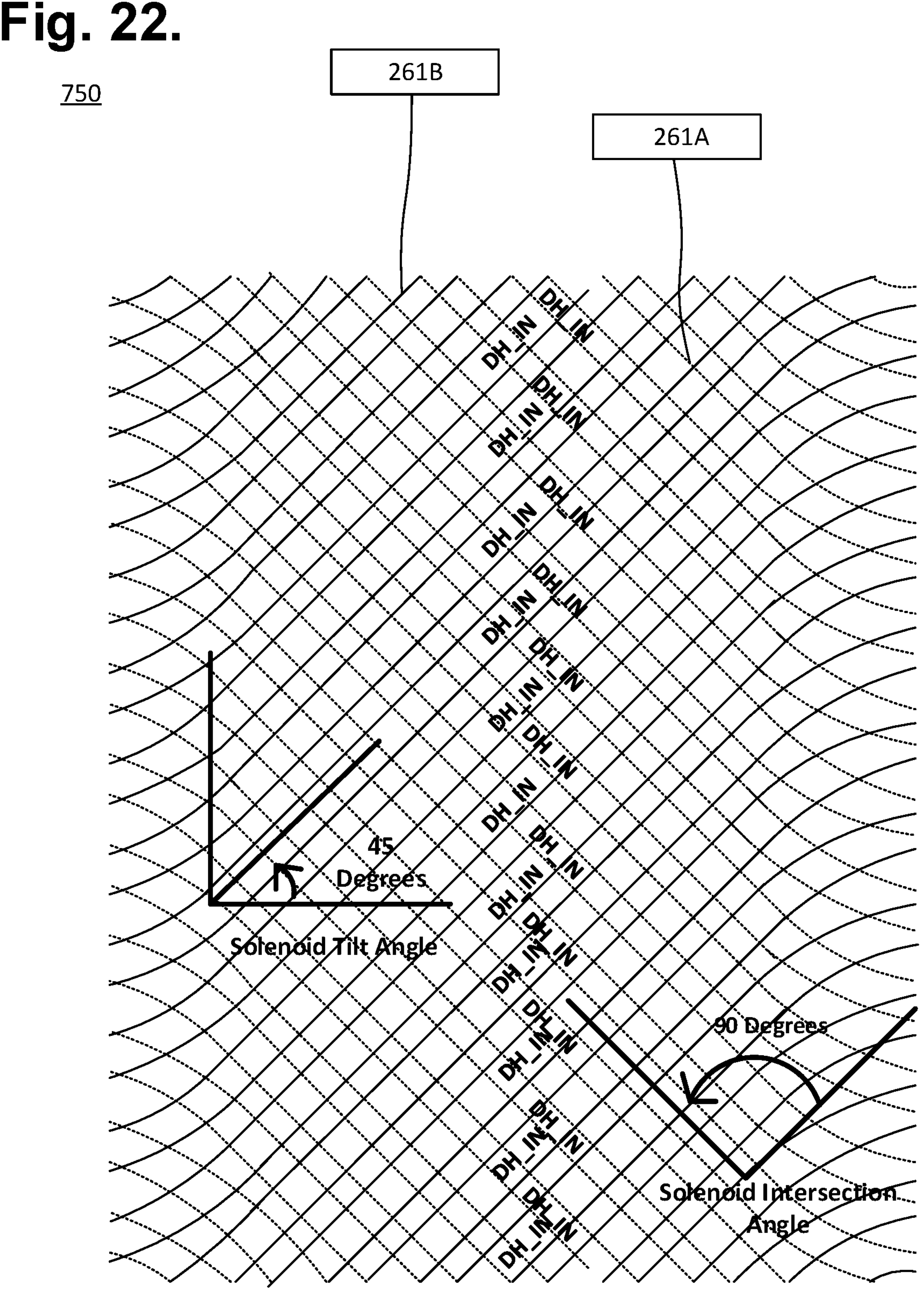
FIG. 22 is an illustration of the tilt angle and the overlap angles on a portion of unwrapped solenoids 261A, 261B in accordance with one embodiment.

As previously mentioned before, the solenoidal tilt angle of the solenoids 261A and 261B is around 45° and the solenoids 261A, 261B are positioned as to intersect substantially orthogonally to each other. FIG. 22 is an illustration of the tilt angle and the overlap angles on a portion of unwrapped solenoids 261A, 261B in accordance with one embodiment. When the solenoids 261A, 261B are wrapped, the angles are maintained.

Figure 23:
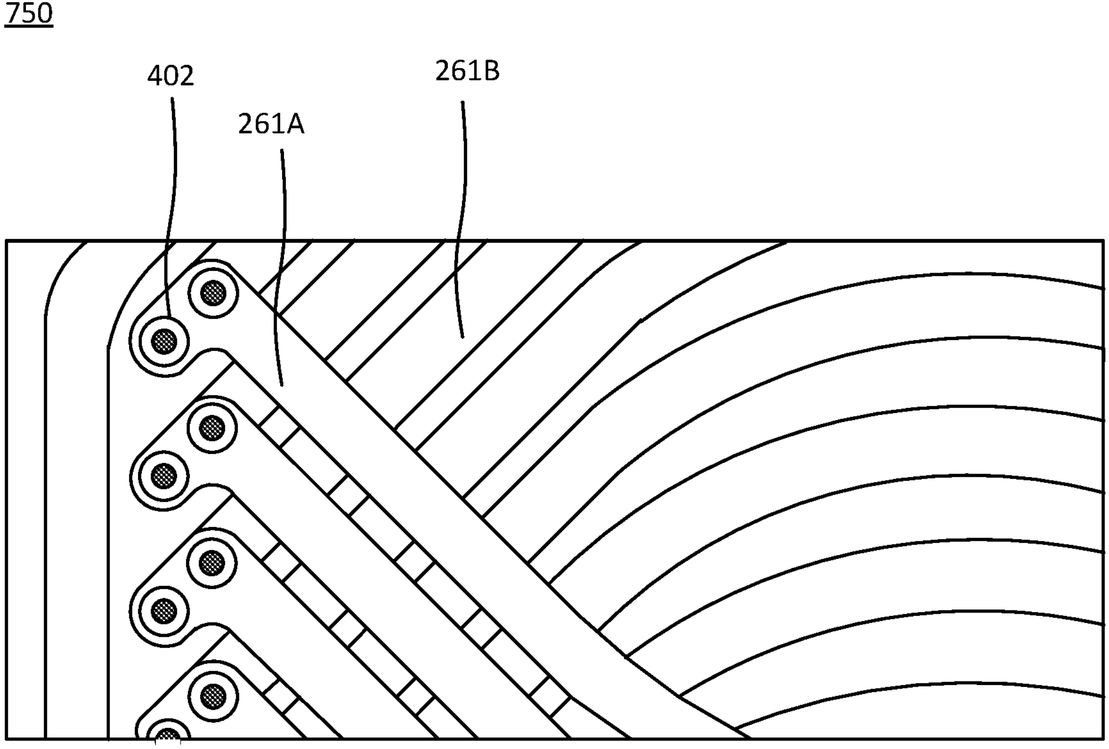
FIG. 23 is a close up of a portion of the FIG. 21 illustrating attachments of solenoids to each other in accordance with one embodiment.

The solenoids 261A, 261B are attached to each other in at least some portions to make sure that their positions with respect to each other are maintained. FIG. 23 is a close up of a portion of the FIG. 21 illustrating attachments of solenoids 261A, 261B to each other in accordance with one embodiment. As can be seen with reference to FIG. 23, the solenoids 261A, 261B can be attached to each other with vias 402, though other ways of attachments and reinforcement are also possible. Also, while a particular number of vias are shown as connecting the solenoids, in a further embodiment, a different number of vias could be used.

Figure 24:
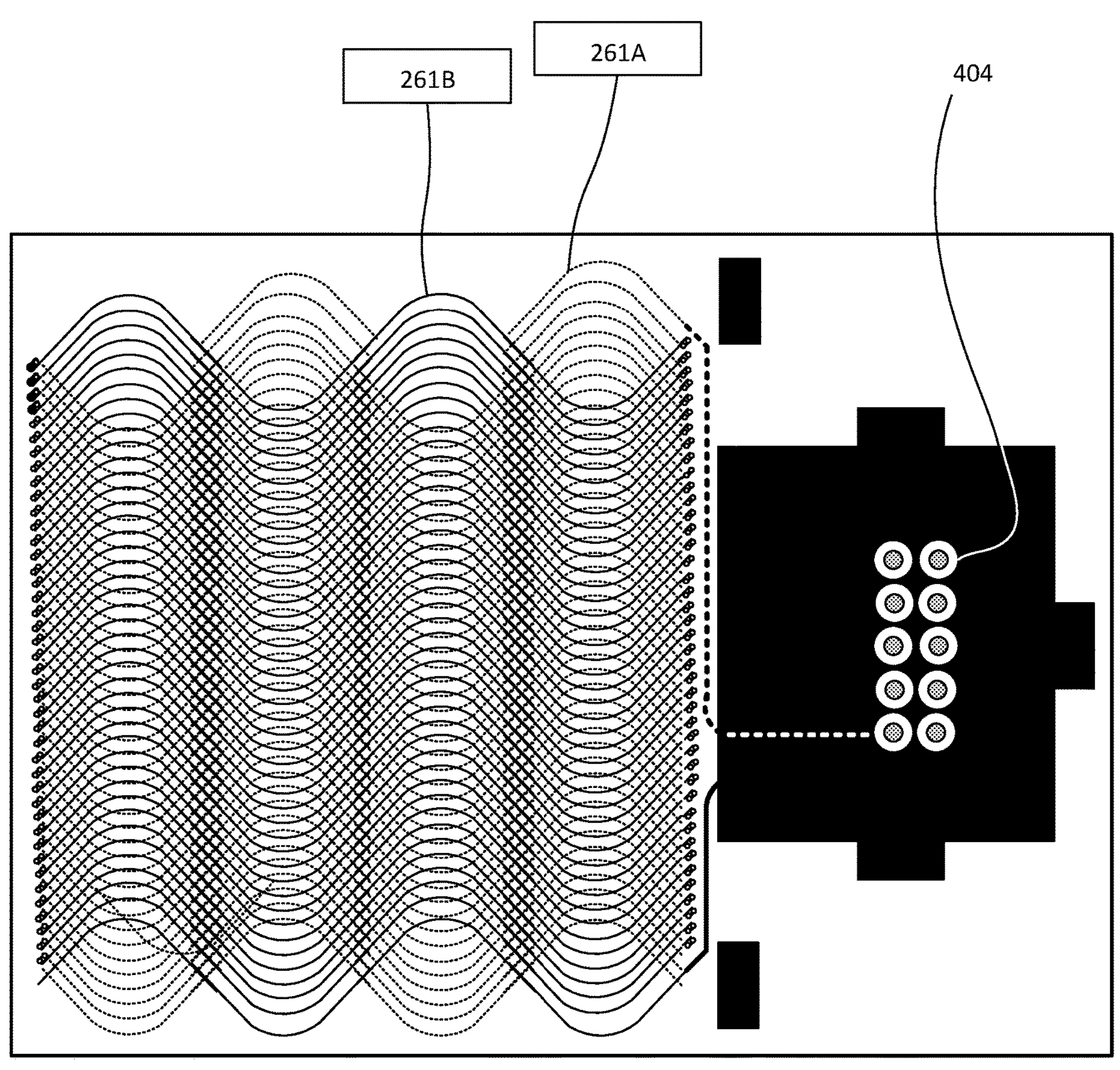
FIG. 24 is a diagram showing unwrapped solenoids connecting to other parts of the energy harvesting module in accordance with one embodiment.
Figure 25:
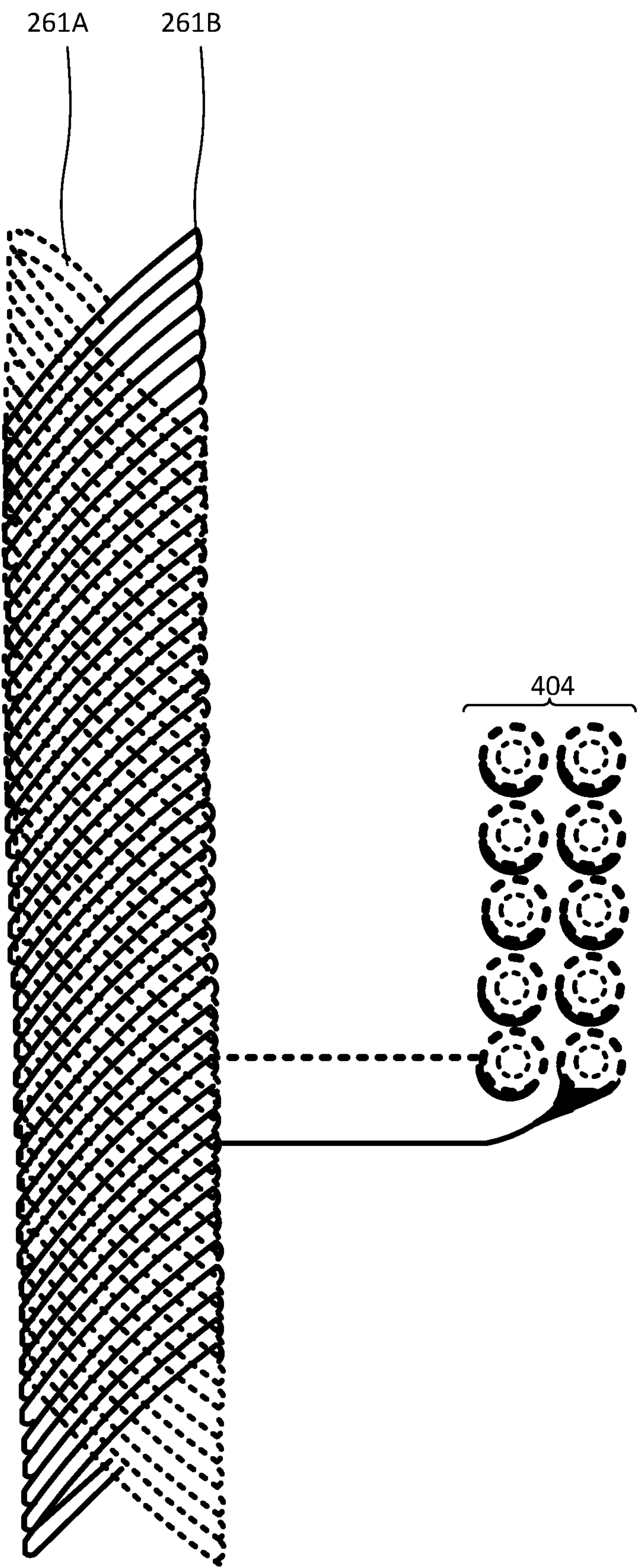
FIG. 25 is a diagram showing overlapping solenoids connecting to other parts of the energy harvesting module in accordance with one embodiment.

Each of the solenoids 261A, 261B also attaches to other portions of the energy harvesting module 88, such as a rectifier, to which the generated current is provided for recharging the power cell 87 or otherwise powering the circuitry 80 of the ICM 12. FIG. 24 is a diagram showing unwrapped solenoids 261A, 261B connecting to other parts of the energy harvesting module 88 in accordance with one embodiment. When the solenoids 261A, 261B are wrapped around each other and form the double-helical shape, they retain the connections to other parts of the energy harvesting module 88, as shown with reference to FIG. 25. FIG. 25 is a diagram showing overlapping solenoids 261A, 261B connecting to other parts of the energy harvesting module 88 in accordance with one embodiment. If the housing of the ICM 12 is tubular, one or more other portions of the energy harvesting module 88 could also be foldable to adopt a circular or partially-circular shape when the solenoids are overlapping.

The large surface area and the positioning of the overlapping solenoids 261A, 261B provides a way to increase the rate at which energy is received via inductive coupling from the transmitter coil 263 without significantly increasing the size of the energy harvesting module 88. Further, the double-helix shape is tolerant towards misalignment with the transmitting coil 263, thus allowing a reasonably high rate of charging even when the charging procedure is imperfect (such as when being conducted by the patient). The speed of the charging can further be increased without endangering the patient through a use of a transmitting coil that defines a triangular gap. FIG. 27 is a diagram showing a transmitting coil 263 that defines a gap 405 shaped substantially as a triangle with rounded corners in accordance with one embodiment. The triangular gap 405 allows to provide energy via inductive charging to the energy harvesting module 88 without overheating the energy harvesting module 88, the power cell 87, other portions of the ICM 12, or the surrounding thoracic tissues of the patient. The triangular gap 405 helps to compensate for misalignment between the transmitting coil 263 and the receiving coils.

In one embodiment, the width 407 of the entire transmitting coil 263 can be 6 inches-10 inches, with the height 406 base of the triangular gap 405 being 1 inch-3 inches. In this embodiment, changing the height 406 of the gap lower than 1 inch could increase the rate of transmission of energy too high, resulting in the ICM 12 or the patient's tissues heating up too much. Also, in this embodiment, changing the height of the gap 405 to be greater than 3 inches could make the rate of the transmission of energy to be too slow to be convenient for the patient. If the width 407 of the transmitting coil changes, the optimal height 406 of the gap 405 could also change. While the transmitting coil 263 with the triangular gap is particularly synergetic when transmitting energy to the overlapping solenoids described above, in a further embodiment, the transmitting coil 263 could also be used with other kinds of receiving coils and can be used to recharge multiple kinds of implantable medical devices. As mentioned above, the transmitting coil 263 with the gap 405 could be integrated into the external device 380. While the overall shape of the transmitting coil 263 is substantially circular, in a further embodiment, other overall shapes could be used as long as the substantially triangular gap 405 is retained in the central portion of the transmitting coil. For example, in one further embodiment, the transmitting coil 263 could have a shape of a figure eight.

As also further described below, a portion (such as the double-helix shaped coil 750) or the entirety of the energy harvesting module 88 could be a part of the IMD described by the Felix Publication. Additional details regarding the IMD are provided below. A configurable hardware platform for health and medical monitoring of physiology is housed within a hermetically sealed, implantable medical device (IMD). The IMD provides an implanted form of ambulatory physiological monitor that offers per-heartbeat monitoring with flexible and extensible monitoring capabilities. The IMD is designed to be implanted within a living body and to operate over an extended time period while monitoring different types of patient physiology, possibly at different times and in different ways.

The IMD can record every heartbeat, perform live transmission or delayed transmission, which may occur, for instance, two days or longer following recordation, or live monitoring. When every heartbeat is recorded and sent, the platform does not require an analysis algorithm onboard; rather, the analysis algorithm could be implemented at a datacenter or on a cell phone to do the heavy data processing by utilizing the better computing resources available on those platforms. The IMD is equipped with one or more physiological sensors that non-exhaustively include ECG, temperature, pulse oximetry, oxygen saturation, respiration, blood glucose, blood pressure, and drug levels or any appropriate measure of disease. In a further embodiment, the IMD can also monitor non-physiological data when the IMD is equipped with an appropriate type of sensor, such as posture as derived from data measured by an actigraphy sensor, accelerometer or inertial motion sensor. Other types of sensors and forms of physiology and non-physiological data capture are possible, such as cardiac effort level, thoracic impedance, and sound recording, including ultrasonic and sub-sonic sound recording.

The degree of surgical invasiveness required to implant the IMD depends upon the intended situs within the body, which is at least in part dictated by the desired range of physiology to be monitored. For instance, electrocardiographic monitoring of the heart that emphasizes the propagation of low amplitude, relatively low frequency content cardiac action potentials, particularly the P-waves that are generated during atrial activation, can be efficaciously performed by implanting the IMD in a subcutaneous situs located axially and slightly to either the left or right of the sternal midline in the parasternal region of the chest. This type of subcutaneous implantation can be performed in a physician's office using a specialized implantation instrument that includes a trocar to incise the skin and form a subcutaneous tunnel, and a cannula through which the IMD is guided into place, after which the implantation instrument is withdrawn and the surgical incision is closed.

Specific details of the IMD's housing, electronic and support circuitry, power source, and microarchitecture will now be discussed.

Housing

Physically, the IMD has a generally cylindrical shape that includes a central tubular body with rounded semi spherical end caps, although other shapes and configurations are possible. In a further embodiment, one or both of the semi spherical end caps may be replaced pointed or semi-pointed tips to ease insertion into the body. FIG. 28 is an outer perspective view showing an IMD 500 that houses a configurable hardware platform for physiological monitoring of a living body in accordance with one embodiment. The IMD 500 includes three primary assemblies. The main middle section of the IMD 500 is a central body 511 that can be formed from a medical grade titanium or similar medical implantation-safe material. The central body 511 has a tubular or cylindrical shape that defines an axial bore, which provides a hollow interior cavity that is open on both end caps running longitudinally over the length of the central body 511. Other shapes having non-circular or non-spherical shapes are possible. Rounded semi spherical end caps 512 and 513 are welded or affixed to the central body 511 to form a hermetically sealed device housing. The end caps 512 and 513 can be formed in other shapes, such as pointed or semi-pointed tips.

The central body 511 houses a flexible circuit board, a low frequency resonant charger antenna to facilitate device recharging, and an onboard power source generally consisting of a rechargeable energy cell, battery, or supercapacitor. One of the semi spherical end caps, known as the "Protectrode" 512, serves a dual purpose as an electrode and housing for patient and device protection components. The other semi spherical end cap, known as the "Radome" 513, houses a high frequency antenna used for transmitting data over an RF link, using, for instance, Bluetooth or WiFi. Additionally, the "Radome" 513 could be used to house an inductive antenna and inductive link. The RF link may also be used for device calibration and configuration. In a further embodiment, the "Radome" 513 can also house physiological sensors, such as pulse oximetry and blood pressure. In a further embodiment, the optically clear "Radome" 513 may allow light or other forms of radiation to be received and transmitted through to passively facilitate collection of other vital signs, such as pulse oximetry and blood pressure. In a still further embodiment, fiber optics or lenses implanted into the "Radome" 513 may facilitate collection of vital signs by sensors housed elsewhere.

The IMD 500 has an overall length of approximately 5.5 cm to 8.5 cm with an outer diameter, measured across the central body 511, of approximately 5-8 mm and a wall thickness of approximately 0.3 mm; however, other dimensions, including overall length, wall thickness, and outer diameter, are possible depending upon both the electronic circuitry and power source that need to be housed within and the types and numbers of physiological and non-physiological sensors.

In a further embodiment, the IMD 500 can be filled with a gas, such as argon or other inert gas. In particular, argon gas is conventionally used when welding titanium components and, when oxygen-purged into the interior of the IMD 500, further serves to preserve the electrical components and facilitate device longevity. In addition, supporting structure, such as an acrylic rod, can be used as an internal spacer to help keep the internal components in proper position.

In one embodiment, the central body 511 and the "Protectrode" 512 can be micro bead blasted to respectively increase the roughness of the central body 511 to improve silicone or Parylene bonding and to increase the surface area of the "Protectrode" 512 for better signal quality. A titanium nitride coating could also be applied to dramatically increase the surface area of the device.

The conductive surface 518 is formed by partially insulating the outside surface of the central body 11 using a non-electrically conductive, insulating surface treatment or coating ("insulating coating") 519. The insulating coating 519 is generally applied on the outer surface closest to the "Protectrode" 512, which maximizes the electrode dipole spacing. In one embodiment, the insulating coating 519 can be a chemical vapor deposited poly polymer, such as Parylene C. In a further embodiment, the insulating coating 519 can be a silicone polymer-based (polysiloxanes) coating. Alternatively, both forms of coatings, poly polymer and silicone polymer, could be employed. Poly polymers exhibit superior moisture resistance and insulation resistance properties, but are susceptible to damage from scratches and scrapes. Silicone polymer coatings form a durable protective layer and, when applied over a poly polymer coating, such as Parylene C, can protect the underlying coating from scratches and scrapes during insertion, repositioning, or removal of the IMD 500.

The end 522 of the central body 511 closest to the conductive surface 518 interfaces to the "Radome" 513. In one embodiment, the high frequency antenna is a separate component that is contained within the "Radome" 513. Here, the high frequency antenna can be held in place by filling the cavity of the "Radome" 513 with a filler material, such as acrylic, urethane, glass, or similar material, and the high frequency antennal is interfaced to a flexible circuit board via an electrical contact 520 that can be soldered or bonded to the high frequency antenna. In a further embodiment, the high frequency antenna is formed on a foldable "ear" section of the flexible circuit board and routed into the "Radome" 513 assembly.

In one embodiment, when configured to measure electrocardiographic signals, the "Protectrode" 512 and an exposed, conductive surface 518 of the central body 511 function as an electrode dipole. Other forms of electrode dipoles are possible. FIG. 29 is an outer perspective view showing the central body 11 of the IMD 500 of FIG. 1. The end cap 14 of the "Protectrode" 12 forms one electrode. An exposed, conductive surface 18 of the central body 11 distal to the "Protectrode" 12 forms the other electrode. The metallic case of the power source provides an electrical feedthrough from the "Protectrode" 12 to a flexible circuit board, thereby simplifying construction.

"Radome"

Informally, the non-electrically conductive semi spherical end cap forms a "Radome" (radar dome) 13 that serves as a housing for a high frequency antenna used for RF data exchange. FIG. 30 is a side perspective view showing the semi spherical end cap ("Radome") of the IMD 500 of FIG. 28. A high frequency antenna 534 for data exchange is housed within the "Radome" 513. Note that more than one high frequency antenna could be included. The "Radome" 513 is an assembly that includes an electrically insulated semi sphere 517 formed from a medical implantation-safe grade material, such as acrylic, glass, ruby crystal, or ceramic, and a metallic weld ring 521 formed from a medical grade titanium or similar medical implantation-safe metal. These parts are bonded together using pressure fitting, brazing, laser welding, or electron beam welding. In a further embodiment, the high frequency antenna is defined as part of a flexible circuit board or folded metal shape, folded wire, or other similar structure, as further described infra.

"Protectrode"

Informally, the electrically conductive semi spherical end cap forms a "Protectrode" (feeder electrode) 512 that serves a dual purpose as an electrode and as housing for patient and device protection components. FIG. 31 is a side perspective view showing the electrically conductive semi spherical end cap ("Protectrode") of the IMD 500 of FIG. 28. The "Protectrode" 512 is an assembly that includes an electrically conductive semi sphere 514 formed from a medical grade titanium or similar medical implantation-safe conductor, an insulator ring 515 formed from a medical implantation-safe grade material, such as acrylic, glass, ruby crystal, or ceramic, and a metallic weld ring 516, which can include a chamfered edge 523 to facilitate welding to the central body 511, formed from a medical grade titanium or similar medical implantation-safe metal. These parts are bonded together with heat fitting, press fitting, brazing, epoxy adhesive, silicon adhesive or other similar bonding agent.

The construction details of the "Protectrode" 512 will now be discussed. FIG. 32 is an inside perspective view showing the interior of the end cap 514 of the "Protectrode" 512 of FIG. 31. In one embodiment, a set of concave dimples 526 is formed along an inside shelf surface of the end cap 514. The dimples 526 increase surface area and thereby facilitate adhesion of the end cap 514 to the insulator ring 515, they also resist circular rotation. FIG. 33 is an inside perspective view showing the interior of the end cap 514 of the "Protectrode" 512 of FIG. 31. A circumferential groove 525 is longitudinally defined within a cavity 524 inside the end cap 514. The groove 525 provides a mounting location for a circuit board 527. The edges of the circuit board 527 are plated with a set of electrically conductive coatings 528 that include, starting from the circuit board 527 and proceeding outward, copper, nickel (thickly applied), palladium (thinly applied), and gold (of medium thickness), although other materials and combinations of layers are possible. The conductive coatings 528 are necessary to ensure against a galvanic reaction between the copper traces of the circuit board 527 and the titanium shell of the end cap 514. The "Protectrode" may be filled with epoxy or a similar material such as silicon to increase strength and dielectric breakdown properties and provide resistance to corrosion. The filler also will bond with the insulator when the insulator is made out of a brittle material such as ruby, glass or ceramic. The adhesive will hold in place the brittle material should the material fracture during an extreme impact event, such as a car crash.

FIG. 34 is an inside perspective view showing the interior of the fully assembled "Protectrode" 512 of FIG. 31. The edges of the circuit board 527 contact the "Protectrode" 512 along the groove 525. The edges of the circuit board 527 contact the "Protectrode" 512 in two places, in the groove 525 along the end cap 514 and in the groove 525 along the metallic weld ring 516 (the groove 525 is formed along only one side of the metallic weld ring 516, but could be formed along both sides).

FIG. 35 is an exploded perspective view showing the components of the "Protectrode" of FIG. 31. The circuit board 527 includes a protection circuit 535 for the electrode dipole. The insulator ring 515 electrically isolates these two contact points, thereby allowing the protection circuit 535 to interface with both electrodes, that is, the "Protectrode" 512 and the conductive surface 518.

Flexible Circuit Board

The primary electrical structure of the IMD 500 is made out of a single flexible circuit board, which effectively eliminates many inter-circuit board connections and the delicate construction required to create them.

Folded Shape

The flexible circuit board 530 resembles a piece of origami paper that is folded into final shape, which is expected to increase device longevity and reliability by simplifying the design and eliminate the commonly-encountered failure points found in traditional designs. FIG. 36 is a top plan view of a flexible circuit board 530 for use in the IMD 500 of FIG. 28 in a flat, unfolded form. The flexible circuit board 530 is formed out of a single piece of flexible circuit board substrate defining a flexible circuit board 530 for placement of the microcontroller and device circuitry, a pair of vertically disposed foldable "ears" 532 provided on opposite ends of the flexible circuit board 530, and a foldable (or rollable) area 533 that acts as a receiving coil for inductive power coupling. On one end of the flexible circuit board 530, a foldable ear 532 connects to a power source and the feedthrough provided by the power source's case. On the other end of the flexible circuit board 530, the foldable ear 532 either connects to a high frequency antenna that is a separate component contained within the "Radome" 513 or the foldable ear 532 itself forms the high frequency antenna 523. The flexible circuit board 530 can include circuit traces on all sides, or multiple layers covered by an insulating layers to maximize space utilization. In one embodiment, the receiving coil's circuit traces are copper, although other types of conductive materials could be used.

FIG. 37 is a three-quarters perspective view of the flexible circuit board 530 of FIG. 36 in a semi-folded configuration. When placed within the central tubular body, the flexible circuit board 530 forms three aspects 531 of a microcontroller circuit assembly that respectively define a receiving coil 536 for energy capture, a pair of inter-device connecting ears 532, and a printed circuit board 537 containing a low power microcontroller and device circuitry operable to execute under modular micro program control as specified in firmware. The flexible circuit board 530 can be folded into a triangular shape or horseshoe shape (not shown) and each of the inter-device connecting ears 532 are folded angularly inward towards the triangular ends of the triangular shape 534. The foldable area 533 is either folded or rolled around the triangular shape of the flexible circuit board 530 and ears 532. Other shapes may be possible, including other variations on "ears" or extensions to the flexible circuit board 530.

Receiving Coil

A power receiving coil 536 is formed by folding (or rolling) the foldable (or rollable) area 533 (shown in FIG. 36) circumferentially about the triangular or horseshoe shape that contains the microcontroller and device circuitry. As further described below, the power receiving coil 536 may be composed of multiple individual receiving coils. The foldable (or rollable) area 533, however, is longer than the flexible circuit board 530 and is defined, when installed inside the IMD 500, to extend for substantially the entire longitudinal length of the tubular body 511. The receiving coil 536 uses planar trace construction to maximize the capture of magnetic flux and provides insulation between the positive and negative electrode poles of the IMD 500. In further embodiments, signals can be routed from the spherical end caps through the antenna. As well, additional sensors can be implanted in the antennas.

In one embodiment, the receiving coil 536 that is used for gathering energy to recharge the power source is connected to a clamping diode array and fusible link. In the presence of extreme electromagnetic environments, the protection diode array will limit the voltage across the antenna protecting the device charging circuitry. If the diode array is overwhelmed for a long enough period of time, the fusible link will open to protect the patient from the effects of device heating due to excessive charging energy received from the receiving coil. The fusible link may optionally be constructed out of a resettable overcurrent device, thermally actuated device, or fusible current limiting device.

In a further embodiment, the foldable (or rollable) area 533 is defined to form, when installed inside the IMD 500, a diagonal antenna that (not shown) will limit dead zones by creating a spiral where the two halves of the receiving coil connect. A standard square-shaped receiving coil could potentially lead to an RF dead zone in certain orientations. The diagonal antenna has a wide track and is overlaid, so that there are two overlapping areas, which should result in efficient flux capture for fields passing through the antenna.

In one embodiment, the high frequency antenna, when formed on a foldable ear 532 of the flexible circuit board 530, can be folded in different ways to create a range of antenna shapes. Note that more than one high frequency antenna could be used. The antenna is completely integrated into the flex circuit, which eliminates feedthrough that also translates into much better energy coupling.

In one embodiment, the receiving coil is sandwiched between the central tubular body 511, which can be a titanium cylindrical enclosure, and the case of the power source, described infra, which can also be a cylindrical titanium battery case. During inductive charging, eddy currents are induced in the titanium battery case. The eddy currents can raise the temperature of the IMD 500 and can reduce charge efficiency. This effect can be countered by reflecting the low frequency charging magnetic field into the low frequency energy receiving antenna with the increase in efficiency resulting in less heating. A ferrite coating or ferrite sheet can be applied to the outside casing of the power source to increase charge transfer efficiency by reflecting energy back into the receiving coil. Since the energy is reflected, less heating of the power source will occur during inductive charging due to decreased eddy currents.

Forming the power receiving coil 536 by folding or rolling the flexible circuit board provides several benefits over conventional implantable device design. First, the folding or rolling of the flexible circuit board affords a thin design that facilitates patient comfort by enabling compact packaging, resulting in a smaller device than would otherwise be available in a comparably rechargeable design. Second, the wide aspect ratio of the power receiving coil, when compared with to a traditional wire coil, allows a low loss element, thereby decreasing device heating. Moreover, the low loss element enables quicker charging through higher energy reception without excessive heating. Third, the unique shape enables injectable implantation technique that are not possible with traditional planar coils. Finally, the completely integrated design of the printed circuit board containing the microcontroller and related circuitry and the receiving coil simplifies device design, decreases weight, improves device longevity, and increases patient safety by virtue of requiring fewer parts and no discrete interconnections using, for instance, soldered wires or circuit traces.

As mentioned above, the power receiving coil 536 can be formed by multipole individual coils. In particular, the power coil 536 could be the double-helix shaped coil 750 described above with reference to FIG. 20-26B, with the one or more pairs of overlapping coils 261A, 261B making up the coil 750 having a title angle of substantially 45° and each coil 261A, 261B in that pair being orthogonal to the other coil 261A, 261B in the pair. The coils 261A, 261B could be rolled up from a flat state to form the double-helix coil 750 as part of rolling up the circuit board.

The power coil 536 could also be formed by other kinds of coils, including single-phase coils, poly-phase coils, single-layer coils, and multi-layer coils. As described further below, all of these coils can be rolled up into a tubular shape suitable for use in the IMD 500. Poly-phase coil include multiple individual coils that can act as receiving coil for inductive charging. Due to the different positions of the receiving coils in the poly-phase coil, even when the poly-phase coil assumes angular orientations that would other be misaligned with the transmitting coil, at least one of the receiving coils would be in position to efficiently couple with the transmitting coil and receive energy that could be used for powering the circuitry of the IMD 500 (including recharging the power source of the IMD 500). Thus, such poly-phase coils can compensate for the misalignment of the transmitting coil (such as the transmitting coil 263), facilitating quick recharging of the IMD 500 even in the hands of an inexperienced user. Multi-layered coils have an increased inductive coupling efficiency compared to single-layer coils; both a poly-phase coil and a single-phase coil can be multi-layered. Finally, coils that are both single-phase and single-layered can be useful in recharging an implantable monitor that for some reason cannot be rotated, with the fixed position and simplified structure of the coil allowing to position the transmitting coil (such as the transmission coil 263 or a transmission coil of another shape) in a way that would increase the charging speed.

All of the receiving coils in a poly-phase coil are wound up in the same direction (such as clockwise, though other directions are also possible) to avoid magnetic coupling between receiving coils. FIG. 41 is a diagram showing an unrolled 3-phase coil 701 that is composed of three receiving coils 261 in accordance with one embodiment. The 3-phase coil 701 also includes an interconnect region 702 that is used to connect the coil 701 and provide the current generated by the coil 701 to other parts of the IMD 500 (such as to the clamping diode array and the fusible link)—while in this and several other FIGURES below, some of the terminals on the interconnect region are not shown as connected to the receiving coils 261, the connections are present and are visible from other views (similarly to what is illustrated in FIGS. 47A-47B). The 3-phase coil can be rolled up along the axis 703 shown with dashed lines. FIGS. 42A and 42B show two views of the 3-phase coil 701 of FIG. 41 when rolled up in accordance with one embodiment. The dashed arrow 704 shows the magnetic flux vector. The tubular shape of the rolled up coil 701 allows the coil 701 to conveniently fit within the tubular housing of the IMD 500. Numeral 751 denotes the last trace in the spiral of each coil 701—following the last trace 751, there is a layer transition and trace runs towards the interconnect. In the interests of clarity, numeral 751 is shown only with reference to one of the coils 261 on FIG. 41, but the same numeral could be used for the same elements on FIG. 41 and all subsequent FIGURES depicting the receiving coils.

Other numbers (both even and odd numbers) of receiving coils 261 in a poly-phase coil are also possible. For example, a poly-phase coil could include four and six receiving coils 261. FIG. 43 is a diagrams showing an unrolled 4-phase coil 705 that is composed of four receiving coils 261 in accordance with one embodiment. Similarly to above, the coil 705 includes an interconnect region 702 that is used to connect the coil 705 and provide the current generated by the coil 702 to other parts of the IMD 500 (such as to the clamping diode array). The 4-phase coil 705 can be rolled up along the axis 703 shown with dashed lines. FIGS. 44A and 44B show two views of the 4-phase coil 705 of FIG. 42 when rolled up in accordance with one embodiment. The dashed arrow 704 shows the magnetic flux vector. The tubular shape of the rolled up coil 705 allows the coil to conveniently fit within the tubular housing of the IMD 500.

FIG. 45 is a diagrams showing an unrolled 6-phase coil 706 that is composed of six receiving coils 261 in accordance with one embodiment. Similarly to above, the coil 706 includes an interconnect region 702 that is used to connect the coil 706 and provide the current generated by the coil 702 to other parts of the IMD 500 (such as to the clamping diode array). The 6-phase coil 706 can be rolled up along the axis 703 shown with dashed lines. FIGS. 46A and 46B show two views of the 6-phase coil 706 of FIG. 44 when rolled up in accordance with one embodiment. The dashed arrow 704 shows the magnetic flux vector. The tubular shape of the rolled up coil 706 allows the coil to conveniently fit within the tubular housing of the IMD 500.

Still other shapes of the unrolled coils that roll-up into a tubular state that can be used inside the IMD 500 are also possible. FIGS. 47A-47B show a plurality of unwrapped coils 710-718 in accordance with one embodiment. FIG. 47A shows the coils 710-718 from one side ("top") and FIG. 47B shows the coils 710-718 from an opposite side ("bottom") to one shown with reference to FIG. 47A. The coils can be rolled up into the tubular shape similar to what is seen with reference to FIGS. 42A-B, 44A-B, and 46A-B, and act as the receiving power couple 536. All of the coils 710-718 include interconnect region 702 (numeral marked only on coil 716 in the interest of clarity) and all of the coils 710-718 include at least one individual receiver coils 261 (numeral marked only on coil 713 in the interest of clarity).

A detailed description of the coils 710-718 is given below. In those coils that are described as multi-layered, all of the spiral orientations are in the same direction so that the generated current would not be cancelled out. Coil 711 includes is a single-phase, single layer coil, including only a single coil 261 on a top, and a direct return path to the interconnect 702 on the bottom. Coil 712 includes a coil on top layer and a coil on the bottom layer that are electrically connected through a via. Coil 714 is single-layered and flag-shaped and includes a single coil 261 on top, with a direct return path to the interconnect region 702 on the bottom. Coil 715 is multi-layered and flag-shaped, including a coil 261 on top layer and a coil 261 with the same pattern bottom layer, with the layers being electrically connected. Coil 710 is single-layered and includes three staggered independent coils 261 on top with simple return paths (to the interconnect region 702) and is a poly-phase coil. Coil 713 is multi-layered and poly-phase, includes three staggered independent coils 261 on top layer and three independent staggered coils 261 on the bottom layer, each coil 261 in top layer being electrically connected (through vias) to the opposite coil 261 in the bottom layer. Coil 717 is single-layered and poly-phase and includes three independent coils 261 on top with simple return paths (to the interconnect region 702). Coil 718 is multi-layered includes three independent coils 261 on top layer and three independent coils 261 on bottom layer, each coil 261 in top layer being electrically connected (through vias) to the opposite coil 261 in the bottom layer. Coil 716 includes two independent coils 261 on top, with simple return paths to the interconnect region 702.

As mentioned above, all of the coils 710-718 can be rolled up in a tubular shape. FIGS. 48 and 49A-B illustrate the rolling up of the coil 714 of FIG. 47A-47B. FIG. 48 is an expanded view of the unrolled coil 715 of FIGS. 47A-47B. FIG. 49A shows a partially rolled-up coil 715. FIG. 49B shows fully-rolled up coil 715. Similarly, FIGS. 50-51 illustrate the rolling up of the coil 710 of FIG. 47A-47B. FIG. 50 is an expanded view of the unrolled coil 710 of FIGS. 47A-47B. FIG. 51 shows fully-rolled up coil 710. The line 742 indicates fold geometry.

Still other coil shapes that can be rolled up into the tubular shape and used as the power receiving coil 536 are possible. FIG. 52 a plurality of unwrapped coils 720-728 in accordance with one embodiment. All of the coils 720-728 include interconnect region 702 (numeral marked only on coil 724—connections to the interconnect region 702 not shown in FIG. 52 are visible from the opposite side) and all of the coils 710-718 include at least one individual receiver coils 261 (numeral marked only on coil 723). Coils 726-728 must be double-wrapped when folded into the tubular shape. Coil 726 is single-layered, Coil 728 is multi-layered, and Coil 727 has different wire trace thickness (with the center portion having a thicker wire trace thickness and side portions having thinner wire trace thickness). Coil 720 is single-layered and only includes one individual coil 261. Coil 721 is multi-layered. Coil 724 is identical to Coil 721.

Coil 725 is single-layered and has a smaller trace width than in other designs shown. Coils 722 and 723 are poly-phase coils, composed of three individual coils 261. The Coil 722 is double-layered, and the Coil 723 is single-layered. Coils 720-725 are only single-wrapped to form the tubular shape.

While the above-described coil designs are either double or single-wrapped to create the tubular shape, in a further embodiment, other numbers of wrappings are possible. FIG. 53 is a diagram showing a two-phase coil 731 that needs to be wrapped around 1.5 times to create the tubular shape. The coil 731 includes two individual receiving coils 261 (with one being a part of the bottom layer that is not shown).

One or more of the coils described above with reference to FIGS. 41-53 and the double-helix shaped coil 750 could be combined within a single implantable monitor (such as the monitor 500). Further, while the coils that can form the power receiving coil 536 fit the tubular housing of the IMD 500, in a further embodiment, they could be used in a different kind of implantable physiological monitor. The coils that can form the power receiving coil 536 can be recharged using the transmitting coil 263, though other shapes of transmission coils are also possible. Further, as described above, the monitor being recharged (including the IMD 500) could offload gathered data while the external device 380 that includes both energy transmitting and data download capabilities as described above.

Power Source and Charging Circuit

A power source that includes an inductively-rechargeable energy cell, battery, or supercapacitor is also placed within the IMD 500 to one end of the flexible circuit board 530 and in electrical contact with the electrically conductive semi spherical end cap 513, thereby serving as an electrical feedthrough to the flexible circuit board 530. The power source may be recharged through a charging and conditioning circuit interfaced with the microcontroller using a non-contact method, such as inductive charging, resonant charging, energy harvesting, thermal gradient charging, ultrasonic charging, RF-based charging or charging by ambient or driven motion including vibration. When recharging using inductive coupling, the transmitting circuit 263 can be used, though use of other circuits is also possible. Low frequency charging circuits are most efficient at transmitting energy through solid objects. When a charging circuit operates, vibrations are induced in the coils used in the charger as well as surrounding conductive objects. However, these vibrations, if within the human audible hearing range (or a close multiple thereof) create sound.

A traditional charging circuit uses a single frequency to transmit power. If the frequency or a major harmonic thereof is within the audible human hearing range, a single tone that humans can find very annoying could result. To overcome this issue, traditional charging circuits operate above the human audible hearing range. However, instead of using a single frequency for charging, a low frequency charging circuit could also modulate the charging waveform at audible frequencies that result in a pleasant sound for the user, so as to allow the technical benefits of low frequency charging without causing annoyance to humans.

Modulation of frequencies requires receive and transmit circuitry with higher bandwidth to accommodate the frequency shifts efficiently. The modulation can cause decreased circuit Q ("quality"), which can be overcome by using a variable capacitor or other automatic tuning circuit to ensure sufficient resonance as the frequency changes. For example, if the frequency changes, tuning may be required to restore satisfactory coupling. The automatic tuner circuit could predict the value needed to achieve resonance or a high Q factor based on the input frequency, or alternatively could employ a feedback system to self-tune as the input frequency changes. The automatic tuner circuit could further be employed to efficaciously control charging to decrease overall charging time. Differences in devices, patients and their environment will modify the Q factor of the system. An automatic turning circuit can automatically compensate for these changes.

In a still further embodiment, a feedback circuit or system could be further employed to automatically compensate for changes in the environment and patient load. The feedback circuit would tune charging based on input energy. Alternatively, the feedback circuit method is to know what is coming and instantly auto tune the charging circuitry based on the pattern that will be sent shortly to the IMD 500.

The feedback system could also be used to provide positive feedback to the patient. For instance, the modulation frequency could produce a very "futuristic" sound, such as a low to high frequency ramp, which repeats at a predetermined interval, or could even play a song, perhaps of the patient's choosing. Further, the modulation frequency could be used to signal to the user the state of the device, such as charging, error condition, or completion of charging.

Encasement

The power source may optionally be encased in a metallic cylindrical case that also functions as an electrical feedthrough, where the outside of the power source case is used as a conductor to the electrode connection. Conventional IMDs are typically rectangular or prismatic in shape. A cylindrical shape offer several advantages, including patient comfort, power source design, accommodations for different types of antennae, and improved insertability and ease of explant.

The actual electrode contact area forms a hollow dome to absorb any swelling that might occur during the extremely unlikely event of a catastrophic power source failure. A set of feedthroughs, arranged in a possible pattern of [+/Temp/−/chassis] is provided to provide increased safety, reduction of leakage currents and ease of assembly.

In one embodiment, the power source case is electro polished to improve the ability of the receiving coil 536 to slide over the power source case during installation. In a further embodiment, the head of the power source, that is, the end of the power source that faces outwards away from the flexible circuit board 530 and replaces the "Protectrode" assembly. The head is formed of thin titanium and shaped as a dome to serve as an electrode and provide internal relief for power source expansion if a failure occurs.

Chemistry

In one embodiment, the power source can use lithium titanate (LTO) technology. Alternatively, other power source or battery technologies such as Lithium Cobalt Oxide, Lithium Manganese Oxide, Lithium Nickel Manganese Cobalt Oxide, Lithium Iron Phosphate, Lithium Nickel Cobalt Aluminum Oxide, Nickel Cadmium or Nickel Meta Hydrate could be employed.

To accommodate complete discharge without oxidation of the power source collector, the copper collector typically found in a power source could be replaced by a corrosion resistant metal, such as stainless steel, titanium, gold or platinum. Furthermore, a collector could be made of a standard base metal and plated to increase corrosion resistance. This combination of materials could be copper, nickel, palladium, gold or titanium, gold, or stainless steel, gold or any appropriate combination thereof to provide the necessary degree of corrosion resistance and zero volt life. The surfaces of the materials and platings could be roughened to increase surface area and provide better charge and discharge characteristics.

Scalloped Electrodes

The proximity of the high frequency antenna 534 to the conductive surface 18 exposed on the outside surface of the tubular body 511 can, in some circumstances, pose a risk of ECG signal degradation. FIG. 38 is an outer perspective view showing an IMD 560 that houses a configurable hardware platform for physiological monitoring of a living body in accordance with a further embodiment. The electrode 561 formed as part of the "Protectrode" section of the IMD 560 and the electrode 562 formed on the outer surface of the tubular body 511 are shaped with scalloped cutouts on their respective inward facing aspects. The electrode formation minimizes potential parasitic coupling of the electrodes 561 and 562 to ground strips that are used for the high frequency antenna return. In addition, the shape of the "Protectrode" electrode 561 increases the performance and durability of the ceramic to titanium weld joints, when used, to join the "Protectrode" 512 to the tubular body 511.

Microarchitecture

The operation of the IMD 500, including data capture, analysis, and communication, is controlled by a programmable microcontroller. FIG. 39 is a block diagram showing the microarchitecture 540 of the IMD 500. The microcontroller is remotely interfaceable over a wireless radio frequency (RF) data communications link using the high frequency antenna 534 that is housed within the "Protectrode" 512, which enables the EIMD 500 to provide continuous heartbeat-by-heartbeat monitoring and to be remotely reconfigured or reprogrammed to utilize one or more of the physiological sensors.

Microcontroller

In one embodiment, a low power, high efficiency microcontroller 541, such as a microcontroller from the RL78 family of microcontrollers offered by Renesas Electronics Corp., Tokyo, Japan, can be used. Architecturally, the microcontroller is built around a Harvard architecture that physically separates signal and storage pathways for instructions and data storage. The microcontroller operates under a dedicated microprogram stored as microcode within a non-volatile memory device, rather than a general purpose operating system, which aids in efficient operation and longer power source life, although in a further embodiment, an operating system including a real time operating system, could be used. Note that there is memory located on the microcontroller as well as externally and program instructions are expected to be stored in the microcontroller's flash memory.

Additional Components

The microcontroller 541 is interfaced to components, both integrated and off-chip, that provide continuous and extensible monitoring capabilities to the IMD 500. A voltage regulation/charge control circuit 48 is interfaced to the low frequency resonant charger antenna 547 and the microcontroller 541, which together regulate and control the charging of the power source 549. An integrated Bluetooth system-on-a-chip (SoC) transceiver circuit 542 is similarly interfaced to the high frequency antenna 534 and the microcontroller 541 to provide data communications capabilities to the IMD 500. An electrode dipole is formed by electrodes 545 and 546, which are interfaced to an analog front end (AFE) 544 and to the microcontroller 541 to effect electrocardiographic monitoring. In one embodiment, temperature, actigraphy, and motion sensing are respectively provided through a temperature sensor 550, Hall effect switch 551, and accelerometer 552. Finally, monitoring data, including continuous ECG data awaiting offloading, are stored in mass storage 553 in the form of random access memory.

Paradigm

Purpose-build IMDs, such as implantable cardiac monitors (ICMs), are specifically designed to address a range of potential conditions which would be observable over an expected patient population. Thus, typical ICMs require power hungry and complex signal filters, which are able to detect R-wave intervals on a very high percentage of the patient population. Practically, however, the majority of the patient population does not need extreme filtering. As a result, dramatic power savings are possible if a signal filter could be selected that is appropriate for a given patient and for patients with special needs, strong signal filtering can be selected to reduce false positives at the cost of high power consumption and frequent recharging.

Here, the IMD 500 implements a configurable hardware platform based on a reprogrammable microcontroller that can be supplemented with additional physiological sensors, including an $SpO_2$ sensor, a blood pressure sensor, a temperature sensor, respiratory rate sensor, a glucose sensor, an air flow sensor, and a volumetric pressure sensor, and non-physiological sensors, including an accelerometer and inertial motion sensor. Through the microcontroller 41, the sensors can be selectively activated over the implantation lifetime, whether in real time or during reprogramming, to tailor the monitoring of the patient to ongoing diagnostic needs.

The microcontroller-based design also affords the flexibility to choose signal filtering and processing algorithm options tailored to each patient. This microarchitecture allows the best patient experience by eliminating designs that adopt a one-size-fits-all approach and which are dominated by considerations of accommodating the hardest cases. The microarchitecture further accommodates changes to patient morphology; modifications to the filtering software can be selected dynamically and updated in the field as a configuration update that is pushed by a physician from the "cloud," that is, the server paradigm that virtualizes server-side functionality as a service widely available through access to the internet or other wide-area data communications network.

In a further embodiment, the transceiver 542 can be used in conjunction with the microcontroller to communicate with ingestible sensors, such as offered by Proteus Digital Health, Inc., Redwood City, CA. Ingestible sensors are pills made of biocompatible materials, which combine remote monitoring microelectronics with medication or inert materials that can safely be taken by a patient. Typically, an ingestible sensor is activated by gastric fluids dissolving or acting upon its surface, after which the sensor begins to measure gastro-intestinal tract physiology and, possibly, other types of physiology. Ingestible sensors that are capable of communicating wirelessly, such as over Bluetooth, Medradio, or via WiFi, are available as a real-time-capable alternative to standalone ingestible sensors that store recorded physiology onboard the device. This wireless-capable class of ingestible sensors allows the sensory data to be captured in real time. Moreover, these types of ingestible sensors aAcan be coupled with the IMD 500; thus, a patient can be monitored for medication compliance by providing accurate, time-correlated data that can be used to evaluate non-adherence and to provide positive reinforcement. The patient's caregiver can be notified in real time as to a patient's behavior with respect to adhering to prescribed medication.

The platform described facilitates the monitoring of every heartbeat in contrast to conventional non-rechargeable platforms, which typically do not have enough power to store and transmit each heartbeat. In addition to monitoring each heartbeat, since the heartbeats are offloaded, the heartbeats may be analyzed by an intelligent algorithm not located in the platform proper, which allows for better recognition of arrhythmias and disease conditions, as the complexity of the algorithm is not limited by the amount of power available to the analyzing device.

The IMD 500 continuously monitors the patient's heart rate on a heartbeat-by-heartbeat basis and physiology. FIG. 40 is a flow diagram showing a method 600 for continuously monitoring electrocardiography for use in the IMD 500 of FIG. 28. Initially, following successful implantation, the microcontroller 541 executes a power up sequence (step 101). During the power up sequence, the voltage of the power source 549 is checked, the state of the mass storage (flash memory) 553 is confirmed, both in terms of operability check and available capacity, and microcontroller operation is diagnostically confirmed.

Following satisfactory completion of the power up sequence, an iterative processing loop (steps 602-614) is continually executed by the microcontroller 541. During each iteration (step 602) of the processing loop, the AFE 544, through the electrode dipole created by electrodes 545 and 546, continually senses electrocardiographic signals; additionally, patient physiology is sampled at appropriate intervals, depending upon the sampling frequency selected for the particular type of physiology being sensed (step 503). One or more types of physiology can be sensed at any given time. The type and sampling rate of physiology are selectively activated over the lifetime of the IMD 500 via the microcontroller through programmatic control, which in turn, determines the hardware device being utilized. For instance, reading patient temperature once each minute would require activation of the temperature sensor 550. A similar approach to sensing non-physiological data, such as position or posture, is followed mutatis mutandis.

A sample of the ECG signal and, at appropriate intervals, physiology, are read (step 604) by the microcontroller 61 by sampling the AFE 544 and appropriate physiology sensing hardware. Each sampled ECG signal and each of the physiology signals, in quantized and digitized form, are temporarily staged in a buffer (step 605), pending compression preparatory to storage in the mass storage 553 (step 606). Following compression, the compressed ECG digitized samples are again buffered (step 607), then written to the mass storage 553 (step 608) using the communications bus. Processing continues (step 614), so long as storage space remains available in the mass storage 553, after which the processing loop is exited. Still other operations and steps are possible.

The IMD 500 processes sensing signals generated by ingestible sensors follow a similar methodology as with processing monitored physiology, with two important distinctions. First, ingestible sensors are typically activated upon ingestion and thereafter generate monitoring data only during the time in which they are present in the patient's digestive tract. Second, ingestible sensor data is generally time-sensitive, where the correlation of the time of signal generation and time of day is of notable interest in itself, whereas physiological data is typically seen in the context of other physiological events, such as $SpO_2$, which is significant with reference to cardiac events.

Concurrently, the IMD 500 can offload stored monitoring data to a datacenter or other external device. The data is offloaded in a conceptually-separate execution thread as part of the iterative processing loop (steps 602-614) continually executed by the microcontroller 541. If an offloading event occurs (step 609), the IMD 500 connects to a mobile device (step 610), such as a smart phone or cellular-enabled tablet, and the stored samples are sent from the mass storage 553 to the mobile device (step 511). In turn, the mobile device relays the uploaded ECG and physiology samples to the datacenter. Alternatively, the IMD 500 can connect directly to the datacenter, provided the transceiver 542 is sufficiently capable. The mass storage 553 is cleared (step 512) and the IMD 500 disconnects from the mobile device (step 513) upon completion of the sending of the stored samples. Processing continues (step 514). Still other operations and steps are possible.

While the invention has been particularly shown and described as referenced to the embodiments thereof, those skilled in the art will understand that the foregoing and other changes in form and detail may be made therein without departing from the spirit and scope.

What is claimed is:

1. An implantable physiological monitor, comprising:
- a transceiver configured to wirelessly interface with an external device;
- a housing having a plurality of electrodes, wherein the plurality of electrodes is configured to record an electrocardiography signal; and
- a power source comprising a rechargeable power cell and an energy harvesting module comprising multiple receiving coils which minimize parasitic interactions between the multiple receiving coils,
- wherein an electrode configuration of the plurality of electrodes can be programmatically selected via the external device, after implanting the implantable physiological monitor.

2. The implantable physiological monitor of claim 1, wherein the housing comprises a distal end and a proximal end, wherein the distal end is opposite the proximal end, and wherein the plurality of electrodes comprises:
- a first ventral electrode disposed on the distal end of the housing;
- a second ventral electrode disposed on the proximal end of the housing;
- a first wraparound electrode disposed on the distal end of the housing; and
- a second wraparound electrode disposed on the proximal end of the housing.

3. The implantable physiological monitor of claim 2, wherein the first ventral electrode can be paired to the first wraparound electrode, and the second ventral electrode can be paired to the second wraparound electrode in the electrode configuration.

4. The implantable physiological monitor of claim 2, wherein the first wraparound electrode can be paired to the second wraparound electrode, and the first ventral electrode can be paired to the second ventral electrode in the electrode configuration.

5. The implantable physiological monitor of claim 2, wherein the first wraparound electrode can be paired to the second ventral electrode, and the first ventral electrode can be paired to the second wraparound electrode in the electrode configuration.

6. The implantable physiological monitor of claim 2, wherein the first wraparound electrode can be logically combined with the first ventral electrode to form a single virtual electrode.

7. The implantable physiological monitor of claim 2, wherein the housing further comprises a third ventral electrode and a fourth ventral electrode, wherein the third ventral electrode and the fourth ventral electrode are paired together in the electrode configuration.

8. The implantable physiological monitor of claim 1, wherein configuring the electrode configuration varies a surface area of at least one of the plurality of electrodes.

9. The implantable physiological monitor of claim 1, wherein configuring the electrode configuration varies an inter-electrode spacing between at least two of the plurality of electrodes.

10. The implantable physiological monitor of claim 1, wherein the electrode configuration of the plurality of electrodes is configured via the external device.

11. The implantable physiological monitor of claim 1, the external device is a mobile device.

12. The implantable physiological monitor of claim 1, wherein a sub-plurality of the plurality of electrodes can be deactivated after implanting the implantable physiological monitor.

13. The implantable physiological monitor of claim 1, wherein the electrode configuration of the plurality of electrodes can be configured after implanting the implantable physiological monitor to increase P-wave resolution of the electrocardiography signal.

* * * * *